United States Patent
Prod'Homme et al.

(10) Patent No.: US 12,297,256 B2
(45) Date of Patent: *May 13, 2025

(54) METHODS FOR THE TREATMENT OF NEURODEGENERATION

(71) Applicant: Momenta Pharmaceuticals, Inc., Titusville, NJ (US)

(72) Inventors: Thomas E. Prod'Homme, Titusville, NJ (US); Leona E. Ling, Titusville, NJ (US); Carlos J. Bosques, Titusville, NJ (US); Anthony Manning, Titusville, NJ (US); Ganesh Kaundinya, Titusville, NJ (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 30 days.

This patent is subject to a terminal disclaimer.

(21) Appl. No.: 17/739,912

(22) Filed: May 9, 2022

(65) Prior Publication Data

US 2022/0267413 A1 Aug. 25, 2022

Related U.S. Application Data

(63) Continuation of application No. 16/671,595, filed on Nov. 1, 2019, now Pat. No. 11,352,415, which is a continuation of application No. 14/890,865, filed as application No. PCT/US2014/037761 on May 13, 2014, now Pat. No. 10,464,996.

(60) Provisional application No. 61/822,795, filed on May 13, 2013.

(51) Int. Cl.
  *C07K 16/00* (2006.01)
  *A61K 39/00* (2006.01)
  *C07K 16/06* (2006.01)
  *G01N 33/68* (2006.01)

(52) U.S. Cl.
  CPC .............. *C07K 16/00* (2013.01); *C07K 16/06* (2013.01); *G01N 33/6896* (2013.01); *A61K 2039/505* (2013.01); *A61K 2039/54* (2013.01); *A61K 2039/545* (2013.01); *C07K 2317/41* (2013.01); *G01N 2333/52* (2013.01); *G01N 2500/10* (2013.01)

(58) Field of Classification Search
  CPC .... C07K 16/00; C07K 16/06; C07K 2317/41; G01N 33/6896; G01N 2333/52; G01N 2500/10; A61K 2039/505; A61K 2039/54; A61K 2039/545; A61P 25/28
  See application file for complete search history.

(56) References Cited

U.S. PATENT DOCUMENTS

| | | |
|---|---|---|
| 3,945,889 A | 3/1976 | Mima et al. |
| 4,258,134 A | 3/1981 | Yoshida et al. |
| 4,820,516 A | 4/1989 | Sawyer et al. |
| 4,859,449 A | 8/1989 | Mattes |
| 5,047,335 A | 9/1991 | Paulson et al. |
| 5,068,190 A | 11/1991 | Horiuchi et al. |
| 5,234,905 A | 8/1993 | Kolhouse et al. |
| 5,340,453 A | 8/1994 | Jackson |
| 5,360,817 A | 11/1994 | von Izstein et al. |
| 5,370,872 A | 12/1994 | Crvz et al. |
| 5,411,942 A | 5/1995 | Widmer et al. |
| 5,456,909 A | 10/1995 | Marsh, Jr. et al. |
| 5,459,031 A | 10/1995 | Blumen et al. |
| 5,500,342 A | 3/1996 | Miyamura et al. |
| 5,510,261 A | 4/1996 | Goochee et al. |
| 5,554,730 A | 9/1996 | Woiszwillo et al. |
| 5,559,103 A | 9/1996 | Gaeta et al. |
| 5,567,684 A | 10/1996 | Ladisch et al. |
| 5,663,355 A | 9/1997 | Ganem et al. |
| 5,723,583 A | 3/1998 | Seed et al. |
| 5,747,027 A | 5/1998 | Stern et al. |
| 5,753,454 A | 5/1998 | Lee |

(Continued)

FOREIGN PATENT DOCUMENTS

| | | |
|---|---|---|
| CA | 2828905 | 9/2012 |
| EP | 0798003 | 10/1997 |

(Continued)

OTHER PUBLICATIONS

"Glycosylation main approval issue with biosimilars," <http://gabionline.net/Conferences/Glycosylation-main-approval-issue-with-biosimilars>, dated Jan. 9, 2009, retrieved Jul. 18, 2016 (2 pages).

(Continued)

*Primary Examiner* — Kimberly Ballard
*Assistant Examiner* — Stacey N Macfarlane
(74) *Attorney, Agent, or Firm* — Morgan, Lewis & Bockius LLP

(57) ABSTRACT

The invention encompasses the discovery that Fc-containing polypeptides that include branched glycans and that are sialylated on the branched glycan (e.g., on an α 1,3 and/or α 1,6 arm in the Fc region's N-linked glycosylation site), with, e.g., a NeuAc-α 2,6-Gal or NeuAc-α 2,3-Gal terminal linkage, are useful in treating neurodegeneration, e.g., in the treatment of neurodegenerative diseases such as Alzheimer's Disease. The present disclosure provides, in part, methods for treating neurodegeneration or neurodegenerative diseases by administering compositions containing such Fc-containing polypeptides as well as methods for evaluating, identifying, and/or producing (e.g., manufacturing) such polypeptides for the treatment of neurodegeneration.

16 Claims, 13 Drawing Sheets

Specification includes a Sequence Listing.

(56) References Cited

U.S. PATENT DOCUMENTS

| | | |
|---|---|---|
| 5,759,823 A | 6/1998 | Wonq et al. |
| 5,807,715 A | 9/1998 | Morrison et al. |
| 5,827,721 A | 10/1998 | Stern et al. |
| 5,854,046 A | 12/1998 | Au-Young et al. |
| 5,856,143 A | 1/1999 | Nilsson |
| 5,879,912 A | 3/1999 | Roth |
| 5,945,322 A | 8/1999 | Gotschlich |
| 5,958,750 A | 9/1999 | Au-Young et al. |
| 6,030,815 A | 2/2000 | DeFrees et al. |
| 6,048,707 A | 4/2000 | Klock, Jr. |
| 6,057,110 A | 5/2000 | Au-Young et al. |
| 6,096,555 A | 8/2000 | Hermentin et al. |
| 6,132,994 A | 10/2000 | Tawada et al. |
| 6,156,547 A | 12/2000 | Roth |
| 6,159,954 A | 12/2000 | Maruyama et al. |
| 6,180,370 B1 | 1/2001 | Queen et al. |
| 6,190,522 B1 | 2/2001 | Haro |
| 6,218,149 B1 | 4/2001 | Morrison et al. |
| 6,261,805 B1 | 7/2001 | Wood |
| 6,274,568 B1 | 8/2001 | Schnaar et al. |
| 6,280,989 B1 | 8/2001 | Kapitonov et al. |
| 6,284,516 B1 | 9/2001 | Pollock et al. |
| 6,358,710 B1 | 3/2002 | Graves et al. |
| 6,399,336 B1 | 6/2002 | Bayer et al. |
| 6,597,996 B1 | 7/2003 | Venkataraman et al. |
| 6,946,075 B2 | 9/2005 | Kopf |
| 7,118,675 B2 | 10/2006 | An et al. |
| 7,138,120 B2 | 11/2006 | Laursen et al. |
| 7,364,736 B2 | 4/2008 | Boyle et al. |
| 7,368,542 B2 | 5/2008 | McIntyre |
| 7,465,397 B2 | 12/2008 | An et al. |
| 7,473,680 B2 | 1/2009 | Bowe et al. |
| 7,655,233 B2 | 2/2010 | Autenreith et al. |
| 7,767,429 B2 | 8/2010 | Bookbinder et al. |
| 7,829,081 B2 | 11/2010 | Bookbinder et al. |
| 7,846,431 B2 | 12/2010 | Bookbinder et al. |
| 7,871,607 B2 | 1/2011 | Bookbinder et al. |
| 8,034,906 B2 | 10/2011 | Borhani et al. |
| 8,105,586 B2 | 1/2012 | Bookbinder et al. |
| 8,187,855 B2 | 5/2012 | Baker et al. |
| 8,278,072 B1 | 10/2012 | Matta et al. |
| 8,524,217 B2 | 9/2013 | Presta et al. |
| 8,546,548 B2 | 10/2013 | Bauer et al. |
| 8,632,773 B2 | 1/2014 | Elkon et al. |
| 8,715,652 B2 | 5/2014 | Bolli et al. |
| 8,772,461 B2 | 7/2014 | Earp et al. |
| 8,932,825 B2 | 1/2015 | Wildt |
| 9,114,179 B2 | 8/2015 | Amphlett et al. |
| 9,127,043 B2 | 9/2015 | Gronke et al. |
| 9,170,249 B2 | 10/2015 | Washburn et al. |
| 9,175,068 B2 | 11/2015 | Bauer et al. |
| 9,217,168 B2 | 12/2015 | Prentice |
| 9,481,902 B2 | 11/2016 | Czabany et al. |
| 9,637,768 B2 | 5/2017 | Choi et al. |
| 9,663,581 B2 | 5/2017 | Washburn et al. |
| 9,725,501 B2 | 8/2017 | Earp et al. |
| 9,809,835 B2 | 11/2017 | Engel |
| 9,890,410 B2 | 2/2018 | Washburn et al. |
| 10,087,236 B2 | 10/2018 | Wong et al. |
| 10,125,189 B2 | 11/2018 | Bauer et al. |
| 10,287,315 B2 | 5/2019 | Choi et al. |
| 10,344,063 B2 | 7/2019 | Huang et al. |
| 10,464,996 B2 | 11/2019 | Prod'Homme et al. |
| 10,668,411 B2 | 6/2020 | Lu et al. |
| 10,836,805 B2 | 11/2020 | Huang et al. |
| 11,078,511 B2 | 8/2021 | Greif et al. |
| 11,098,079 B2 | 8/2021 | Gonzalez et al. |
| 11,352,415 B2 | 6/2022 | Prod'Homme |
| 11,377,485 B2 | 7/2022 | Wong et al. |
| 11,661,456 B2 | 5/2023 | Schultes |
| 2002/0054878 A1 | 5/2002 | Lowman et al. |
| 2003/0157108 A1 | 8/2003 | Presta |
| 2004/0137106 A1 | 7/2004 | Ciccone |
| 2004/0138106 A1 | 7/2004 | Schultz et al. |
| 2004/0210396 A1 | 10/2004 | Fischer et al. |
| 2005/0054832 A1 | 3/2005 | Lazar et al. |
| 2005/0106658 A1 | 5/2005 | Bayer et al. |
| 2006/0030521 A1 | 2/2006 | Bayer et al. |
| 2006/0040353 A1 | 2/2006 | Davidson et al. |
| 2006/0127950 A1 | 6/2006 | Bosques et al. |
| 2006/0252672 A1 | 11/2006 | Betenbaugh et al. |
| 2008/0261301 A1 | 10/2008 | Kanda et al. |
| 2009/0041770 A1 | 2/2009 | Chamberlain et al. |
| 2009/0053238 A1 | 2/2009 | Allan |
| 2009/0069232 A1 | 3/2009 | Callewaert et al. |
| 2009/0104603 A1 | 4/2009 | Satomaa et al. |
| 2009/0203550 A1 | 8/2009 | Venkataraman et al. |
| 2009/0226968 A1 | 9/2009 | Betenbaugh et al. |
| 2009/0252749 A1 | 10/2009 | Leister et al. |
| 2009/0258014 A1 | 10/2009 | Laterra et al. |
| 2009/0304665 A1 | 12/2009 | Bilinsky et al. |
| 2009/0311732 A1 | 12/2009 | Rossi et al. |
| 2009/0317834 A1 | 12/2009 | Laine et al. |
| 2010/0048456 A1 | 2/2010 | DeFrees et al. |
| 2010/0074885 A1 | 3/2010 | Schiff et al. |
| 2010/0081150 A1 | 4/2010 | Liu et al. |
| 2010/0113294 A1 | 5/2010 | Venkataraman et al. |
| 2010/0129843 A1 | 5/2010 | Parsons et al. |
| 2010/0136599 A1 | 6/2010 | Gandhe et al. |
| 2010/0144553 A1 | 6/2010 | Bosques et al. |
| 2010/0166774 A1 | 7/2010 | Dali et al. |
| 2010/0173323 A1 | 7/2010 | Strome et al. |
| 2010/0189714 A1 | 7/2010 | Ravetch et al. |
| 2010/0278808 A1 | 11/2010 | Ravetch et al. |
| 2011/0008309 A1 | 1/2011 | Bookbinder et al. |
| 2011/0053247 A1 | 3/2011 | Baker et al. |
| 2011/0076277 A1 | 3/2011 | Ravetch et al. |
| 2011/0263828 A1 | 10/2011 | Wong et al. |
| 2011/0280873 A1 | 11/2011 | Presta et al. |
| 2012/0009189 A1 | 1/2012 | Kasermann et al. |
| 2012/0058111 A1 | 3/2012 | Ehlers et al. |
| 2012/0100575 A1 | 4/2012 | Taylor et al. |
| 2012/0101325 A1 | 4/2012 | Lee et al. |
| 2012/0295273 A1 | 11/2012 | Washburn et al. |
| 2013/0216522 A1 | 8/2013 | Huille et al. |
| 2015/0087814 A1 | 3/2015 | Wang et al. |
| 2015/0210753 A1 | 7/2015 | Sarvaiya et al. |
| 2015/0252108 A1 | 9/2015 | Washburn et al. |
| 2016/0090409 A1 | 3/2016 | Prod'Homme et al. |
| 2016/0108450 A1 | 4/2016 | Bhatnager et al. |
| 2016/0257754 A1 | 9/2016 | Schultes et al. |
| 2018/0186847 A1 | 7/2018 | Wang et al. |
| 2018/0305440 A1 | 10/2018 | Sarvaiya et al. |
| 2018/0305725 A1 | 10/2018 | Bhatnager et al. |
| 2018/0327498 A1 | 11/2018 | Schultes et al. |
| 2019/0002542 A1 | 1/2019 | Li et al. |
| 2019/0085064 A1 | 3/2019 | Bauer et al. |
| 2019/0100573 A1 | 4/2019 | Wong et al. |
| 2019/0161533 A1 | 5/2019 | Hannappel et al. |
| 2019/0194303 A1 | 6/2019 | Wong et al. |
| 2020/0032312 A1 | 1/2020 | Bhatnager et al. |
| 2020/0055921 A1 | 2/2020 | Homme et al. |
| 2020/0087298 A1 | 3/2020 | Bechtold et al. |
| 2020/0087402 A1 | 3/2020 | Schultes et al. |
| 2021/0017563 A1 | 1/2021 | Bhatnager et al. |
| 2021/0040527 A1 | 2/2021 | Bhatnager et al. |
| 2021/0163531 A1 | 6/2021 | Abel et al. |
| 2021/0277438 A1 | 9/2021 | Bhatnager et al. |
| 2021/0353752 A1 | 11/2021 | Arroyo et al. |
| 2022/0056109 A1 | 2/2022 | Sarvaiya et al. |
| 2022/0267413 A1 | 8/2022 | Bosques et al. |

FOREIGN PATENT DOCUMENTS

| | | |
|---|---|---|
| EP | 1038881 | 9/2000 |
| EP | 2233502 | 9/2010 |
| EP | 2271382 | 1/2011 |
| EP | 2403866 | 1/2012 |
| EP | 2996772 | 3/2016 |
| EP | 3004368 | 4/2016 |
| EP | 3017057 | 5/2016 |
| EP | 3118209 | 1/2017 |
| EP | 3237608 | 11/2017 |
| JP | 2002-542787 | 12/2002 |

(56) References Cited

FOREIGN PATENT DOCUMENTS

| | | | |
|---|---|---|---|
| JP | 2005-509403 | 4/2005 | |
| NZ | 597651 A * | 7/2012 | ............ C07K 16/00 |
| WO | WO 92/22324 | 12/1992 | |
| WO | WO 1998/031826 | 7/1998 | |
| WO | WO 98/46645 | 10/1998 | |
| WO | WO 99/64462 | 12/1999 | |
| WO | WO 00/65070 | 11/2000 | |
| WO | WO 01/80884 | 11/2001 | |
| WO | WO 02/00879 | 1/2002 | |
| WO | WO 02/30954 | 4/2002 | |
| WO | WO 02/076578 | 10/2002 | |
| WO | WO 2005/116221 | 12/2005 | |
| WO | WO 2007/005786 | 1/2007 | |
| WO | WO 2007/011041 | 1/2007 | |
| WO | WO 2007/055916 | 5/2007 | |
| WO | WO 2007/076032 | 7/2007 | |
| WO | WO 2007/087384 | 8/2007 | |
| WO | WO 2007/117505 | 10/2007 | |
| WO | WO 2008/057634 | 5/2008 | |
| WO | WO 2008/063982 | 5/2008 | |
| WO | WO 2008/128216 | 10/2008 | |
| WO | WO 2008/128218 | 10/2008 | |
| WO | WO 2008/128219 | 10/2008 | |
| WO | WO 2008/128220 | 10/2008 | |
| WO | WO 2008/128221 | 10/2008 | |
| WO | WO 2008/128222 | 10/2008 | |
| WO | WO 2008/128225 | 10/2008 | |
| WO | WO 2008/128227 | 10/2008 | |
| WO | WO 2008/128228 | 10/2008 | |
| WO | WO 2008/128230 | 10/2008 | |
| WO | WO 2008/130924 | 10/2008 | |
| WO | WO 2008/130926 | 10/2008 | |
| WO | WO 2009/021708 | 2/2009 | |
| WO | WO 2009/058564 | 5/2009 | |
| WO | WO 2009/079382 | 6/2009 | |
| WO | WO 2009/111240 | 9/2009 | |
| WO | WO 2010/071817 | 6/2010 | |
| WO | WO 2010/071824 | 6/2010 | |
| WO | WO 2010/085251 | 7/2010 | |
| WO | WO 2010/130756 | 11/2010 | |
| WO | WO 2010/136492 | 12/2010 | |
| WO | WO 2010/138502 | 12/2010 | |
| WO | WO 2010/138736 | 12/2010 | |
| WO | WO 2010/141855 | 12/2010 | |
| WO | WO 2011/069056 | 6/2011 | |
| WO | WO 2011/103584 | 8/2011 | |
| WO | WO 2011/127322 | 10/2011 | |
| WO | WO 2011/127325 | 10/2011 | |
| WO | WO 2012/113863 | 8/2012 | |
| WO | WO 2012/120125 | 9/2012 | |
| WO | WO 2013/120066 | 8/2013 | |
| WO | WO 2014/018747 | 1/2014 | |
| WO | WO 2014/052360 | 4/2014 | |
| WO | WO 2014/179601 | 11/2014 | |
| WO | WO 2015/001033 | 1/2015 | |
| WO | WO 2015/057622 | 4/2015 | |
| WO | WO 2018/131893 | 7/2018 | |
| WO | WO 2020/077298 | 4/2020 | |
| WO | WO 2020/215021 | 10/2020 | |
| WO | WO 2021/236765 | 11/2021 | |
| WO | WO 2022/038565 | 2/2022 | |

OTHER PUBLICATIONS

"Scientific Considerations in Demonstrating Biosimilarity to a Reference Product: Guidance for Industry," Food and Drug Administration (2012) (25 pages).
Afonso et al., "The Production Processes and Biological Effects of Intravenous Immunoglobulin," Biomolecules, 2016, 6(15):1-20.
Ahn et al., "Separation of 2-aminobenzamide labeled glycans using hydrophilic interaction chromatography columns packed with 1.7 (mu)m sorbent," J Chromatoqr. 878(3-4):403-8 (2010).
Akiyama et al., "Analysis of the role of glycosylation of the human fibronectin receptor", J. Biol. Chem. vol. 264(30):18011-8 (1989).
Alfthan et al., "Properties of a single-chain antibody containing different linker peptides ," Protein Eng., 1995, 8:725-731.
Andrade et al., "Solid-phase oligosaccharide synthesis: preparation of complex structures using a novel linker and different glycosylating agents", Org Lett. 1 (11):1811-4 (1999).
Anthony et al., "A Recombinant IgG Fc That Recapitulates the Antiinflammatory Activity of Ivig," Science, Apr. 2008, 320(5874):373-376.
Anthony et al., "Identification of a receptor required for the anti-inflammatory activity of IVIG." Proc Natl Acad Sci USA. 105(50):19571-8 (2008).
Anthony et al., "Intravenous gammaglobulin suppresses inflammation through a novel TH2 pathway." Nature. 475(7354):110-3 (2011) (5 pages).
Anthony et al., "Novel roles for the lgG Fe glycan," Ann NY Acad Sci. 1253(2012):170-80 (2012).
Anthony et al., "Recapitulation of IVIG anit-inflammatory activity with a recombinant IgG Fe." Science. 320(5874):373-6 (2008).
Anthony et al., "Supporting Online Material for Recapitulation of IVIG anti-inflammatory activity with a recombinant laG Fe," Science. 320: 9 pages (2008).
Anthony et al., "A novel role for the lgG Fe glycan: the anti-inflammatory activity of sialylated lgG Fcs," J Clin Immunol. 30(Suppl 1):9-14 (2010).
Anumula, "Advances in fluorescence derivatization methods for high-performance liquid chromatoqraphic analysis of glycoprotein carbohydrates", Anal Biochem. 350(1):1-23 (2006).
Anumula, "Quantitative glycan profiling of normal human plasma derived immunoglobulin and its fragments Fab and Fc," J. Immunol. Methods., 2012, 382:167-176.
Arnold et al., "Human Serum IgM Glycosylation: Identification of Glycoforms That Can Bind to Mannan-Binding Lectin," J. Biol. Chem., 2005, 280:29080-29087.
Arumugam et al., "Intravenous immunoglobulin (IVIG) protects the brain against experimental stroke by preventing complement-mediated neuronal cell death," Procd Natl Acd Sci., 2007, 104(35):14101-14109.
Baker et al., "Metabolic control of recombinant protein N-glycan processing in NSO and CHO cells", Biotechnol Bioeng. 73(3):188-202 (2001).
Barb et al., "Branch specific sialylation of lgG-Fc Glycans by ST6Gal-I." Biochemistry. 48(41):9705-7 (2009) (6 paqes).
Barb et al., "NMR characterization of immunoglobulin G Fe glycan motion on enzymatic sialylation." Biochemistry. 51 (22):4618-26 (2012).
Barb et al., Supporting Information for "Branch specific sialylation of lgG-Fc Glycans by ST6Gal-I," Biochemistry. 48(41):9705-7 (2009) (8 paaes).
Barsam et al., "Platelet production and platelet destruction: assessing mechanisms of treatment effect in immune thrombocytopenia", Blood, 2011, 117(21):5723-5732.
Becker et al., "Fucose: biosynthesis and biological function in mammals," Glycobiology, 13(7):41 R-53R (2003).
Bohm et al., "The role of sialic acid as a modulator of the anti-inflammatory activity of lgG," Semin lmmunopathol. 34(3):443-53 (2012).
Bohne et al., "SWEET—WWW-based rapid 30 construction of oligo- and polysaccharides," Bioinformatics. 15(9): 767-768 (1999).
Bollati-Fogolin et al., "Temperature reduction in cultures of hGM-CSF-expressing CHO cells: effect on productivity and product quality", Biotechnol Prog. 21 (1 ):17-21 (2005).
Bork et al., "Increasing the sialylation of therapeutic glycoproteins: The potential of the sialic acid biosynthetic pathway," J. Pharm. Sci, 2009, 98:3499-3508.
Bowman et al., "Biosynthesis of L-selectin ligands: sulfation of sialyl Lewis x-related oligosaccharides by a family of GlcNAc-6-sulfotransferases", Biochemistry. 40(18):5382-91 (2001).
Breidenbach et al., "Targeted metabolic labeling of yeast N-glycans with unnatural sugars," Proc Natl Acad Sci USA. 107(9):3988-93 (2010).
Brinkman et al., "Phage display of disulfide-stabilized Fv fragments," J Immunol Methods., 1995, 182:41-50.

(56) References Cited

OTHER PUBLICATIONS

Broschat et al., "Purification and characterization of GDP-D-mannose 4,6-dehydratase from porcine thyroid", Eur J Biochem. 153(2):397-401 (1985).
Cabrera et al., "Influence of culture conditions on the N-glycosylation of a monoclonal antibody specific for recombinant hepatitis B surface antigen", Biotechnol Appl Biochem. 41(Pt1 ):67-76 (2005).
Campbell et al., "Therapeutic Effect of IVIG on Inflammatory Arthritis in Mice is Dependent on the Fc Portion and Independent of Sialylation or Basophils," J of Immunology., Jun. 1, 2014, 192 (11) 5031-5038.
Candore et al., "Inflammation, Cytokines, Immune Response, Apolipoprotein E, Cholesterol, and Oxidative Stress in Alzheimer Disease: Therapeutic Implications," Rejuvenation Research, 2010, 13(2-3):301-313.
Carpenter et al., "Potential inaccurate quantitation and sizing of protein aggregates by size exclusion chromatography: Essential need to use orthogonal methods to assure the quality of therapeutic protein products," J. Pharm. Sci., 2010, 99:2200-2208.
CAS No. 9007-83-4, "γ-Globulins from human blood," retrieved Apr. 5, 2021, retrieved from URL <https://www.sigmaaldrich.com/catalog/product/sigma/g4386?lang=en&region=US>, 3 pages.
Chelius et al., "Formation of pyroglutamic acid from n-terminal glutamic acid in immunoglobulin gamma antibodies," Anal Chem. 78:2370-6 (2006).
Chen & Colley, "Minimal structural and glycosylation requirements for ST6Gal I activity and trafficking" Glycobiology, 2000, 10:531-538.
Chen et al., "Analysis of N-glycans from recombinant immunoglobulin G by on-line reversedphase high-performance liquid chromatography/mass spectrometry," Anal Biochem. 370:147-61 (2007).
Chen et al., "Effects of elevated ammonium on glycosylation gene expression in CHO cells," Metab Enq. 8(2):123-32 (2006).
Chen et al., "Gas-phase oligosaccharide nonreducing end (GONE) sequencing and structural analysis by reversed phase HPLC/mass spectrometry with polarity switching," J Am Soc Mass Spectrom. 20:1821-33 (2009).
Chen et al., "Independent Lec1A CHO glycosylation mutants arise from point mutations in Nacetylglucosaminyltransferase I that reduce affinity for both substrates. Molecular consequences based on the crystal structure of GlcNAc-TI", Biochemistry. 40(30):8765-72 (2001 ).
Chen et al., "T cell receptor signaling co-regulates multiple Golgi genes to enhance N-glycan branching," J Biol Chem. 284(47):32454-61 (2009).
Cheng, et al., "Trans-sialidase activity of Photobacterium damsela α2,6-sialyltransferase and its application in the synthesis of sialosides," Glycobiology, 2010, 20:260-268.
Chumsae et al., "Identification and localization of unpaired cysteine residues in monoclonal antibodies by fluorescence labeling and mass spectrometry," Anal Chem. 81 (15):6449-57 (2009).
Clark et al., "Gene-expression profiles for five key glycosylation genes for galactose-fed CHO cells expressing recombinant IL-4/13 cytokine trap", Biotechnol Bioeng. 90(5):568-77 (2005).
Coisne et al., "Cutting edge: Natalizumab blocks adhesion but not initial contact of human T cells to the blood-brain barrier in vivo in an animal model of multiple sclerosis," J Immunol., 2009, 182:5909-5913.
Communication pursuant to Article 94(3) EPC for European Application No. 13822833.3, dated Aug. 31, 2017 (7 pages).
Communication pursuant to Article 94(3) EPC for European Patent Application No. 14792116.7, dated Jul. 25, 2017 (6 pages).
Communication Pursuant to Article 94(3) in European Application No. 14792116.7, dated Mar. 12, 2018, 5 pages.
Communication Pursuant to Article 94(3) in European Application No. 13822833.3, dated Feb. 18, 2021, 4 pages.
Communication Pursuant to Article 94(3) in European Application No. 13822833.3, Jan. 21, 2020, 4 pages.
Communication Pursuant to Article 94(3) in European Application No. 13822833.3, Nov. 29, 2018, 4 pages.
Communication Pursuant to Article 94(3) in European Application No. 14792116.7, dated Dec. 17, 2018, 5 pages.
Communication Pursuant to Article 94(3) in European Application No. 14853244.3, dated Jan. 14, 2021, 5 pages.
Communication Pursuant to Article 94(3) in European Application No. 14853244.3, dated Jul. 19, 2019, 7 pages.
Cooper et al., "GlycoSuiteDB: a curated relational database of glycoprotein glycan structures and their biological sources. 2003 update", Nucleic Acids Res. 31 (1):511-3 (2003).
Cooper et al., "GlycoSuiteDB: a new curated relational database of glycoprotein glycan structures and their biological sources," Nucleic Acids Res. 29(1):332-5 (2001).
Cox et al., "Glycan optimization of a human monoclonal antibody in the aquatic plant Lemna minor", Nat Biotechnol. 24(12):1591-7 (2006).
Crowell et al., "Amino acid and manganese supplementation modulates the glycosylation state of erythropoietin in a CHO culture system", Biotechnol Bioeng. 96(3):538-549 (2007) (29 pages).
Cummings et al., "Antibodies and Lectins in Glycan Analysis." Essentials of Glycobiology. Varki A, Cumminas RD, Eska JD et al., 1-17 (2009).
Czajkowsky et al., "Fc-fusion proteins: new developments and future perspectives," EMBO Mol. Med, 2012, 4:1015-1028.
Debray et al., Glycoprotein Analysis: General Methods. Encyclopedia of Analytical Chemistry. John Wiley & Sons, 1-39 (2006).
Dick et al., "C-terminal lysine variants in fully human monoclonal antibodies: investigation of test methods and possible causes," Biotechnol Bioenq. 100(6):1132-43 (2008).
Donaldson et al., "The use of lectins to select subpopulations of insect cells", Biotechnol Bioeng. 64(5):616-9 (1999).
Dorka, Penny, Thesis: "Modelling Batch and Fed-Batch Mammalian Cell Cultures for Optimizing MAb Productivity," Master of Science, University of Waterloo, 2007 (197 pages).
Dos Santos et al., "Kinin B2 receptor regulates chemokines CCL2 and CCL5 expression and modulates leukocyte recruitment and pathology in experimental autoimmune encephalomyelitis (EAE) in mice," J Neuroinflammation., Nov. 2008, 5:49.
Drecktrah et al., "Inhibition of a Golgi complex lysophospholipid acyltransferase induces membrane tubule formation and retrograde trafficking," Mal Biol Cell. 14(8):3459-69 (2003).
Durandy et al. "Immunoglobulin replacement therapy in primary antibody deficiency 1-16, 19-48, 51-53 diseases—maximizing success," Int Arch Allergy Immunol., Feb. 15, 2005, 136(3):217-229.
Dwyer, "Manipulating the immune system with immune globulin," N Engl J Med. 326(2):107-16 (1992).
El Khoury et al., "Ccr2 deficiency impairs microglial accumulation and accelerates progression of Alzheimer-like disease," Nat Med., 2007, 13:432-438.
Engel et al., "Rec. ST6Gal-I variants to control enzymatic activity in processes of in vitro glycoengineering," BMC Proceedings, (Suppl 6):P110 (2013).
Extended European Search Report for European Application No. 13822833.3, dated Jun. 6, 2016 (9 pages).
Extended European Search Report for European Application No. 14792116. 7, dated Oct. 21, 2016 2016 (9 paqes).
Extended European Search Report for European Application No. 14798473.6, dated Oct. 13, 2016 (10 pages).
Extended European Search Report for European Application No. 14853244.3, mailed Jun. 8, 2017 (11 pages).
Extended European Search Report for European Application No. 20158041.2, dated Sep. 9, 2020 (9 pages).
Fareed, "S-9-10 synthetic and biotechnology derived glycomimetics. Impact on drug development", Abstract of 6th Proteoglycan Forum, Jun. 24, Hamamatsu, Japan (2000) (1 page).
Feasby et al., "Guidelines on the use of intravenous immune globulin for neurologic conditions," Transfus Med Rev. 21 (2 Suppl 1):S57-107 (2007).
Ferrara et al., "Modulation of therapeutic antibody effector functions by glycosylation engineering: influence of golgi enzyme localization domain and co-expression of heterologous beta1, 4-N-acetylglucosaminyltransferase III and golgi alpha-mannosidase II," Biotechnol Bioeng. 93(5):851-861 (2006).

(56) References Cited

OTHER PUBLICATIONS

Fitz et al., "Combined use of subtilisin and N-acetylneuraminic acid aldolase for the synthesis of a fluorescent sialic acid," J Org Chem. 59(26):8279-80 (1994).
Fleischer, "Mechanism of glycosylation in the Golgi apparatus," J Histochem Cytochem. 1 (8):1033-40 (1983).
Forno et al., "N- and O-linked carbohydrates and glycosylation site occupancy in combinant human granulocyte-macrophage colony-stimulating factor secreted by a Chinese hamster ovary cell line," Eur J Biochem. 271 (5):907-19 (2004).
Forrer et al., "Chip-based gel electrophoresis method for the quanitification of half-antibody species in IaG4 and their by- and degradation products," Anal Biochem. 334:81-8 (2004).
Fukuda et al., "Survival of recombinant erythropoietin in the circulation: the role of carbohydrates", Blood. 73(1):84-89 (1989).
Gajdos et al., "Intravenous Immunoglobulin for myasthenia gravis," Cochrane Database of Systematic Reviews, 2012, 12:1-30.
Gates et al., "Glycobiology Analysis Manual," <http://www.sigmaaldrich.com/lifescience/proteomics/post-translational-analysis/glycosylation/glycoprotein-analysis-manual.html>. retrieved on Nov. 23, 2016 (132 pages).
Gawlitzek et al., "Ammonium alters N-glycan structures of recombinant TNFR-IgG: degradative versus biosynthetic mechanisms", Biotechnol Bioeng. 68(6):637-46 (2000).
Gawlitzek et al., "Characterization of changes in the glycosylation pattern of recombinant proteins from BHK-21 cells due to different culture conditions", J Biotechnol. 42(2):117-131 (1995).
Gilar et al., "Characterization of glycoprotein digests with hydrophilic interaction chromatography and mass spectrometry." Anal Biochem. 417(1):80-8 (2011).
Goetze et al., "High-mannose glycans on the Fc region of therapeutic IgG antibodies increase serum clearance in humans," Glvcobioloqy. 21 (7):949-59 (2011).
Goldman et al., "Monitoring recombinant human interferon-gamma N-glycosylation during perfused fluidized-bed and stirred-tank batch culture of CHO cells", Biotechnol Bioeng. 60(5):596-607 (1998).
Greer, "Biosimilar developers face a reference-product dilemma," <http://license.icopyright.net/user/viewFreeUse.act?fuid=MTYwMTgONDk%3D>, retrieved on Apr. 9, 2012 (3 pages).
Griciuc et al., "Alzheimer's Disease Risk Gene CD33 Inhibits Microglial Uptake of Amyloid Beta," Neuron., 2013, 78:631-643.
Gu et al., "Improvement of interferon-gamma sialylation in Chinese hamster ovary cell culture by feeding of N-acetylmannosamine", Biotechnol Bioeng. 58(6):642-48 (1998).
Guhr et al., "Enrichment of Sialylated IgG by Lectin Fractionation Does Not Enhance the Efficacy of Immunoglobulin G in a Murine Model of Immune Thrombocytopenia," PLOS ONE., Jun. 2011, 6(6):e21246.
Hahn et al., "Intravenous immunoglobulin treatment in chronic inflammatory demyelinating polyneuropathy: A double-blind, placebo-controlled, cross-over study," Brain, Aug. 1996, 119:1067-1077.
Hallewell et al., "Genetically Engineered Polymers of Human CuZn Superoxide Dismutase Biochemistry and Serum Half-lives," J Biol Chem., 1989, 264:5260-5268.
Hara et al., "Determination of mono-O-acetylated N-acetylneuraminic acids in human and rat sera by fluorometric high-performance liquid chromatography," Anal Biochem. 179(1):162-6 (1989).
Hara et al., "Determination of mono-O-acetylated N-acetylneuraminic acids in human and rat sera by fluorometric high-performance liquid chromatography," Anal Biochem., 1989, 179(1):162-166.
Harn et al., "Biophysical Signatures of Monoclonal Antibodies," Current Trends in Monoclonal Antibody Development and Manufacturing, 2010, 229-246 (Abstract Only).
Hendrick et al., "Increased productivity of recombinant tissular plasminogen activator (t-PA) by butyrate and shift of temperature: a cell cycle phases analysis", Cytotechnology. 36(1-3):71-83 (2001).
Hewitt et al., "Solution and solid-support synthesis of a potential leishmaniasis carbohydrate vaccine", J Org Chem. 66(12):4233-43 (2001).

Hickman et al., "Microglial dysfunction and defective beta-amyloid clearance pathways in aging Alzheimer's disease mice," J Neuroscience., 2008, 28(33):8354-8360.
Hills et al., "Metabolic control of recombinant monoclonal antibody N-glycosylation in GS-NS0 cells," Biotechnol Bioenq. 75(2):239-51 (2001).
Hincal, "An introduction to safety issues in biosimilars/follow-on biopharmaceuticals," J Med CBR Def. 7 (2009) (18 pages).
Hirabayashi et al., "Separation technologies for glycomics", J Chromatog B Analyst Technol Biomed Life Sci. 771 (1-2):67-87 (2002) (Abstract Only) (2 pages).
Hoja-Lukowicz et al., "High-mannose-type oligosaccharides from human placental arylsulfatase A are core fucosylated as confirmed by MALDI MS", Glycobiology. 10(6):551-7(2000).
Hokke et al., "Sialylated carbohydrate chains of recombinant human glycoproteins expressed in Chinese hamster ovary cells contain traces of N-glycolylneuraminic acid," FEBS Lett. 275(1-2):9-14 (1990).
Hosoi et al., "Modulation of oligosaccharide structure of a pro-urokinase derivative (pro-UK delta GS1) by changing culture conditions of a lymphoblastoid cell line Namalwa KJM-1 adapted to serum-free medium," Cytotechnology. 19(2):125-35 (1996).
Hossler et al., "Systems analysis of N-glycan processing in mammalian cells," PLoS One. 2(8):e713 (2007) (17 pages).
Houde et al., "Characterization of IgG1 Conformation and Conformational Dynamics by Hydrogen/Deuterium Exchange Mass Spectrometry," Anal. Chem., 2009, 81:2644-2651.
Huang et al., "Chemoenzymatic Glycoengineering of intact IgG Antibodies for Gain of Functions," Journal of the American Chemical Society, Jul. 16, 2012, 134(29):12308-12318.
Imai-Nishiya et al., "Double knockdown of alpha1,6-fucosyltransferase (FUT8) and GDPmannose 4,6-dehydratase (GMO) in antibody-producing cells: a new strategy for generating fully non-fucosylated therapeutic antibodies with enhanced ADCC", BMC Biotechnol. 7:84 (2007) (13 pages).
Inouye & Inouye, "Up-promoter mutations in the lpp gene of *Escherichia coli*," Nucleic Acids Res., 1985, 13:3101-3109.
International Preliminary Report on Patentability for International Application No. PCT/US2019/055983, dated Apr. 22, 2021, 13 pages.
International Preliminary Report on Patentability for International Application No. PCT/US2013/052040, mailed Jun. 18, 2015 (13 pages).
International Preliminary Report on Patentability for International Application No. PCT/US2014/036413, dated Nov. 3, 2015 (25 pages).
International Preliminary Report on Patentability for International Application No. PCT/US2014/060363, issued Apr. 19, 2016 (6 pages).
International Preliminary Report on Patentability for International Parent Application No. PCT/US2014/037761, dated Nov. 17, 2015 (8 pages).
International Search Report and Written Opinion for International Application No. PCT/US13/52040, mailed Dec. 3, 2013 (23 pages).
International Search Report and Written Opinion for International Application No. PCT/US14/36413, mailed Nov. 21, 2014 (42 pages).
International Search Report and Written Opinion for International Application No. PCT/US14/60363, mailed Februarv 4, 2015 (14 pages).
International Search Report and Written Opinion for International Application No. PCT/US2014/037761, mailed Oct. 10, 2014 (17 pages).
International Search Report and Written Opinion for International Patent Application No. PCT/US2013/043786, mailed Jul. 3, 2014 (21 pages).
International Search Report and Written Opinion in International Application No. PCT/US2019/055983, dated Jan. 10, 2020, 16 pages.
International Search Report and Written Opinion in International Application No. PCT/US2019/055987, dated Februarv 20, 2020, 14 pages.

(56) References Cited

OTHER PUBLICATIONS

Jabs et al., "Fast and Extensive Mass Spectrometry Characterization of Theraputic mAbs: The Panitumumab Case Study," CASSS Mass Spec Meeting, Poster 125 (2012) (1 page).

Jain et al., "Alpha4beta1 integrin mediates the recruitment of immature dendritic cells across the blood-brain barrier during experimental autoimmune encephalomyelitis," J Immunol., 2010, 184(12):7196-7206.

Janke and Jong., "Impact of IVIg on the interaction between activated T cells and microglia," Neural Res., 2006, 28:270-274.

Jefferis et al., "IgG-Fc-mediated effector functions: molecular definition of interaction sites for effector ligands and the role of glycosylation," Immunol. Rev., 1998, 163:59-76.

Jefferis, "Glycosylation as a strategy to improve antibody-based therapeutics," Nature Reviews, 2009, 8:226-234.

Johnson et al., "Cation exchange-HPLC and mass spectrometry reveal C-terminal amidation of an IgG1 heavy chain," Anal. Biochem., 2007, 360:75-83.

Joosten et al., "Effect of culture conditions on the degree of sialylation of a recombinant glycoprotein expressed in insect cells", Biotechnol Proq. 19(3):739-49 (2003).

Joziasse et al., "Branch specificity of bovine colostrum CMP-sialic acid: Gal beta 1-4GlcNAc-R alpha 2-6-sialyltransferase. Sialylation of bi-, tri-, and tetraantennary oligosaccharides and qlycopeptides of the N-acetyllactosamine type," J Biol Chem. 262(5):2025-33 (1987).

Kakehi et al., "Analysis of glycoproteins, glycopeptides and glycoprotein-derived oligosaccharides by high-performance capillary electrophoresis," J Chromatogr. 720(1-2):377-93 (1996).

Kalodiki et al., "New and generic anticoagulants and biosimilars: safety considerations," Clin Appl Thromb Hemost. 17(2):136-9 (2011) (5 pages).

Kanda et al., "Comparison of biological activity among nonfucosylated therapeutic IgG1 antibodies with three different N-linked Fc oligosaccharides: the high-mannose, hybrid, and complex types," Glycobiology. 17(1):104-18 (2006).

Kanda et al., "Establishment of a GDP-mannose 4,6-dehydratase (GMO) knockout host cell line: A new strategy for generating completely non-fucosylated recombinant therapeutics," Journal of Biotechnol. 130(3):300-10 (2007) (Abstract Only).

Kaneko et al., "Anti-inflammatory activity of immunoglobulin G resulting from Fc sialylation." Science. 313(5787):670-3 (2006).

Kaneko et al., "Pathology and protection in nephrotoxic nephritis is determined by selective engagement of specific Fc receptors." J Exp Med. 203(3):789-97 (2006).

Kasermann et al., "Analysis and Functional Consequences of Increased Fab-Sialylation of Intravenous Immunoglobulin (IVIG) after Lectin Fractionation," PLOS ONE, Jun. 2012, 7(6):e37243 (With Supplemental Material).

Kawashima et al., "Tyrosine kinase activity of epidermal growth factor receptor is regulated by GM3 binding through carbohydrate to carbohydrate interactions," J Biol Chem. 284(10):6147-55 (2009).

Keiser et al., "Direct isolation and sequencing of specific protein-binding glycosaminoglycans," Nat Med. 7(1):123-8 (2001).

Keppler et al., "Biosynthetic modulation of sialic acid-dependent virus-receptor interactions of two primate polyoma viruses," J Biol Chem. 270(3):1308-14 (1995).

Kile et al., "IVIG treatment of mild cognitive impairment due to Alzheimer's disease: a randomised double-blinded exploratory study of the effect on brain atrophy, cognition and conversion to dementia," J Neurol Neurosurg Psychiatry, Sep. 2015, 0: 1-7.

Kim et al., "Production and N-glycan analysis of secreted human erythropoietin glycoprotein in stably transfected *Drosophila* S2 cells," Biotechnol Bioeng. 92(4):452-61 (2005).

Kosa et al., "Modification of cell surfaces by enzymatic introduction of special sialic acid analogues," Biochem Biophys Res Commun. 190(3):914-20 (1993).

Krapp et al., "Structural analysis of human IgG-Fc glycoforms reveals a correlation between glycosylation and structural integrity," J Mol Biol. 325(5):979-89 (2003).

Kunkel et al., "Comparisons of the glycosylation of a monoclonal antibody produced under nominally identical cell culture conditions in two different bioreactors," Biotechnol Prog. 16(3):462-70 (2000).

Kunkel et al., "Dissolved oxygen concentration in serum-free continuous culture affects N-linked glycosylation of a monoclonal antibody," J Biotechnol. 62(1):55-71 (1998).

Kuter et al., "Thrombopoietin and platelet production in chronic immune thrombocytopenia," Hematol Oncol Clin North Am., Dec. 2009, 23(6):1193-1211.

Kuwano et al., Successful Treatment of Dermatomyositis with High-dose Intravenous Immunoglobulin, Acta Dermato-Venereologica, 2006, 86(2):158-159.

Lance et al., "Isolation and characterization of a partial cDNA for a human sialyltransferase." Biochem Biophys Res Commun. 164(1):225-32 (1989).

Lapointe et al., "IVIg therapy in brain inflammation: etiology-dependent differential effects on leucocyte recruitment," Brain, 2004, 127(Pt 12):2649-2656.

Lattova et al., "Alterations in glycopeptides associated with herceptin treatment of human breast carcinoma MCF-7 and T-lymphoblastoid cells," Mol Cell Proteomics. 10(9):M111.007765 (2011) (11 pages).

Le Floch et al., "HPCE monitoring of the N-glycosylation pattern and sialylation of murine erythropoietin produced by CHO cells in batch processes," Biotechnol Prog. 20(3):864-71 (2004).

Legaigneur, et al., "Exploring the acceptor substrate recognition of the human beta-Galactoside alpha2,6-Sialyltransferase," J. Biol. Chem., 2001, 276:21608-617.

Lifely et al., "Glycosylation and biological activity of CAMPATH-1 H expressed in different cell lines and grown under different culture conditions," Glycobiology. 5(8):813-22 (1995).

Lin et al., "Unusual stereoselectivity in sialic acid aldolase-catalyzed aldol condensations: synthesis of both enantiomers of high-carbon monosaccharides," J Am Chem Soc. 114(26):10138-45 (1992).

Lipscomb et al., "Effect of production method and gene amplification on the glycosylation pattern of a secreted reporter protein in CHO cells," Biotechnol Prog. 21 (1):40-9 (2005).

Live et al., "Conformational influences of glycosylation of a peptide: a possible model for the effect of glycosylation on the rate of protein folding," Proc Natl Acad Sci USA. 93(23):12759-61 (1996).

Logan & Shenk, "Adenovirus tripartite leader sequence enhances translation of mRNAs late after infection," Proc Natl Acad Sci USA., 1984, 81:355-359.

Lopez-Avalos et al., "The UDPase activity of the Kluyveromyces lactis Golgi GDPase has a role in uridine nucleotide sugar transport into Golgi vesicles," Glycobiology. 11 (5):413-22 (2001).

Ma, et al., "Two naturally occuring alpha2,6-Sialyltransferase forms with a single amino acid change in the catalytic domain differ in their catalytic activity and proteolytic processing," J. Biol. Chem., 1997, 272:672-279.

Macmillan et al., "Selective in vitro glycosylation of recombinant proteins: semi-synthesis of novel homogeneous glycoforms of human erythropoietin," Chem Biol. 8(2):133-45 (2001).

Mattu et al., "The Glycosylation and Structure of Human Serum IgA1, Fab, and Fc Regions and the Role of N-Glycosylation on Fcα Receptor Interactions," J. Biol. Chem., 1998, 273:2260-2272.

Miller et al., "Characterization of site-specific glycation during process development of a human therapeutic monoclonal antibody," J Pharm Sci. 100(7):2543-50 (2011).

Misra, "Are biosimilars really generics?" Expert Opin Biol Ther. 10(4):489-94 (2010).

Moran et al., "A systematic approach to the validation of process control parameters for monoclonal antibody production in fed-batch culture of a murine myeloma," Biotechnol Bioeng. 69(3):242-55 (2000).

Morrison, "Transfectomas provide novel chimeric antibodies," Science, 1985, 229(4719):1202-1207.

Mueller et al., "Recombinant glycoprotein product quality in proliferation-controlled BHK-21 cells," Biotechnol Bioeng. 65(5):529-36 (1999).

(56) References Cited

OTHER PUBLICATIONS

Naert et al., "CC chemokine receptor 2 deficiency aggravates cognitive impairments and amyloid pathology in a transgenic mouse model of Alzheimer's disease," J Neuroscience., 2011, 31(16):6208-6220.
Nairn et al., "Regulation of glycan structures in animal tissues: transcript profiling of glycanrelated genes," J Biol Chem. 283(25):17298-313 (2008).
Nam et al., "The effects of culture conditions on the glycosylation of secreted human placental alkaline phosphatase produced in Chinese hamster ovary cells," Biotechnol Bioeng. 100(6):1178-92 (2008).
Nettleton et al., "Role of Glycosylation Sites in the IgE Fc Molecule," Int. Arch. Allergy Immunol., 1995, 107:328-329.
Nimmerjahn et al., "The antiinflammatory activity of IgG: the intravenous IgG paradox," J Exp Med. 204(1 ):11-5 (2007).
Nishitsuji et al., "Apolipoprotein E regulates the integrity of tight junctions in an isoform-dependent manner in an in vitro blood-brain barrier model," J Biol Chem., 2011, 286(20):17536-17542.
Nowicki, "Basic facts about biosimilars," Kidney Blood Press Res. 30:267-72 (2007).
Nyberg et al., "Metabolic effects on recombinant interferon-gamma glycosylation in continuous culture of Chinese hamster ovary cells," Biotechnol Bioeng. 62(3):336-47 (1999).
Oh et al., "Effect of N-acetylcystein on butyrate-treated Chinese hamster ovary cells to improve the production of recombinant human interferon-beta-1 a," Biotechnol Prog. 21 (4):1154-64 (2005).
Pace et al., "Characterization of minor N-linked glycans on antibodies using endo H release and MALDI-mass spectrometry," Anal Lett. 42:1711-24 (2009).
Park et al., "Expression of carbamoyl phosphate synthetase I and ornithine transcarbamoylase genes in Chinese hamster ovary dhfr-cells decreases accumulation of ammonium ion in culture media," J Biotechnol. 81 (2-3):129-40 (2000).
Parmley, Sweetenina Immunoalobulins. Biocenturv Innovations. Bernstein (2015)(2 paaes).
Pekar and Sukumar, "Quantitation of aggregates in therapeutic proteins using sedimentation velocity analytical ultracentrifugation: practical considerations that affect precision and accuracy," Anal. Biochem., 2007, 367:225-237.
Plante et al., "Automated solid-phase synthesis of oligosaccharides," Science. 291 (5508):1523-7 (2001).
Plante et al., "Formation of beta-glucosamine and beta-mannose linkages using glycosyl phosphates," Org Lett. 2(24):3841-3 (2000).
Puli et al., "Effects of human intravenous immunoglobulin on amyloid pathology and neuroinflammation in a mouse model of Alzheimer's disease," J Neuroinflammation., 2012, 9:105.
Rader, "Nomenclature of new biosimilars will be highly controversial," BioProcess International. 9:28-32 (2011).
Raju, "Terminal sugars of Fc glycans influence antibody effector functions of IgGs," Curr Opin Immunol. 20(4):471-8 (2008).
Ramakrishna et al., Passively Administered Pooled Human Immunoglobulins Exert IL-10 Dependent Anti-Inflammatory Effects that Protect against Fatal HSV Encephalitis., Jun. 2, 2011, 7(6):1-17.
Raymond et al., "Production of Highly Sialylated Monoclonal Antibodies," Biochemistry, Genetics and Molecular Bioloqv-Glvcosvlation. Stefana Petrescu, 397-418 (2012).
Reitman et al., "Mouse lymphoma cell lines resistant to pea lectin are defective in fucose metabolism", J Biol Chem. 255(20):9900-6 (1980).
Restelli et al., "The effect of dissolved oxygen on the production and the glycosylation profile of recombinant human erythropoietin produced from CHO cells", Biotechnol Bioeng. 94(3):481-94 (2006).
Ripka et al., "Two Chinese hamster ovary glycosylation mutants affected in the conversion of GDP-mannose to GDP-fucose," Arch Biochem Biophys. 249(2):533-45 (1986).
Ritzenthaler et al., "Reevaluation of the effects of brefeldin A on plant cells using tobacco Bright Yellow 2 cells expressing Golgi-targeted green fluorescent protein and COPI antisera," Plant Cell. 14(1):237-61 (2002).
Robinson et al., "Characterization of a recombinant antibody produced in the course of a high yield fed batch process," Biotechnol Bioeng. 44(6):727-35 (1994).
Rodriguez et al., "Enhanced production of monomeric interferon-beta by CHO cells through the control of culture conditions," Biotechnol Prog. 21(1):22-30 (2005).
Roger, "Biosimilars: current status and future directions," Expert Opin Biol Ther. 10(7):1011-8 (2010).
Rudiger et al., "Breaking the sugar code: six levels of affinity regulation in glycan-lectin interaction," Crackina the Suaar Code by Naviaatina the Glycospace. Germany, 11-28 (2011 ).
Ruisi et al., "Stability of measurement of the immature platelet fraction," Am J Hematol. 85(8):622-4 (2010).
Ruther et al., "Easy identification of cDNA clones," EMBO, 1983, 12:1791-1794.
Santell et al., "Aberrant metabolic sialylation of recombinant proteins expressed in Chinese hamster ovary cells in high productivity cultures," Biochem Biophys Res Commun. 258(1):132-7 (1999).
Sasaki et al., "Site-specific glycosylation of human recombinant erythropoietin: analysis of glycopeptides or peptides at each glycosylation site by fast atom bombardment mass spectrometry," Biochemistry. 27(23):8618-26 (1988).
Sazinsky et al., "Aglycosylated immunoglobulin G1 variants productively engage activating Fc receptors," Proc Natl Acad Sci USA., Dec. 23, 2008, 105(51):20167-20172.
Schellekens and Moore, "Clinical comparability and European biosimilar regulations," Nat Biotechnol, Jan. 2010, 28(1):28-31.
Schellekens, "Biosimilar therapeutics—what do we need to consider?" NDT Plus, 2009, 2(Suppl_1):i27-i36.
Schiestl et al., "Acceptable changes in quality attributes of glycosylated biopharmaceuticals." Nat Biotechnol. 29(4):310-2 (2011).
Schulz et al., "Mediators of galactose sensitivity in UDP-galactose 4'-epimerase-impaired mammalian cells," J Biol Chem. 280(14):13493-502 (2005).
Schuster et al., "Improved effector functions of a therapeutic monoclonal Lewis Y-specific antibody by glycoform engineering," Cancer Res. 65(17):7934-41 (2005).
Schwab et al., "Intravenous immunoglobulin therapy: how does IgG modulate the immune system?," Nat Rev Immunol. 13(3): 176-89 (2013).
Schwab et al., "IVI g-mediated amelioration of ITP in mice is dependent on sialic acid and SIGNR 1," Eur J Immunol., Jan. 26, 2012, 42:826-830.
Segal et al., "Introduction: bispecific antibodies," J Immunol Methods., 2001, 248:1-6.
Sekhon et al., "Biosimilars: an overview," Biosimilars. 2011 (1 ):1-11 (2011).
Senger et al., "Effect of shear stress on intrinsic CHO culture state and glycosylation of recombinant tissue-type plasminogen activator protein," Biotechnol Prog. 19(4):1199-209 (2003).
Serrato et al., "Heterogeneous conditions in dissolved oxygen affect N-glycosylation but not productivity of a monoclonal antibody in hybridoma cultures", Biotechnol Bioeng. 88(2):176-188 (2004).
Shames et al., "CMP-N-acetylneuraminic acid synthetase of *Escherichia coli*: high level expression, purification and use in the enzymatic synthesis of CMP-N-acetyneuraminic acid and CMP-neuraminic acid derivatives", Glycobiology. 1(2):187-191 (1991).
Shang et al., "Development and application of a robust N-glycan profiling method for heightened characterization of monoclonal antibodies and related glycoproteins," J Ph arm Sci. 103(7): 1967-78 (2014).
Sherman, Rachel E., "Biosimilar Biological Products". Biosimilar Guidance Webinar. Food and Drug Administration (2012) (22 pages).
Shinkawa et al., "The absence of fucose but not the presence of galactose or bisecting Nacetylglucosamine of human IgG1 complex-type oligosaccharides shows the critical role of enhancing antibody-dependent cellular cytotoxicity," J Biol Chem. 278(5):3466-73 (2003).
Siberil et al., "Intravenous immunoglobulins in autoimmune and inflammatory diseases: a mechanistic perspective." Ann NY Acad Sci. 1110:497-506 (2007).

(56) References Cited

OTHER PUBLICATIONS

Sokolowski et al., "Conformational analysis of biantennary glycans and molecular modeling of their complexes with lentil lectin", J Mal Graph Model. 15(1):37-42 (1997).
Sparks et al., "Synthesis of potential inhibitors of hemagglutination by Influenza virus: chemoenzymic preparation of N-5 analogs of N-acetylneuraminic acid", Tetrahedron. 49(1):1-12 (1993).
Spearman et al., "Production and glycosylation of recombinant beta-interferon in suspension and cytopore microcarrier cultures of CHO cells", Biotechnol Prog. 21 (1):31-9 (2005).
Srinivas et al., "Assessment of dose proportionality, absolute bioavailability, and immunogenicity response of CTLA41g (BMS-188667), a novel immunosuppressive agent, following subcutaneous and intravenous administration to rats," Pharm Res. 14(7) :911-6 (1997).
Srinivas et al., "Pharmacokinetics and pharmacodynamics of CTLA41g (BMS-188667), a novel immunosuooressive agent, in monkeys following multiple doses," J Pharm Sci. 85(1):1-4 (1996).
Stadlmann et al., "A close look at human IgG sialylation and subclass distribution after lectin fractionation," Proteomics, 2009, 9:4143-4153.
Stadlmann et al., "Analysis of immunoglobulin glycosylation by LC-ES I-MS of glycopeptides and oligosaccharides," Proteomics. 8:2858-71 (2008).
Stadlmann et al., "Analytical and Functional Aspects of Antibody Sialylation," J Clin Immunol., May 2010, 30(Suppl 1):S15-S19.
Sticher, et al., "Purification and characterization of alpha(2-6)-sialyltransferase from human liver," Blycoconjugate J., 1991, 8:45-54.
Sung et al., "Effect of sodium butyrate on the production, heterogeneity and biological activity of human thrombopoietin by recombinant Chinese hamster ovary cells," J Biotechnol. 112(3):323-35 (2004).
Takashima, "Characterization of Mouse Sialyltransferase Genes: Their Evolution and Diversity," Biosci. Biotech. & Biochem., 2008, 72(5):1155-1167.
Takeuchi et al., "Structures and functional roles of the sugar chains of human erythropoietins," Glycobiology. 1(4):337-346 (1991).
Tan et al., "Characterization and comparison of commercially available TNF receptor 2-Fc fusion protein products." Mabs. 4(6):761-74 (2012).
Third-Party Observation pursuant to Rule 114(2) EPC for European Patent Application No. 13796989.5, dated Jun. 22, 2016 (14 pages).
Townsend, "Chapter 5 Analysis of Glycoconjugates Using High-pH Anion-Exchange Chromatography," Journal of Chromatography Library, 1995, 58:181-209.
Tran et al., "Separation of carbohydrate-mediated microheterogeneity of recombinant human erythropoietin by free solution capillary electrophoresis. Effects of pH, buffer type and organic additives," J Chromatogr. 542(2):459-71 (1991).
Trombetta et al., "Glycoprotein reglucosylation and nucleotide sugar utilization in the secretory pathway: identification of a nucleoside diphosphatase in the endoplasmic reticulum," EMBO J. 18(12):3282-92 (1999).
Trummer et al., "Process parameter shifting: Part I. Effect of DOT, pH, and temperature on the performance of Epo-Fc expressing CHO cells cultivated in controlled batch bioreactors," Biotechnol Bioeng. 94(6):1033-44 (2006).
Tutt et al., "Trispecific F(ab')3 derivatives that use cooperative signaling via the TCR/CD3 complex and CD2 to activate and redirect resting cytotoxic T cells," J Immunol., 1991, 147:60-69 (Abstract Only).
Umana et al., "Engineered glycoforms of an antineuroblastoma IgG1 with optimized antibodydependent cellular cytotoxic activity," Nat Biotechnol. 17(2):176-80 (1999).
Van Berkel et al., "N-linked glycosylation is an important parameter for optimal selection of cell lines producing biopharmaceutical human IgG," Biotechnol Prag. 25(1):244-51 (2009).
Van Den Nieuwenhof et al., "Recombinant glycodelin carrying the same type of glycan structures as contraceptive glycodelin-A can be produced in human kidney 293 cells but not in Chinese hamster ovary cells," Eur J Biochem. 267(15):4753-62 (2000).
Van Heeke & Schuster, "Expression of Human Asparagine Synthetase in *Escherichia Coli*," J Biol Chem., 1989, 24:5503-5509.
Varki, "Radioactive tracer techniques in the sequencing of glycoprotein oligosaccharides," FASEB J. 5(2):226-35 (1991).
Venkataraman et al., "Sequencing complex polysaccharides," Science. 286(5439):537-42 (1999).
Von Der Lieth, "Expanding proteomics to glycobiology: biocomputing approaches understanding the function of sugar," Pacific Symposium on Biocomputing; Kauai, Hawaii (Abstract only) (2 pages) (2002).
Wang et al., "Characterization and comparison of disulfide linkages and scrambling patterns in therapeutic monoclonal antibodies: using LC-MS with electron transfer dissociation," Anal Chem. 83:3133-40 (2011).
Wang et al., "EDEM an ER quality control receptor," Nat Struct Biol. 10(5):319-21 (2003).
Ward et al., "Binding activities of a repertoire of single immunoglobulin variable domains secreted from *Escherichia coli*," Nature, 1989, 341:544-546.
Warrington et al., in Naturally Occurring Antibodies (NAbs), edited by Hans U. Lutz, copyright 2012 Landes Bioscience and Springer Science+Business Media.
Washburn et al., "Controlled tetra-Fe sialylation of IVlg results in a drug candidate with consistent enhanced anti-inflammatory activity," Proc Natl Acad Sci U.S.A. 112(11):E1297-306 (2015).
Watson et al., "Capillary electrophoretic separation of human recombinant erythropoietin (r-HuEPO) glycoforms," Anal Biochem. 210(2):389-93 (1993).
Watson et al., "Structure determination of the intact major sialylated oligosaccharide chains of recombinant human erythropoietin expressed in Chinese hamster ovary cells," Glycobiology. 4(2):227-37 (1994).
Webb et al., "Structural characterization of intact, branched oligosaccharides by high performance liquid chromatography and liquid secondary ion mass spectrometry," Anal Biochem. 169(2):337-49 (1988).
Weikert et al., "Engineering Chinese hamster ovary cells to maximize sialic acid content of recombinant glycoproteins," Nature Biotechnology, Nov. 1999, 17:1116-1121.
Weiner et al., "A sensitive enzyme immunoassay for the quantitation of human CTLA41g fusion protein in mouse serum: pharmacokinetic application to optimizing cell line selection," J Pharm Biomed Anal. 15(5):571-9 (1997).
Weinstein et al., "Primary structure of beta-galactoside alpha 2,6-sialyltransferase. Conversion of membrane-bound enzyme to soluble forms by cleavage of the NH2-terminal signal anchor," J Biol Chem., 1987, 262:17735-17743.
Widiapradja et al., "Intravenous immunoglobulin protects neurons against amyloid beta-peptide toxicity and ischemic stroke by attenuating multiple cell death pathways," J Neurochem., 2012, 122:321-332.
Wilson et al., "The structure of an antigenic determinant in a protein," Cell, 1984, 37(3):767-778 (Abstract Only).
Wong et al., "Impact of dynamic online fed-batch strategies on metabolism, productivity and Nglycosylation quality in CHO cell cultures," Biotechnol Bioeng. 89(2):164-77 (2005).
Wootla et al., "Polyclonal and monoclonal antibodies in clinic," Methods Mol Biol., Sep. 2013, (1060):79-110.
Wopereis et al., "Mechanisms in protein O-glycan biosynthesis and clinical and molecular aspects of protein O-glycan biosynthesis defects: a review," Clin Chem. 52(4):574-600 (2006).
Wormold et al., "Variations in oligosaccharide-protein interactions in immunoglobulin G determine the site-specific glycosylation profiles and modulate the dynamic motion of the Fc oligosaccharides," Biochemistry, 1997, 36(6):1370-1380.
Wright et al., "Effect of glycosylation on antibody function: implications for genetic engineering," Trends Biotech, 1997, 15:26-32.
Wright et al., "In vivo trafficking and catabolism of IgG1 antibodies with Fe associated carbohydrates of differing structure," Glycobiology. 10(12):1347-55 (2000).
Wuhrer et al., "Glycoproteomics based on tandem mass spectrometry of glycopeptides," J. Chromatogr. B., 2007, 849:115-128.

(56) References Cited

OTHER PUBLICATIONS

Xie et al., "Rapid comparison of a candidate biosimilar to an innovator monoclonal antibody with advanced liquid chromatography and mass spectrometry technologies," MAbs. 2(4):379-94 (2010).
Yan et al., "Analysis of post-translational modifications in recombinant monoclonal antibody IgG1 by reversed-phase liquid chromatography/mass spectrometry," J Chromatogr A. 1164(1-2):153-61 (2007).
Yang et al., "Achievement of high cell density and high antibody productivity by a controlled-fed perfusion bioreactor process," Biotechnol Bioeng. 69(1):74-82 (2000).
Yang et al., "Bio-basis function neural network for prediction of protease cleavage sites in proteins," IEEE Trans Neural Netw. 16(1):263-74 (2005).
Yang et al., "Effect of ammonia on the glycosylation of human recombinant erythropoietin in culture," Biotechnol Prog. 16(5):751-9 (2000).
Ye et al., "N-glycan branching requirement in neuronal and postnatal viability," Glycobiology. 14(6):547-58 (2004).
Yoon et al., "Effect of culture pH on erythropoietin production by Chinese hamster ovary cells grown in suspension at 32.5 and 37.0 degrees C," Biotechnol Bioeng. 89(3):345-56 (2005).
Yoon et al., "Effect of simultaneous application of stressful culture conditions on specific productivity and heterogeneity of erythropoietin in Chinese hamster ovary cells," Biotechnol Prog. 20(4):1293-6 (2004).
Yuen et al., "Relationships between the N-glycan structures and biological activities of recombinant human erythropoietins produced using different culture conditions and purification procedures," Br J Haematol. 121 (3):511-26 (2003).
Yuk et al., "Changes in the overall extent of protein glycosylation by Chinese hamster ovary cells over the course of batch culture", Biotechnol Appl Biochem. 36(Pt 2):133-40 (2002).
Yuk et al., "Glycosylation by Chinese hamster ovary cells in dolichol phosphate-supplemented cultures," Biotechnol Appl Biochem. 36(Pt 2):141-7 (2002).
Zhang et al. "Sialylated intravenous immunoglobulin suppress anti-ganglioside antibody mediated nerve injury," Exp Neurol., May 18, 2016, 282:49-55.
Zhang et al., "Glycoengineered Pichia produced anti-HER2 is comparable to trastuzumab in preclinical study." MAbs. 3(3): 289-98 (2011).
Zhang et al., "Quantitative analysis and process monitoring of site-specific glycosylation microheterogeneity in recombinant human interferon-gamma from Chinese hamster ovary cell culture by hydrophilic interaction chromatography," J Chromatogr B Bio med Sci Appl. 712(1-2):73-82 (1998).
U.S. Appl. No. 17/284,188, filed Apr. 9, 2021.
U.S. Appl. No. 14/416,869, filed Jan. 23, 2015.
U.S. Appl. No. 15/957,703, filed Apr. 19, 2018.
U.S. Appl. No. 17/508,026, filed Oct. 22, 2021.
U.S. Appl. No. 14/787,403, filed Oct. 27, 2015.
U.S. Appl. No. 15/954,146, filed Apr. 16, 2018.
U.S. Appl. No. 16/589,634, filed Oct. 1, 2019.
U.S. Appl. No. 17/033,452, filed Sep. 25, 2020.
U.S. Appl. No. 17/032,994, filed Sep. 25, 2020.
U.S. Appl. No. 17/100,428, filed Nov. 20, 2020.
U.S. Appl. No. 18/217,401, filed Jun. 30, 2023.
U.S. Appl. No. 18/218,535, filed Jul. 5, 2023.
U.S. Appl. No. 18/218,996, filed Jul. 6, 2023.
U.S. Appl. No. 15/028,917, filed Apr. 12, 2016.
U.S. Appl. No. 15/985,288, filed May 21, 2018.
U.S. Appl. No. 16/688,772, filed Nov. 19, 2019.
U.S. Appl. No. 18/136,803, filed Apr. 19, 2023.
U.S. Appl. No. 14/890,865, filed Nov. 12, 2015.
U.S. Appl. No. 16/671,595, filed Nov. 1, 2019.
U.S. Appl. No. 17/739,912, filed May 9, 2022.
U.S. Appl. No. 17/602,156, filed Oct. 7, 2021.
U.S. Appl. No. 17/925,999, filed Nov. 17, 2022.
U.S. Appl. No. 17/802,441, filed Aug. 25, 2022.
U.S. Appl. No. 17/926,102, filed Nov. 17, 2022.
U.S. Appl. No. 17/909,282, filed Sep. 2, 2022.
U.S. Appl. No. 18/022,069, filed Feb. 17, 2023.
U.S. Appl. No. 18/022,061, filed Feb. 17, 2023.
U.S. Appl. No. 10/037,378, filed May 17, 2023.
Alberts et al. "Molecular Biology of the Cell" Garland Publishing, Inc. 1994.
Alistair Rogers and Yves Gibon, "Enzyme Kinetics: Theory and Practice," Plant Metabolic Networks, 2009, Chapter 4, pp. 71-103.
Altschul, S. F., Gish, W., Miller, W., Myers, E. W., & Lipman, D. J. (1990). Basic local alignment search tool. Journal of Molecular Biology, 215(3), 403-410.
Anthony, R. M., & Nimmerjahn, F. (2011). The role of differential IgG glycosylation in the interaction of antibodies with FcγRs in vivo. Current Opinion in Organ Transplantation, 16(1), 7-14.
Arnold et al., "The impact of glycosylation on the biological function and structure of human immunoglobulins," Annu Rev Immunol., 2007, 25:21-50.
Arroyo et al., "Hyper-Sialylated IgG M254, an Innovative Therapeutic Candidate, Evaluated in Healthy Volunteers and in Patients with Immune Thrombocytopenia Purpura: Safety, Tolerability, Pharmacokinetics, and Pharmacodynamics," Blood, 2019, 134(Supplement 1):1090.
Ausubel, F. M., Brent, R., Kingston, R. E., Moore, D. D., Seidman, J. G., Smith, J. A., & Struhl, K. (Eds.). (2010). Current Protocols in Molecular Biology. John Wiley & Sons.
Ausubel, F. M., Brent, R., Kingston, R. E., Moore, D. D., Seidman, J. G., Smith, J. A., & Struhl, K. (Eds.). (1995). Current protocols in molecular biology. John Wiley & Sons, Inc.
Baxter International Inc. (2012, Jun. 25). Baxter announces FDA approval for Gammagard Liquid as a treatment for multifocal motor neuropathy. Retrieved from https://investor.baxter.com/investors/events-and-news/news/press-release-details/2012/Baxter-Announces-FDA-Approval-for-GAMMAGARD-LIQUID-as-a-Treatment-for-Multifocal-Motor-Neuropathy/default.aspx.
Beneduce et al., "Anti-inflammatory Activity of IgG-Fc," Curr Top Microbiol Immunol., 2019;423:35-62.
Benesova et al., "Affinity Interactions as a Tool for Protein Immobilization," In: Magdeldin S, editor. Affinity Chromatography: InTech. 2012;29-46.
Goh and Ng, "Impact of Host Cell Line Choice on Glycan Profile," Critical Reviews in Biotechnology 38(6):851-67 (2018).
Bril et al., "IGIV in Neurology - Evidence and Recommendations," Can J Neurol Sci., 1999, 26:139-152.
Brown et al., "Deoxygenated disaccharide analogs as specific inhibitors of beta 1,4- galactosyltransferase 1 and selectin-mediated tumor metastasis." J. Biol. Chem. 284:4952- 4959 (2009).
Burckhardt et al., "Immunoglobulin G subclass distribution in three human intravenous immunoglobulin preparations," Vox Sang., 1989, 57(1): 10-14.
Cai et al., "Ensuring the Biological Safety of Plasma-Derived Therapeutic Proteins: Detection, Inactivation, and Removal of Pathogens," BioDrugs 19(2):79-96 (2005).
CAS No. 9003-11-6, Block copolymer of ethylene oxide and propylene oxide, 0 Sigma-Aldrich, retrieved on Dec. 14, 2022, retrieved from URL <https://www.products.pcc.eu/en/cas-numbers/9003-11-6/?list type=list>, 6 pages.
Cats et al., "Correlates of outcome and response to IVIg in 88 patients with multifocal motor neuropathy," Neurology, Aug. 31, 2010, 75(9):818-825.
Chen, Rui et al. "Glycoproteomics analysis of human liver tissue by combination of multiple enzyme digestion and hydrazide chemistry." Journal of proteome research vol. 8,2 (2009): 651-61. doi:10.1021/pr8008012.
Chintalacharuvu et al., "Treatment of Collagen Induced Arthritis by Proteolytic Enzymes: Immunomodulatory and Disease Modifying Effects," J Rheumatology., Sep. 2001, 28(9):2049-2059.
Clark-Curtiss, J. E., & Curtiss, R. III. (1983). Analysis of recombinant DNA using Escherichia coli minicells. In R. Wu & L. Grossman (Eds.), Methods in Enzymology (vol. 101, pp. 347-362). Academic Press. https://doi.org/10.1016/0076-6879(83)01023-0.

(56) References Cited

OTHER PUBLICATIONS

Cohn, E. J., Oncley, J. L., Strong, L. E., Hughes, W. L. Jr., & Armstrong, S. H. Jr. (1944). Chemical, clinical, and immunological studies on the products of human plasma fractionation. I. The characterization of the protein fractions of human plasma. The Journal of Clinical Investigation, 23(4), 417-432. https://doi.org/10.1172/JCI101508.

Cohn, E. J., Strong, L. E., Hughes, W. L. Jr., Mulford, D. J., Ashworth, J. N., Melin, M., & Taylor, H. L. (1946). Preparation and properties of serum and plasma proteins. Iv. A system for the separation into fractions of the protein and lipoprotein components of biological tissues and fluids. Journal of the American Chemical Society, 68(3), 459-475. https://doi.org/10.1021/ja01207a034.

Court of Justice of the Andean Community. (n.d.). Intranet. comunidadandina.org [online]. Available No. later than Apr. 18, 2019. Retrieved Dec. 21, 2022, from https://intranet.comunidadandina.org.

Crow, Andrew R et al. "Mechanisms of action of intravenous immunoglobulin in the treatment of immune thrombocytopenia." Pediatric blood & cancer vol. 47,5 Suppl (2006): 710-3. doi:10.1002/pbc.20980.

Dalziel et al., "Lectin analysis of human immunoglobulin G N-glycan sialylation," Glycoconj J., Dec. 1999, 16(12):801-807.

Dizon-Maspat et al., "Singe Pass Tangential Flow Filtration to Debottleneck Downstream Processing for Therapeutic Antibody Production," Biotechnology and Bioengineering 109(4):962-970 (2012).

Dodel et al., Intravenous Immunoglobulins as a Treatment for Alzheimer's Disease, Drugs 2010; 70 (5): 513-528.

Donadio, S., Monciardini, P., & Sosio, M. (2003). Analysis of the biosynthetic gene cluster for the polyether antibiotic nanchangmycin. Biochemistry, 85(4), 311-321. https://doi.org/10.1046/j.1365-2958.2003.03571.x.

Dotz, V., Visconti, A., Lomax-Browne, H. J., Clerc, F., Hipgrave Ederveen, A. L., Medjeral- Thomas, N. R., Cook, H. T., Pickering, M. C., Wuhrer, M., & Falchi, M. (2021). O- and N- Glycosylation of serum immunoglobulin A is associated with IgA nephropathy and glomerular function. Journal of the American Society of Nephrology, 32(10), 2455-2465. https://doi.org/10.1681/ASN.2020081208.

Edelman, G M et al. "The covalent structure of an entire gammaG immunoglobulin molecule." Proceedings of the National Academy of Sciences of the United States of America vol. 63,1 (1969): 78-85. doi:10.1073/pnas.63.1.78.

Fernandez-Cruz et al., "6th International Immunoglobulin Symposium: poster presentations," Clin Exp Immunol., Dec. 2009, 158(Suppl 1):60-67.

Fokkink et al., "Immunoglobulin G Fc N-glycosylation in Guillain-Barre syndrome treated with intravenous immunoglobulin," Clinical and Experimental Immunology, Dec. 2014, 178(Suppl 1):105-107.

Frankish, "Lancet Asia Medical Forum-call for papers," The Lancet Neurology, Sep. 1, 2008, 7(9):P771.

Green & Sambrook, Molecular Cloning: A Laboratory Manual, Fourth Edition (2012) Cold Spring Harbor Laboratory Press, Cold Spring Harbor, N.Y.

Holland et al., "Differential glycosylation of polyclonal IgG, IgG-Fc and IgG-Fab isolated from the sera of patients with ANCA-associated systemic vasculitis," Biochimica et Biophysica Acta., Apr. 2006, 1760(4): 669-677.

Horowitz et al., "Strategies for Viral Inactivation," Current Opinion in Hematology 2(6):484- 92 (1995).

Hughes et al., "Intravenous immune globulin (10% caprylatechromatography purified) for the treatment of chronic inflammatory demyelinating polyradiculoneuropathy (ICE study): a randomised placebo-controlled trial," Lancet Neurol., 2008; 7:136-144.

Lijima et al., "Efficacy and availability of intravenous immunoglobulin in chronic inflammatory demyelinating polyneuropathy," Nihon Rinsho., Apr. 2012, 70(4):715-721 (English Abstract Only).

Imashuku, "High dose immunoglobulin (IVIG) may reduce the incidence of Langerhans cell histiocytosis (LCH)-associated central nervous system involvement," CNS Neurol Disord Drug Targets., Nov. 2009, 8(5):380-386 (EnglishAbstract Only).

International Preliminary Report on Patentability for International Parent Application No. PCT/US21/33150, dated Nov. 17, 2022 (6 pages).

International Preliminary Report on Patentability for International Parent Application No. PCT/US2020/028863, dated Jul. 20, 2020 (7 pages).

International Preliminary Report on Patentability for International Parent Application No. PCT/US2021/019607, dated Jun. 15, 2021 (10 pages).

International Preliminary Report on Patentability for International Parent Application No. PCT/US2021/033156, dated Nov. 2, 2021 (9 pages).

International Preliminary Report on Patentability for International Parent Application No. PCT/US2021/020898, dated Sep. 14, 2021 (8 pages).

International Preliminary Report on Patentability for International Parent Application No. PCT/US2021/057658, dated Feb. 4, 2022 (9 pages).

International Preliminary Report on Patentability for International Parent Application No. PCT/US2021/057659, dated Oct. 27, 2021 (8 pages).

International Preliminary Report on Patentability for International Parent Application No. PCT/US2021/060182, dated May 16, 2023 (7 pages).

International Search Report and Written Opinion in International Application No. PCT/US2021/019607, dated Jun. 15, 2021, 9 pages.

International Search Report and Written Opinion in International Application No. PCT/US2021/033156, dated Nov. 2, 2021, 8 pages.

International Search Report and Written Opinion in International Application No. PCT/US2021/020898, dated Sep. 14, 2021, 7 pages.

International Search Report and Written Opinion in International Application No. PCT/US2021/057658, dated Feb. 4, 2022, 8 pages.

International Search Report and Written Opinion in International Application No. PCT/US2021/057659, dated Oct. 27, 2021, 7 pages.

International Search Report and Written Opinion in International Application No. PCT/US2021/060182, dated May 27, 2022, 6 pages.

International Search Report and Written Opinion in International Application No. PCT/US2020/028863, dated Jul. 20, 2020, 11 pages.

International Search Report and Written Opinion for International Application No. PCT/US21/33150, mailed Oct. 5, 2021 (9 pages).

Jassal et al., "Sialylation of Human IgG-Fc Carbohydrate by Transfected Rat a2,6- Sialyltransferase," Biochemical and Biophysical Research Communications, 2001, 286:243-249.

Kightlinger et al., "Synthetic Glycobiology: Parts, Systems, and Applications," ACS Synth. Biol. 9:1534-62 (2020).

Klutz et al., "Continuous Viral Inactivation at low Ph Value in Antibody Manufacturing," Chemical Engineering and Processing: Process Intensification 102:88-11 (2016).

Kobata, "Function and pathology of the sugar chains of human immunoglobulin G," Glycobiology, 1990, 1(1):5-8.

Kriegler, M. (1990). Gene transfer and expression: A laboratory manual. W.H. Freeman and Company.

Kumpel et al., "Galactosylation of human IgG monoclonal anti-D produced by EBV- transformed Blymphoblastoid cell lines is dependent on culture method and affects Fc receptor-mediated functional activity," Hum Antibodies Hybridomas., 1994, 5(3-4): 143-151.

Kuhn, Bernd et al. "The structure of human a-2,6-sialyltransferase reveals the binding mode of complex glycans." Acta crystallographica. Section D, Biological crystallography vol. 69, Pt 9 (2013): 1826-38. doi:10.1107/S0907444913015412.

Kurnik, "Buffer Exchange Using Size Development, and Industrial Application," Biotechnology and Bioengineering 45(2): 149-58 (1995).

(56) References Cited

OTHER PUBLICATIONS

Leontyev et al., "Sialylation-independent mechanism involved in the amelioration of murine immune thrombocytopenia using intravenous gammaglobulin," Transfusion, Aug. 2012, 52(8):1799-805.

Liu et al., "Oriented Immobilization of Proteins on Solid Supports for Use in Biosensors and Biochips: a Review," Microchim Acta 2016; 183;1-19.

Lund et al., "Multiple Interactions of IgG with Its Core Oligosaccharide Can Modulate Recognition by Complement and Human Fcy Receptor I and Influence the Synthesis of Its Oligosaccharide Chains," J Immunol., 1996, 157:4963-4969.

Lundstrom et al., "Blood Plasma IgG Fc Glycans are Significantly Altered in Alzheimer's Disease and Progressive Mild Cognitive Impairment," Journal of Alzheimer's Disease, 2014, 38:567-579.

Malhotra et al., "Glycosylation changes of IgG associated with rheumatoid arthritis can activate complement via the mannose-binding protein," Nature Medicine, 1992, 1:237-243.

Manning, R. (2014, May 5). Embracing complexity: Understanding IVIg to rationally design novel therapeutics [Conference presentation]. PEGS Boston.

Mayya, Viveka et al. "Quantitative phosphoproteomic analysis of T cell receptor signaling reveals system-wide modulation of protein-protein interactions." Science signaling vol. 2,84 ra46. Aug. 18, 2009, doi:10.1126/scisignal.2000007.

Mazourov et al., "The Efficacy of systemic enzyme therapy in the treatment of rheumatoid arthritis," Int J Immunotherapy., 1997, XIII(3/4): 85-91.

Meldal and Schoffelen, "Recent Advances in Covalent, Site-Specific Protein Immobilization," F1000Research 216,5(F1000 Faculty Rev):2303.

Meyer et al., "Advances in DNA-Directed Immobilization," Curr Opin Chem Biol. 2014; 18:8- 15.

Mimura et al., "The influence of glycosylation on the thermal stability and effector function expression of human IgGl-Fc: properties of a series of truncated glycoforms," Molecular Immunology, 2000, 37(12-13):697-706.

Mohammad et al., "Nanofiltration Membranes Review: Recent Advances and Future Prospects," Desalination 356:226-54 (2015).

Morrison, D. A. (1977). Transformation in Escherichia coli: Cryogenic preservation of competent cells. Journal of Bacteriology, 132(1), 349-351. https://doi.org/10.1128/jb.132.1.349-351.1977.

National Center for Biotechnology Information (NCBI). (2007, Jul. 16). Substance record SID 24898182. PubChem. Retrieved Dec. 15, 2022, from https://pubchem.ncbi.nlm.nih.gov/substance/24898182 pages.

Negre, E., et al. (n.d.). Training continued for hospital pharmacists [Machine-translated document]. Available No. later than Apr. 18, 2019. Retrieved Dec. 21, 2022.

Nguyen et al., "Improved HCP Reduction Using a New, All-Synthetic Depth Filtration Media Within an Antibody Purification Process," Biotechnology Journal 14(1): 1700771 (2019).

Nimmerjahn et al., "Anti-Inflammatory Actions of Intravenous Immunoglobulin," Annual Review of Immunology, 2008, 26:513-533.

Ofosu et al., "Plasma-Derived Biological Medicines Used to Promote Haemostasis," Thromb Haemost 99:851-62 (2008).

Palva, I., Lehtovaara, P., Käariainen, L., Sibakov, M., Cantell, K., Schein, C. H., Kashiwagi, K., & Weissmann, C. (1983). Secretion of interferon by Bacillus subtilis. Gene, 22(3), 229- 235. https://doi.org/10.1016/0378-1119(83)90100-0.

Paulson, J. C., & Colley, K. J. (1989). Glycosyltransferases: Structure, localization, and control of cell type-specific glycosylation. Journal of Biological Chemistry, 264(30), 17615- 17618. https://doi.org/10.1016/S0021-9258(19)84926-6.

Radosevich, M., & Burnouf, T. (2010). Intravenous immunoglobulin G: Trends in production methods, quality control, and quality assurance. Vox Sanguinis, 98(1), 12-28. https://doi.org/10.1111/j.1423-0410.2009.01226.x.

Raju et al., "Glycoengineering of therapeutic glycoproteins: in vitro galactosylation and sialylation of glycoproteins with terminal N-acetylglucosamine and galactose residues," Biochemistry, Jul. 31, 2001, 40(30): 8868-8876.

Raju et al., "Species-specific variation in glycosylation of IgG: evidence for the species- specific sialylation and branch-specific galactosylation and importance for engineering recombinant glycoprotein therapeutics," Glycobiology, May 1, 2000, 10(5):477-486.

Ramakrishnan, Boopathy et al. "Structural snapshots of beta-1,4-galactosyltransferase-I along the kinetic pathway." Journal of molecular biology vol. 357,5 (2006): 1619-33. doi:10.1016/j.jmb.2006.01.088.

Ramasamy, Velavan et al. "Oligosaccharide preferences of beta1,4-galactosyltransferase-I: crystal structures of Met340His mutant of human beta1,4-galactosyltransferase-I with a pentasaccharide and trisaccharides of the N-glycan moiety." Journal of molecular biology vol. 353,1 (2005): 53-67. doi:10.1016/j.jmb.2005.07.050.

Ramos-de-la-Pena et al., "Protein A Chromatography: Challenges and Process in the Purification of Monoclonal Antibodies," Journal of Separation Science 2019:doi:10.1002/jssc.201800963.

Sambrook, Fritsch & Maniatis, Molecular Cloning: A Laboratory Manual, Third Edition (2001) Cold Spring Harbor Laboratory Press, Cold Spring Harbor, N.Y.

Samuelsson et al., "Anti-inflammatory activity of IVIG mediated through the inhibitory Fc receptor," Science, 2001, 291:484-486.

Sapsford et al., "Functionalizing Nanoparticles with Biological Molecules: Developing Chemistries that Facilitate Nanotechnology," Chem Rev. 2013;113(3)1904-2074.

Scallon et al., "Higher levels of sialylated Fc glycans in immunoglobulin G molecules can adversely impact functionality," Mol Immunol., 2007, 44(7):524-1534.

Scielo.org.ve. (2006, December). Fronesis. Retrieved Feb. 10, 2023, from http://www.scielo.org.ve/scielo.php?script=sci_arttext&pid=S1315- 62682006000300002&Ing=es&nrm=iso.

Smith, T. F., & Waterman, M. S. (1981). Identification of common molecular subsequences. Journal of Molecular Biology, 147(1), 195-197. https://doi.org/10.1016/0022- 2836(81)90087-5.

Steen et al., "Protein Engineering for Directed Immobilization," Bioconjug Chem. 2013;24(11):1761-77.

Sudo et al., "Different IVIG Glycoforms Affect In Vitro Inhibition of Anti-Ganglioside Antibody-Mediated 75*Complement Deposition," Plos One, 2014, 9(9):e107772.

Sutherland, "Filtration Overview: A Closer Look at Depth Filtration," Filtration and Separation 45(8)25-28 (2008).

Trilling et al., "Antibody Orientation on Biosensor Surfaces: a Minireview," Analyst 2013;138(6):1619-27.

Wang et al., "Antibody structure, instability, and formulation," Journal of Pharmaceutical Sciences, Jan. 2007, 96(1):1-26.

Wang, "Instability, stabilization, and formulation of liquid protein pharmaceuticals," International Journal of Pharmaceutics, Aug. 1999, 185(2): 129-188.

Warne, "Development of high concentration protein biopharmaceuticals: The use of platform approaches in formulation development," European Journal of Pharmaceutics and Biopharmaceutics, Jun. 2011, 78(2):208-212.

Washburn et al., "High-resolution physicochemical characterization of different intravenous immunoglobulin products," Plos One, 2017, 12(7):e0181251.

Wikipedia contributors. (n.d.). Medicine. Wikipedia. Retrieved Dec. 21, 2022, from https://es.wikipedia.org/wiki/Medicamento.

Wong et al., "Sialylated IgG-Fc: a novel biomarker of chronic inflammatory demyelinating polyneuropathy," J Neurol Neurosurg Psychiatry., 2016, 87:275-279.

Zufferey et al., "Woodchuck Hepatitis Virus Posttranscriptional Regulatory Element Enhances Expression of Transgenes Delivered by Retroviral Vectors," Journal of Virology 73(4): 2886-92 (1999).

\* cited by examiner

SEQ ID NO:1

GSYYDSFKLQTKEFQVLKSLGKLAMGSDSQSVSSSSTQDPHRGRQTLGSLRGLAKAKPEASFQV
WNKDSSSKNLIPRLQKIWKNYLSMNKYKVSYKGPGPGIKFSAEALRCHLRDHVNVSMVEVTDFP
FNTSEWEGYLPKESIRTKAGPWGRCAVVSSAGSLKSSQLGREIDDHDAVLRFNGAPTANFQQDV
GTKTTIRLMNSQLVTTEKRFLKDSLYNEGILIVWDPSVYHSDIPKWYQNPDYNFFNNYKTYRKL
HPNQPFYILKPQMPWELWDILQEISPEEIQPNPPSSGMLGIIIMMTLCDQVDIYEFLPSKRKTD
VCYYYQKFFDSACTMGAYHPLLYEKNLVKHLNQGTDEDIYLLGKATLPGFRTIHC

Fig. 3A

SEQ ID NO:2

MIHTNLKKKFSYFILAFLLFALICVWKKGSYEALKLQAKEFQVTKSLEKLAIGSGSQSTSASIK
QDSKPGSQVLSHLRVTAKVKPQSPYQVWDKNSSSKNLNPRLQKILKNYLSMNKYKVSYKGPGPG
VKFSVEALRCHLRDRVNVSMIEATDFPFNTTEWEGYLPKENFRTKAGPWHRCAVVSSAGSLKSS
HLGKEIDSHDAVLRFNGAPVADFQQDVGMKTTIRLMNSQLITTEKQFLKDSLYNEGILIVWDPS
LYHADIPNWYKKPDYNFFETYKSYRKLYPSQPFYILRPQMPWELWDIIQEIAPDRIQPNPPSSG
MLGIIIMMTLCDQVDVYEFLPSKRKTDVCYYHQKFFDSACTMGAYHPLLFEKNMVKQLNEGTDE
DIYIFGKATLSGFRTIHC

Fig. 3B

SEQ ID NO:3

MTRLTVLALLAGLLASSRAGSSPLLAMEWSHPQFEKLEGGGSGGGSGGSWSHPQFEKHAHAHSR
KDHLIHNVHKEEHAHAHNKELGTAVFQGPMRRAIRGRSFQVWNKDSSSKNLIPRLQKIWKNYLS
MNKYKVSYKGPGPGIKFSAEALRCHLRDHVNVSMVEVTDFPFNTSEWEGYLPKESIRTKAGPWG
RCAVVSSAGSLKSSQLGREIDDHDAVLRFNGAPTANFQQDVGTKTTIRLMNSQLVTTEKRFLKD
SLYNEGILIVWDPSVYHSDIPKWYQNPDYNFFNNYKTYRKLHPNQPFYILKPQMPWELWDILQE
ISPEEIQPNPPSSGMLGIIIMMTLCDQVDIYEFLPSKRKTDVCYYYQKFFDSACTMGAYHPLLY
EKNLVKHLNQGTDEDIYLLGKATLPGFRTIHCPG

Fig. 3C

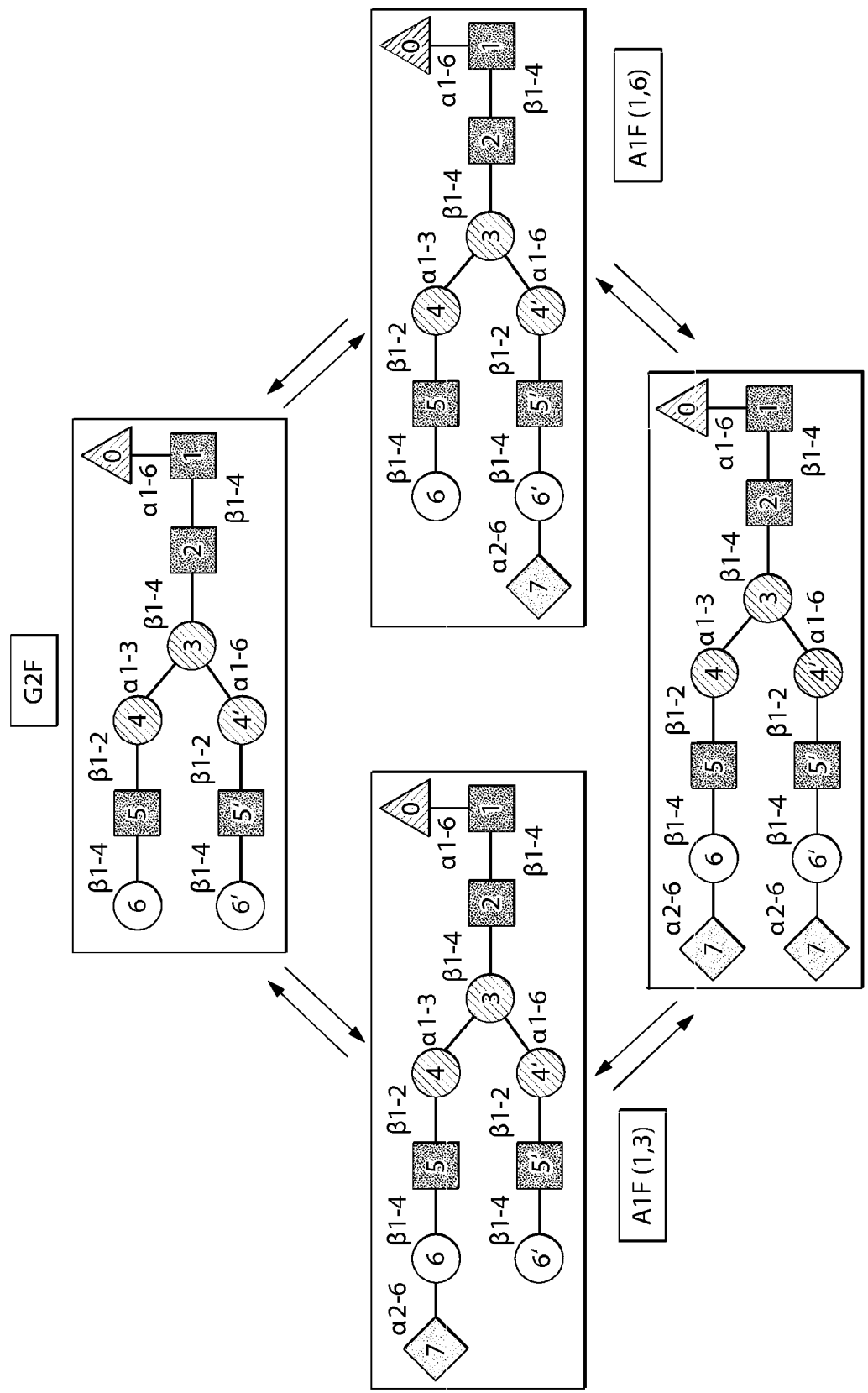

METHODS FOR THE TREATMENT OF NEURODEGENERATION

CROSS-REFERENCE TO RELATED APPLICATIONS

This application is a continuation application of U.S. application Ser. No. 16/671,595, filed Nov. 1, 2019, which is a continuation application of U.S. application Ser. No. 14/890,865, filed Nov. 12, 2015, which is a U.S. National Phase Application pursuant to 35 U.S.C. § 371 of International Application No. PCT/US2014/037761 filed May 13, 2014, which claims benefit of U.S. Provisional Application No. 61/822,798, filed May 13, 2013, which is hereby incorporated by reference in its entirety.

SEQUENCE LISTING

This application contains a Sequence Listing that has been submitted electronically as an ASCII text file named "Sequence_Listing.txt." The ASCII text file, created on May 5, 2022, is 11 kilobytes in size. The material in the ASCII text file is hereby incorporated by reference in its entirety.

BACKGROUND OF THE INVENTION

Therapeutic polypeptides are an important class of therapeutic biotechnology products, and therapeutic Fc containing polypeptides, such as IVIG, Fc-receptor fusions, and antibodies (including murine, chimeric, humanized and human antibodies and fragments thereof) account for the majority of therapeutic biologic products.

Alzheimer disease (AD) is an age-related disease involving neurodegeneration that results in progressive loss of cognitive function. Five medications are currently used to treat the cognitive manifestations of AD: four are acetylcholinesterase inhibitors (tacrine, rivastigmine, galantamine and donepezil) and the other (memantine) is an NMDA receptor antagonist.

SUMMARY OF THE INVENTION

The invention encompasses the discovery that Fc-containing polypeptides that include branched glycans and that are sialylated on the branched glycan (e.g., on an α 1,3 and/or α 1,6 arm in the Fc region's N-linked glycosylation site), with, e.g., a NeuAc-α 2,6-Gal or NeuAc-α 2,3-Gal terminal linkage, are useful in treating neurodegeneration, e.g., in the treatment of neurodegenerative diseases such as Alzheimer's Disease. The present disclosure provides, in part, methods for treating neurodegeneration or neurodegenerative diseases by administering compositions containing such Fc-containing polypeptides as well as methods for evaluating, identifying, and/or producing (e.g., manufacturing) such polypeptides for the treatment of neurodegeneration.

In the first aspect, the invention features a method for the treatment of neurodegeneration. The method includes administering (e.g., to a subject in need thereof) a preparation that includes polypeptides having an Fc region (e.g., an Fc region of IgA, IgD, IgE, IgG, or IgM) wherein at least 10% (e.g., at least 15%, 20%, 25%, 30%, 35%, 40%, 45%, 50%, 55%, 60%, 65%, 70%, 75%, 80%, 85%, 90%, 95%, up to and including 100%) of the branched glycans (e.g., on the Fc region) have at least one galactose connected to a respective terminal sialic acid (i.e., are sialylated).

In certain embodiments, the branched glycans (e.g., at least 10%, 15%, 20%, 25%, 30%, 35%, 40%, 45%, 50%, 55%, 60%, 65%, 70%, 75%, 80%, 85%, 90%, 95%, up to and including 100%) are sialylated on an α 1,3 arm of the branched glycan (e.g., by way of a NeuAc-α 2,6-Gal and/or a NeuAc-α 2,3-Gal terminal linkage).

In some embodiments, the polypeptides are derived from IVIG (e.g., sialylated IgGs purified or enriched from IVIG; modified (e.g., enzymatically sialylated) IVIG; or Fc regions produced from IVIG). In other embodiments, the polypeptides are Fc regions derived from IVIG (e.g., papain digested and sialylated).

In certain embodiments, the preparation includes recombinant polypeptides having an Fc region (e.g., an Fc region of IgA, IgD, IgE, IgG, or IgM) wherein at least 10% (e.g., at least 15%, 20%, 25%, 30%, 35%, 40%, 45%, 50%, 55%, 60%, 65%, 70%, 75%, 80%, 85%, 90%, 95%, up to and including 100%) of the branched glycans (e.g., on the Fc region) have at least one galactose connected to a respective terminal sialic acid (i.e., are sialylated).

In certain embodiments of any of the foregoing methods, the polypeptides include an IgG Fab region that is or is not sialylated.

In other embodiments, the polypeptides are Fc regions (e.g., recombinant Fc regions) or Fc-region-containing (e.g., recombinant Fc-region-containing) polypeptides.

In further embodiments of any of the foregoing methods, the polypeptides are administered in a pharmaceutical formulation (e.g., including a pharmaceutically acceptable carrier or diluents).

In another aspect, the invention features a method of manufacturing a pharmaceutical product for the treatment of neurodegeneration. This method includes: providing a sample of a test preparation including polypeptides (e.g., polypeptides having an Fc region); determining the percent of branched glycans (e.g., on the Fc regions) of the polypeptides that possess a galactose moiety connected to a terminal sialic acid; and processing the test preparation into a pharmaceutical product for the treatment of neurodegeneration if the percent of branched glycans (e.g., on the Fc regions) of the polypeptides is greater than 10% (e.g., greater than 15%, 20%, 25%, 30%, 35%, 40%, 45%, 50%, 55%, 60%, 65%, 70%, 75%, 80%, 85%, 90%, 95%, up to and including 100%), thereby manufacturing a pharmaceutical product for the treatment of neurodegeneration.

In a further embodiment, the invention features another method of manufacturing a pharmaceutical product. This method includes: providing a sample of a test preparation including polypeptides (e.g., polypeptides having an Fc region); determining the percent of branched glycans (e.g., on the Fc regions) of the polypeptides that have at least one galactose connected to a terminal sialic acid (e.g., on an α 1,3 arm of the glycan, linked to the galactose via a NeuAc-α 2,6-Gal terminal linkage); and processing the test preparation into a pharmaceutical product if the percent of branched glycans (e.g., on the Fc regions) of the polypeptides is greater than 10% (e.g., greater than 15%, 20%, 25%, 30%, 35%, 40%, 45%, 50%, 55%, 60%, 65%, 70%, 75%, 80%, 85%, 90%, 95%, up to and including 100%), thereby manufacturing a pharmaceutical product.

In further embodiments, the processing step includes combining the test preparation with an excipient or buffer.

In other embodiments, the processing step includes: (a) combining (e.g., formulating) the preparation with a pharmaceutically acceptable excipient; and (b) packaging the combination with instructions for use in the treatment of one or more neurodegenerative diseases.

In still other embodiments, the processing step includes one or more of: formulating the test preparation; processing the test preparation into a drug product; combining the test preparation with a second component, e.g., an excipient or buffer; changing the concentration of the polypeptide in the preparation; lyophilizing the test preparation; combining a first and second aliquot of the polypeptide to provide a third, larger, aliquot; dividing the test preparation into smaller aliquots; disposing the test preparation into a container, e.g., a gas or liquid tight container; packaging the test preparation; associating a container comprising the test preparation with a label (e.g., labeling); and shipping or moving the test preparation to a different location.

In some embodiments of any of the foregoing methods, the polypeptides include a human IgG Fc region (e.g., IgG1, IgG2, IgG3, or IgG4). In other embodiments of any of the foregoing methods, the polypeptides include human IgG1, IgG2, IgG3 or IgG4, or a mixture thereof.

In a further aspect, the disclosure features a method of selecting a preparation useful for the treatment of neurodegeneration. This method includes the steps of providing a sample of a test preparation (e.g., derived from IVIG) including polypeptides (e.g., polypeptides having an IgG Fc region); acquiring an input value for the test preparation for one or more parameters listed in Table 1; acquiring one or more assessments made by comparing the input value for the test preparation with one or more target value, and selecting the test preparation as being useful for the treatment of neurodegeneration if the input values for at least one parameter in the test preparation listed in Table 1 meet the corresponding target value for the parameter.

In some embodiments, the test preparation is derived from IVIG. In certain embodiments, the test preparation is a modified IVIG preparation or IVIG fraction. In other embodiments, the test preparation includes an Fc region derived from IVIG.

In certain embodiments of any of the foregoing methods, neurodegeneration is related to a disease selected from the group consisting of age-related dementia, Alzheimer's disease, Amyotrophic lateral sclerosis (ALS), cerebellar ataxia, Creutzfedt-Jakob disease, Down's syndrome, frontotemporal lobar degenerations/dementia, Huntington's disease, inclusion body myositis, Lewy body dementia, chronic inflammatory demyelinating polyneuropathy, Guillain-Barre syndrome, Charcot-Marie-Tooth syndrome, myasthenia gravis, Lambert-Eaton myasthenic syndrome, multifocal motor neuropathies, multiple sclerosis, multiple-system atrophy, Parkinson's disease, vascular dementia, Lennox-Gastaut syndrome, ataxia telangiectasia, neurodegenerative Lyme disease, acute disseminating encephalomyelitis, acute idiopathic dysautonomia, adrenoleukodystrophy, demyelinative brain stem encephalitis, demyelinating neuropathy associated with monoclonal IgM, HTLV-1-associated myelopathy, other paraneoplastic neurodegeneration, neuropathy or encephalopathies, lumbosacral or brachial plexitis, POEMS syndrome, post-infection cerebellar ataxia, presbycusis, spinocerebellar ataxia, other peripheral neuropathies (e.g., mononeuropathy, mononeuritis multiplex, polyneuropathy, autonomic neuropathy, and neuritis), and vascular dementia.

TABLE 1

| Parameter # | Parameter | Reference Assay |
|---|---|---|
| 1 | Reduction of microglia-dependent clearance of native Aβ deposits | See Puli et al *J Neuroinflammation* 9:105 (2012) Note: different populations of microglia can be derived from adult or neonatal mouse brains or differentiated from PBMCs |
| 2 | Increased binding and phagocytosis of Aβ by microglia | Uptake of fluorescent-labeled Aβ peptide by primary mouse or human microglial cells or cell lines. See Hickman et al *J Neuroscience* 28:8354 (2008) Griciuc et al *Neuron*. pii: S0896-6273(13)00316-4 epub ahead of print (2013) |
| 3 | Increased CCR2 monocytes in peripheral and CNS tissues | FACS analysis of CD11b+, CD45hi, CCR2+ monocytic cells See Example 2, El Khoury et al *Nat Med* 13:432 (2007), and Naert et al *J Neuroscience* 31:6208 (2011) |
| 4 | Increased neurogenesis | Doublecortin (and/or BrdU) staining in histological sections in EAE models See Puli et al *J Neuroinflammation* 9:105 (2012) |
| 5 | Decrease in circulating CCL11/eotaxin | ELISA, MSD, Luminex assay of blood and other tissues following in vivo treatment with MG in a model of neuroinflammation and neurodegeneration including AD models and EAE See Example 2 |
| 6 | Decrease in circulating CCl2/MCP-1 | ELISA, MSD, Luminex assay of blood and other tissues following in vivo treatment with MG in a model of neurooinflammation and neurodegeneration including AD models and EAE See Example 2 |
| 7 | Decrease in circulating CCl12, CCL19, G-CSF, GM-CSF, CCL5, CXCL10, haptoglobulin, CRP, beta2microglobulin | ELISA, MSD, Luminex assay of blood and other tissues following in vivo treatment with MG in a model of neuroinflammation and neurodegeneration including AD models and EAE See Example 2 |
| 8 | Decreased CNS infiltration of parenchymal microglia | CD11b+, CD45+ cells from CNS by FACS See Example 2 |
| 9 | Decrease in inflammatory cell activity | ELISA, MSD, Luminex measurements of circulating shed L-selectin, E-selectin, P-selectin, ICAM, VCAM |
| 10 | Decreased inflammatory cell binding related to decreased inflammatory infiltration of BBB | Leukocyte adhesion to substrate-bound adhesion molecules in vitro and leukocyte or lymphocyte binding and extravasation through the blood brain barrier measured by intravital microscopy or immunohistochemistry in EAE or TNFa-induced. See Coisne et al *J Immunol*. 182:5909 (2009), Dos Santos et al *J Neuroinflammation* 5:49 (2008), Jain et al *J Immunol* 184:7196 (2010), Lapointe et al *Brain* 127:2649 (2004). |
| 11 | Decreased T cell activation | Increased T regulatory cells in peripheral tissues or CNS by FACS, increased naive T cells (CD4+ or CD8+) by FACS in peripheral tissues or CNS, and decreased memory T cells |

TABLE 1-continued

| Parameter # | Parameter | Reference Assay |
|---|---|---|
| | | (CD4+ or CD8+) by FACS in peripheral tissues or CNS. See Example 2 |
| 12 | Decreased T cell activation of microglia | Inflammatory cytokine production (ELISA, MSD, Luminex) produced by microglia and activation markers (FACS) on microglia after coculture with activated T cells from PBMCs. Microglia from various sources. See Janke and Jong *Neurol. Res.* 28:270 (2006). |
| 13 | Decreased Aβ-induced neuronal cell death | Neuronal viability measurement (LDH release, MTT assay, trypan blue exclusion, image-based quantitation of neuronal cells or cell markers or other methods) after culture of neuronal cells from various sources with Aβ peptides. See Widiapradja et al *J Neurochem* 122:321 (2012) |
| 14 | Decreased activated T cell killing of neurons | Neuronal viability measurement (LDH release, MTT assay, trypan blue exclusion, image-based quantitation of neuronal cells or cell markers or other methods). Activated PBMCs enriched for T cells are treated with agents to inhibit neuronal killing upon subsequent coculture. Various sources of neuronal cells may be employed. See Janke et al *Neurol. Res.* 28:270 (2006). |
| 15 | Decreased oxygen or glucose deprivation-induced neuronal cell death or apoptosis | Neuronal viability measurement (LDH release, MTT assay, trypan blue exclusion, image-based quantitation of neuronal cells or cell markers or other methods) after culture of neuronal cells from various sources following oxygen or glucose deprivation. See Arumugam et al *Procd. Natl. Acd. Sci.* 104:14101 (2007). |
| 16 | Maintains BBB integrity | Transwell migration and label penetration assays with HUVEC or CNS-derived EC and with or without pericytes or fibroblasts. The contribution of apoE variants to BBB can be tested. Cell isolation and co-culture conditions. See Nishitsuji et al *J Biol Chem.* 286:17536 (2011). |

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

These and other aspects of the invention are described in more detail below and in the claims.

DESCRIPTION OF THE FIGURES

FIG. 3A depicts an exemplary ST6 sialyltransferase amino acid sequence (SEQ ID NO:1).

FIG. 3B depicts an exemplary ST6 sialyltransferase amino acid sequence (SEQ ID NO:2). FIG. 3C depicts an exemplary ST6 sialyltransferase amino acid sequence (SEQ ID NO:3).

FIG. 4 is a schematic illustration of a reaction scheme for ST6 sialyltransferase (fucose: triangles, N-acetylglucosamine: squares, mannose: dark circles, galactose: light circles, sialic acid: diamonds).

DETAILED DESCRIPTION

Figure 1:
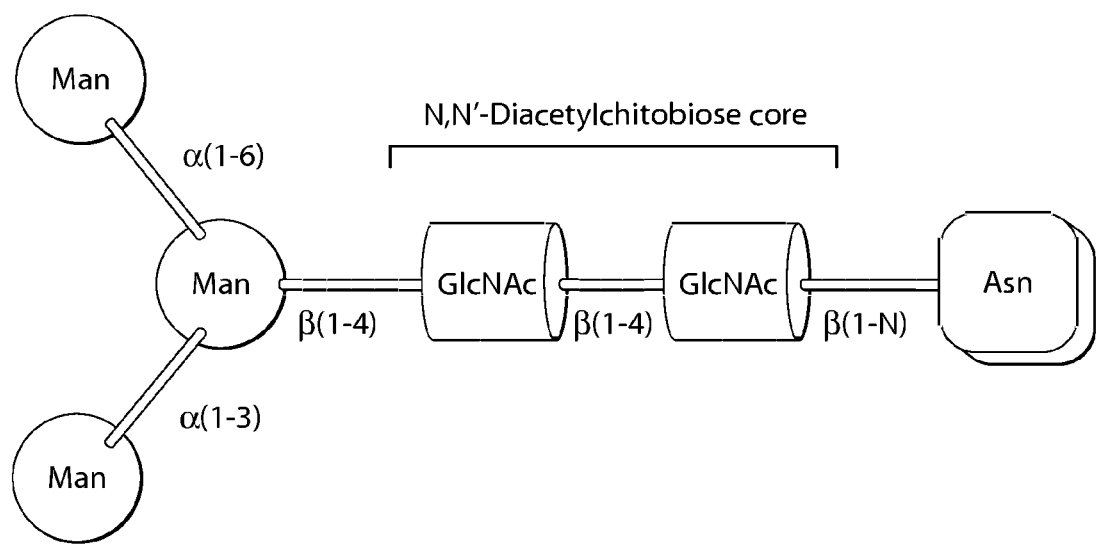
FIG. 1 is a schematic illustration of a common core pentasaccharide $(Man)_3(GlcNAc)(GlcNAc)$ of N-glycans.

Antibodies are glycosylated at conserved positions in the constant regions of their heavy chain.

For example, IgG antibodies have a single N-linked glycosylation site at Asn297 of the $C_H2$ domain. Each antibody isotype has a distinct variety of N-linked carbohydrate structures in the constant regions. For human IgG, the core oligosaccharide normally consists of $GlcNAc_2Man_3GlcNAc$, with differing numbers of outer residues. Variation among individual IgGs can occur via attachment of galactose and/or galactose-sialic acid at one or both terminal GlcNAc or via attachment of a third GlcNAc arm (bisecting GlcNAc).

The present disclosure relates to polypeptide preparations (e.g., Fc region-containing polypeptide preparations (e.g., IVIG, Fc or IgG antibodies)) having particular levels of branched glycans that are sialylated on an α1,3 arm, an α1,6 arm, or both, of the branched glycans in the Fc region (e.g., with a NeuAc-α2,6-Gal terminal linkage). The levels can be measured on an individual Fc region (e.g., the number of branched glycans that are sialylated on an α1,3 arm, an α1,6 arm, or both, of the branched glycans in the Fc region), or on the overall composition of a preparation of polypeptides (e.g., the number or percentage of branched glycans that are sialylated on an α1,3 arm, an α1,6 arm, or both, of the branched glycans in the Fc region in a preparation of polypeptides).

The inventors have discovered that Fc region-containing polypeptides having branched glycans that are preferentially sialylated on an α 1,3 arm of the branched glycan in the Fc region (e.g., with a NeuAc-α 2,6-Gal terminal linkage) are useful for the treatment of neurodegeneration, e.g., neurodegenerative diseases. Described herein are polypeptides (e.g., antibodies or fusion proteins, such as Fc fusion proteins) having branched glycans sialylated on an α 1,3 arm of the branched glycan in the Fc region (e.g., with a NeuAc-α 2,6-Gal terminal linkage) and useful in the treatment of neurodegeneration, e.g., neurodegenerative diseases. Methods of making and using such compositions are also described.

Preparations useful herein can be obtained from any source. In some instances, providing or obtaining a preparation (e.g., such as a biologic drug substance or a precursor thereof), e.g., that is or includes a polypeptide, can include providing a host cell, e.g., a mammalian host cell (e.g., a CHO cell) that is genetically engineered to express a polypeptide (e.g., a genetically engineered cell); culturing the host cell under conditions suitable to express the polypeptide (e.g., mRNA and/or protein); and, optionally, purifying the expressed polypeptide, e.g., in the form of a recombinant fusion protein) from the cultured cell, thereby producing a preparation.

Definitions

As used herein, "acquire or acquiring (e.g., acquiring information)" means obtaining possession of a physical entity, or a value, e.g., a numerical value, by "directly acquiring" or "indirectly acquiring" the physical entity or value. "Directly acquiring" means performing a process (e.g., performing an assay or test on a sample or "analyzing a sample" as that term is defined herein) to obtain the physical entity or value. "Indirectly acquiring" refers to receiving the physical entity or value from another party or source (e.g., a third party laboratory that directly acquired the physical entity or value). "Directly acquiring" a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. "Directly acquiring" a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. Exemplary analytical methods are shown in Table 2.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

In some instances, a preparation (e.g., such as a preparation of an Fc region-containing polypeptide) can be a sample from a proposed or test batch of a drug product. As used herein, a "batch" of a preparation refers to a single production run. Evaluation of different batches thus means evaluation of different production runs or batches. As used herein "sample(s)" refer to separately procured samples. For example, evaluation of separate samples could mean evaluation of different commercially available containers or vials of the same batch or from different batches. A batch can include a drug product.

As used herein, the term "constant region" refers to a polypeptide that corresponds to, or is derived from, one or more constant region immunoglobulin domains of an antibody. A constant region can include any or all of the following immunoglobulin domains: a $C_H1$ domain, a hinge region, a $C_H2$ domain, a $C_H3$ domain (derived from an IgA, IgD, IgG, IgE, or IgM), and a $C_H4$ domain (derived from an IgE or IgM).

As used herein, "IVIG" is a preparation of pooled, polyvalent IgG, including all four IgG subgroups, extracted from plasma of at least 1,000 human donors. IVIG is approved as a plasma protein replacement therapy for immune deficient patients. The level of IVIG Fc glycan sialylation varies between about 10-20% among IVIG preparations.

As used herein, the term "derived from IVIG" refers to polypeptides which result from manipulation of IVIG. For example, polypeptides purified from IVIG (e.g., enriched for sialylated IgGs, modified IVIG (e.g., IVIG IgGs enzymatically sialylated), or Fc regions of IVIG (e.g., papain digested and sialylated) are derived from IVIG.

As used herein, "evaluating," e.g., in the evaluation/ evaluating, identifying, and/or producing aspects disclosed herein, means reviewing, considering, determining, assessing, analyzing, measuring, and/or detecting the presence, absence, level, and/or ratio of one or more parameters in a preparation to provide information pertaining to the one or more parameters. In some instances, evaluating can include performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. "Evaluating" can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

As used herein, the term "Fc region" refers to a dimer of two "Fc polypeptides," each "Fc polypeptide" including the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or the entire flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

An "Fc region-containing polypeptide" is a polypeptide that includes all or a substantial portion of an Fc region. Examples of an Fc region-containing polypeptide preparation include, e.g., a preparation of Fc fragments, a preparation of antibody molecules, a preparation of Fc-fusion proteins (e.g., an Fc-receptor fusion protein), and a preparation of pooled, polyvalent immunoglobulin molecules (e.g., IVIG). Such an Fc region-containing polypeptide may be recombinant (e.g., a recombinant Fc fragment preparation or a recombinant antibody preparation) or naturally derived (such as IVIG).

As used herein, the term "Fc region variant" refers to an analog of an Fc region that possesses one or more Fc-mediated activities described herein. This term includes Fc regions having one or more amino acid modifications (e.g., substitutions, additions, or deletions) relative to a wild-type or naturally existing Fc region. For example, variant Fc regions can possess at least about 50% homology, at least about 75% homology, at least about 80% homology, at least about 85%, homology, at least about 90% homology, at least about 95% homology, or more, with a naturally existing Fc region. For example, variant Fc regions can possess between 1 and 5 amino acid substitutions, e.g., 1, 2, 3, 4 or 5 amino acid substitutions such as phenylalanine to alanine substitutions. Fc region variants also include Fc regions having one or more amino acid residues added to or deleted from the N- or C-terminus of a wild type Fc region.

As used herein, "glycan" is a sugar, which can be monomers or polymers of sugar residues, such as at least three sugars, and can be linear or branched. A "glycan" can include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoconjugate (e.g., of a polypeptide, glycolipid, proteoglycan, etc.). The term also encompasses free glycans, including glycans that have been cleaved or otherwise released from a glycoconjugate.

As used herein, the term "glycoprotein" refers to a protein that contains a peptide backbone covalently linked to one or more sugar moieties (i.e., glycans). The sugar moiety(ies) may be in the form of monosaccharides, disaccharides, oligosaccharides, and/or polysaccharides. The sugar moiety (ies) may comprise a single unbranched chain of sugar residues or may comprise one or more branched chains. Glycoproteins can contain O-linked sugar moieties and/or N-linked sugar moieties.

As used herein, the term "neurodegeneration" refers to the progressive loss of structure or function of neurons, including death of neurons. The term "neurodegenerative disease" refers to diseases in which neurodegeneration is, at least in part, a cause, symptom or phenotype. Exemplary neurodegenerative diseases include, but are not limited to, age-related dementia, Alzheimer's disease, Amyotrophic lateral sclerosis (ALS), cerebellar ataxia, Creutzfedt-Jakob disease, Down's syndrome, frontotemporal lobar degenerations/dementia, Huntington's disease, inclusion body myositis, Lewy body dementia, chronic inflammatory demyelinating polyneuropathy, Guillain-Barre syndrome, Charcot-Marie-Tooth syndrome, myasthenia gravis, Lambert-Eaton myasthenic syndrome, multifocal motor neuropathies, multiple sclerosis, multiple-system atrophy, Parkinson's disease, vascular dementia, Lennox-Gastaut syndrome, ataxia telangiectasia, neurodegenerative Lyme disease, acute disseminating encephalomyelitis, acute idiopathic dysautonomia, adrenoleukodystrophy, demyelinative brain stem encephalitis, demyelinating neuropathy associated with monoclonal IgM, HTLV-1-associated myelopathy, other paraneoplastic neurodegeneration, neuropathy or encephalopathies, lumbosacral or brachial plexitis, POEMS syndrome, post-infection cerebellar ataxia, presbycusis, spinocerebellar ataxia, other peripheral neuropathies (e.g., mononeuropathy, mononeuritis multiplex, polyneuropathy, autonomic neuropathy, and neuritis).

As used herein, an "N-glycosylation site of an Fc polypeptide" refers to an amino acid residue within an Fc polypeptide to which a glycan is N-linked. In some embodiments, an Fc region contains a dimer of Fc polypeptides, and the Fc region comprises two N-glycosylation sites, one on each Fc polypeptide.

As used herein "percent (%) of branched glycans" refers to the number of moles of glycan X relative to total moles of glycans present, wherein X represents the glycan of interest.

As used herein "percent (%) sequence identity" with respect to a sequence is defined as the percentage of amino acid residues or nucleotides in a candidate sequence that are identical with the amino acid residues or nucleotides in the reference sequence, after aligning the sequences and introducing gaps, if necessary, to achieve the maximum percent sequence identity. Gaps can be introduced in one or both of a first and a second amino acid or nucleic acid sequence for optimal alignment and non-homologous sequences can be disregarded for comparison purposes. Alignment for purposes of determining percent sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In one embodiment, the length of a reference sequence aligned for comparison purposes is at least 30%, e.g., at least 40%, e.g., at least 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. In some instances a product will include amino acid variants, e.g., species that differ at terminal residues, e.g., at one, two, three, or four N-terminal residues and/or one C-terminal residue. In instances of such cases the sequence identity which is compared is the identity between the primary amino acid sequences of the most abundant active species in each of the products being compared. In some instances sequence identity refers to the amino acid sequence encoded by a nucleic acid that can be used to make the product.

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

As used herein, "polynucleotide" (or "nucleotide sequence" or "nucleic acid molecule") refers to an oligonucleotide, nucleotide, or polynucleotide, and fragments or portions thereof, and to DNA or RNA of genomic or synthetic origin, which may be single- or double-stranded, and represent the sense or anti-sense strand.

As used herein, "polypeptide" (or "amino acid sequence" or "protein") refers to a glycoprotein, oligopeptide, peptide, polypeptide, or protein sequence, and fragments or portions thereof, and to naturally occurring or synthetic molecules. "Amino acid sequence" and like terms, such as "polypeptide" or "protein," are not meant to limit the indicated amino acid sequence to the complete, native amino acid sequence associated with the recited protein molecule.

"Predetermined level" as used herein, refers to a pre-specified particular level of one or more particular glycans, e.g., branched glycans having a sialic acid on an $\alpha$1,3 arm, and/or branched glycans having a sialic acid on an $\alpha$1,6 arm, and/or branched glycans having a sialic acid on an $\alpha$1,3 arm and on an $\alpha$1,6 arm. In some embodiments, a predetermined level is an absolute value or range. In some embodiments, a predetermined level is a relative value. In some embodiments, a predetermined level is the same as or different (e.g., higher or lower than) a level of one or more particular glycans (e.g., branched glycans having a sialic acid on an $\alpha$1,3 arm, and/or branched glycans having a sialic acid on an $\alpha$1,6 arm, and/or branched glycans having a sialic acid on an $\alpha$1,3 arm and on an $\alpha$1,6 arm) in a reference, e.g., a reference polypeptide product, or a reference document such as a specification, alert limit, or master batch record for a pharmaceutical product.

In some embodiments, a predetermined level is an absolute level or range of (e.g., number of moles of) one or more glycans (e.g., branched glycans having a sialic acid on an $\alpha$1,3 arm, and/or branched glycans having a sialic acid on an $\alpha$1,6 arm, and/or branched glycans having a sialic acid on an $\alpha$1,3 arm and on an $\alpha$1,6 arm) in a polypeptide preparation. In some embodiments, a predetermined level is a level or range of one or more glycans (e.g., branched glycans having a sialic acid on an $\alpha$1,3 arm, and/or branched glycans having a sialic acid on an $\alpha$1,6 arm, and/or branched glycans having a sialic acid on an $\alpha$1,3 arm and on an $\alpha$1,6 arm) in a polypeptide preparation relative to total level of glycans in the polypeptide preparation. In some embodiments, a predetermined level is a level or range of one or more glycans (e.g., branched glycans having a sialic acid on an $\alpha$1,3 arm, and/or branched glycans having a sialic acid on an $\alpha$1,6 arm, and/or branched glycans having a sialic acid on an $\alpha$1,3 arm and on an $\alpha$1,6 arm) in a polypeptide preparation relative to total level of sialylated glycans in the polypeptide preparation. In some embodiments, a predetermined level is expressed as a percent.

By "purified" (or "isolated") refers to a polynucleotide or a polypeptide that is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acids. An isolated polynucleotide or polypeptide can be at least 60% free, or at least 75% free, or at least 90% free, or at least 95% free from other components present in natural environment of the indicated polynucleotide or polypeptide.

"Reference polypeptide", as used herein, refers to a polypeptide having substantially the same amino acid sequence as (e.g., having about 95-100% identical amino acids of) a polypeptide described herein, e.g., a polypeptide to which it is compared. In some embodiments, a reference polypeptide is a therapeutic polypeptide described herein, e.g., an FDA approved therapeutic polypeptide.

As used herein, the term "ST6 sialyltransferase" refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71% or 70% identity with a protein involved in transfer of a sialic acid to a terminal galactose of a glycan through an $\alpha$2,6 linkage (e.g., ST6 Gal-I). A wide variety of ST6 sialyltransferase sequences are known in the art, such as those described herein; in some embodiments, an ST6 sialyltransferase shares at least one characteristic sequence of and/or shows the specified degree of overall sequence identity with one of the ST6 sialyltransferases set forth herein (each of which may be considered a "reference" ST6 sialyltransferase). In some embodiments, an ST6 sialyltransferase as described herein shares at least one biological activity with a reference ST6 sialyltransferase as set forth herein. In some such embodiment, the shared biological activity relates to transfer of a sialic acid to a glycan.

The term "subject," as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow. In a preferred embodiment, the subject is a human.

As used herein, "target value" refers to a statistically significant change (e.g. a greater than 10%, 15%, 20%, 25%, 30%, 35%. 40%, 45%, 50% or more change) relative to an unmodified polypeptide having an IgG Fc region, e.g., IVIG.

The term "treatment" or "treating," as used herein, refers to administering a therapy in an amount, manner, and/or mode effective to improve a condition, symptom, or parameter associated with a disorder or condition or to prevent or reduce progression of a disorder or condition to a degree detectable to one skilled in the art. An effective amount, manner, or mode can vary depending on the subject and may be tailored to the subject.

As used herein, the terms "coupled," "linked," "joined," "fused," and "fusion" are used interchangeably. These terms refer to the joining together of two more elements or components by whatever means, including chemical conjugation or recombinant means.

The terms "overexpress," "overexpression," or "overexpressed" interchangeably refer to a polypeptide or polynucleotide that is transcribed or translated at a detectably greater level, such as in a cancer cell, in comparison to a control cell. The term includes expression due to transcription, post-transcriptional processing, translation, post-translational processing, cellular localization (e.g., organelle, cytoplasm, nucleus, cell surface), and RNA and protein stability, as compared to a control cell. Overexpression can be detected using conventional techniques, e.g., for detecting mRNA (i.e., RT-PCR, PCR, hybridization) or proteins (i.e., ELISA, immunohistochemical techniques). Overexpression can be expression in an amount greater than about 10%, 20%, 30%, 40%, 50%, 60%, 70%, 80%, 90% or more compared to a control cell. In certain instances, overexpression is 1-fold, 2-fold, 3-fold, 4-fold, or more, higher level of transcription or translation compared to a control cell.

While the present disclosure provides exemplary units and methods for the evaluation, identification, and production methods disclosed herein, a person of ordinary skill in the art will appreciate that performance of the evaluation, identification, and production methods herein is not limited to use of those units and/or methods. For example, "percent of branched glycans" provided herein are generally described, as a value for a glycan or structure relative to total glycan or structure on a mol/mol basis. A person of skill in the art understands that although the use of other metrics or units (e.g., mass/mass, mole percent vs. weight percent) to measure a described parameter might give rise to different absolute values than those described herein, a test preparation meets a disclosed target value even if other units or metrics are used, as long as the test preparation meets the herein disclosed value when the herein disclosed units and metrics are used, e.g., allowing for the sensitivity (e.g., analytical variability) of the method being used to measure the value.

II. Polypeptides

Examples of an Fc region-containing polypeptide preparation include, e.g., a preparation of Fc fragments, a preparation of antibody molecules, a preparation of Fc-fusion proteins (e.g., an Fc-receptor fusion protein), and a preparation of pooled, polyvalent immunoglobulin molecules (e.g., IVIG). Fc region-containing polypeptides may be recombinant or naturally derived.

Naturally derived polypeptides that can be used in the methods of the invention include, for example intravenous immunoglobulin (IVIG) and polypeptides derived from IVIG (e.g., polypeptides purified from IVIG (e.g., enriched for sialylated IgGs), modified IVIG (e.g., IVIG IgGs enzymatically sialylated), or Fc regions of IVIG (e.g., papain digested and sialylated)).

Recombinant Fc region-containing polypeptides that can be used in the methods of the invention can be, for example expressed in and purified from CHO cells and sialylated using human ST6-Gal sialtransferase enzyme (expressed in and purified from $E.\ coli$ cells) or expressed in and purified from CHO cells and sialylated using human ST6-Gal sialtransferase enzyme (expressed in and purified from CHO cells).

A. N-Linked Glycosylation

N-linked oligosaccharide chains are added to a protein in the lumen of the endoplasmic reticulum. Specifically, an initial oligosaccharide (typically 14-sugar) is added to the amino group on the side chain of an asparagine residue contained within the target consensus sequence of Asn-X-Ser/Thr, where X may be any amino acid except proline. The structure of this initial oligosaccharide is common to most eukaryotes, and contains 3 glucose, 9 mannose, and 2 N-acetylglucosamine residues. This initial oligosaccharide chain can be trimmed by specific glycosidase enzymes in the endoplasmic reticulum, resulting in a short, branched core oligosaccharide composed of two N-acetylglucosamine and three mannose residues. One of the branches is referred to in the art as the "α 1,3 arm," and the second branch is referred to as the "α 1,6 arm," as denoted in FIG. 1.

N-glycans can be subdivided into three distinct groups called "high mannose type," "hybrid type," and "complex type," with a common pentasaccharide core (Man (α 1,6)-(Man(α 1,3))-Man(β 1,4)-GlcpNAc(β 1,4)-GlcpNAc(β 1,N)-Asn) occurring in all three groups.

After initial processing in the endoplasmic reticulum, the polypeptide is transported to the Golgi where further processing may take place. If the glycan is transferred to the Golgi before it is completely trimmed to the core pentasaccharide structure, it results in a "high-mannose glycan."

Additionally or alternatively, one or more monosaccharides units of N-acetylglucosamine may be added to the core mannose subunits to form a "complex glycan." Galactose may be added to the N-acetylglucosamine subunits, and sialic acid subunits may be added to the galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases.

"Hybrid glycans" comprise characteristics of both high-mannose and complex glycans. For example, one branch of a hybrid glycan may comprise primarily or exclusively mannose residues, while another branch may comprise N-acetylglucosamine, sialic acid, galactose, and/or fucose sugars.

Sialic acids are a family of 9-carbon monosaccharides with heterocyclic ring structures. They bear a negative charge via a carboxylic acid group attached to the ring as well as other chemical decorations including N-acetyl and N-glycolyl groups. The two main types of sialyl residues found in polypeptides produced in mammalian expression systems are N-acetyl-neuraminic acid (NeuAc) and N-glycolylneuraminic acid (NeuGc). These usually occur as terminal structures attached to galactose (Gal) residues at the non-reducing termini of both N- and O-linked glycans. The glycosidic linkage configurations for these sialyl groups can be either a 2,3 or a 2,6.

Fc regions are glycosylated at conserved, N-linked glycosylation sites. For example, each heavy chain of an IgG antibody has a single N-linked glycosylation site at Asn297 of the $C_H2$ domain. IgA antibodies have N-linked glycosylation sites within the $C_H2$ and $C_H3$ domains, IgE antibodies have N-linked glycosylation sites within the $C_H3$ domain, and IgM antibodies have N-linked glycosylation sites within the $C_H1$, $C_H2$, $C_H3$, and $C_H4$ domains.

Each antibody isotype has a distinct variety of N-linked carbohydrate structures in the constant regions. For example, IgG has a single N-linked biantennary carbohydrate at Asn297 of the $C_H2$ domain in each Fc polypeptide of the Fc region, which also contains the binding sites for C1q and FcγR. For human IgG, the core oligosaccharide normally consists of GlcNAc$_2$Man$_3$GlcNAc, with differing numbers of outer residues. Variation among individual IgG can occur via attachment of galactose and/or galactose-sialic acid at one or both terminal GlcNAc or via attachment of a third GlcNAc arm (bisecting GlcNAc).

B. Antibodies

Figure 2:
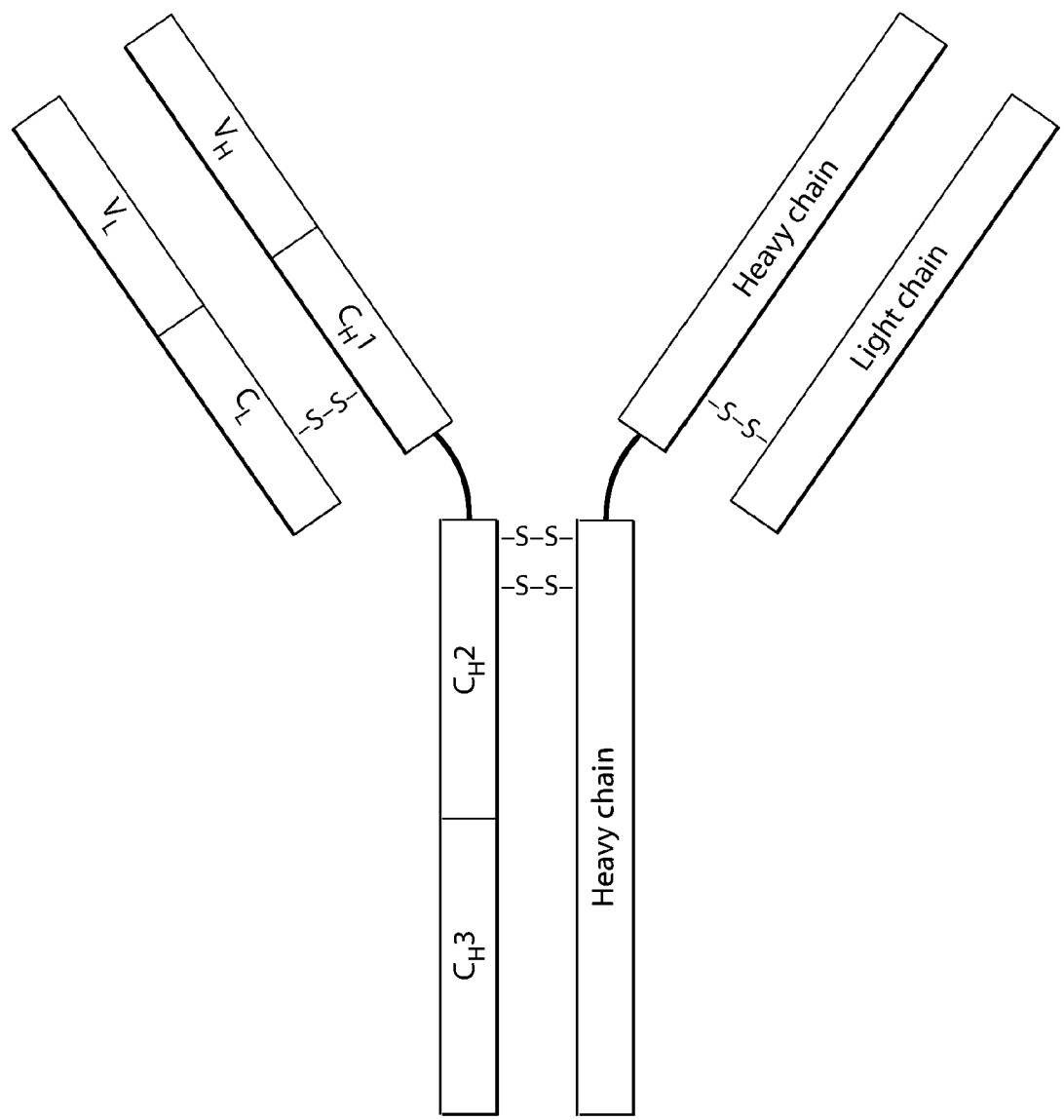
FIG. 2 is a schematic illustration of an IgG antibody molecule.

The basic structure of an IgG antibody is illustrated in FIG. 2. As shown in FIG. 2, an IgG antibody consists of two identical light polypeptide chains and two identical heavy polypeptide chains linked together by disulphide bonds. The first domain located at the amino terminus of each chain is variable in amino acid sequence, providing the antibody binding specificities found in each individual antibody. These are known as variable heavy ($V_H$) and variable light ($V_L$) regions. The other domains of each chain are relatively invariant in amino acid sequence and are known as constant heavy ($C_H$) and constant light ($C_L$) regions. As shown in FIG. 2, for an IgG antibody, the light chain includes one variable region ($V_L$) and one constant region ($C_L$). An IgG heavy chain includes a variable region ($V_H$), a first constant region ($C_H1$), a hinge region, a second constant region ($C_H2$), and a third constant region ($C_H3$). In IgE and IgM antibodies, the heavy chain includes an additional constant region ($C_H4$).

Antibodies described herein can include, for example, monoclonal antibodies, polyclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "Fc fragment," as used herein, refers to one or more fragments of an Fc region that retains an Fc function and/or activity described herein, such as binding to an Fc receptor. Examples of such fragments include fragments that include an N-linked glycosylation site of an Fc region (e.g., an Asn297 of an IgG heavy chain or homologous sites of other antibody isotypes), such as a $C_H2$ domain. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) Nature 341:544-546), and an isolated complementarily determining region (CDR). These antibody fragments can be obtained using conventional techniques known to those with skill in the art, and the fragments can be screened for utility in the same manner as are intact antibodies.

Reference Fc region-containing polypeptides described herein can be produced by any method known in the art for the synthesis of antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645).

Additional reference Fc region-containing polypeptides described herein are bispecific antibodies and multivalent antibodies, as described in, e.g., Segal et al., J. Immunol. Methods 248:1-6 (2001); and Tutt et al., J. Immunol. 147: 60 (1991).

C. Polypeptide Conjugates

The disclosure includes polypeptides (or Fc regions or Fc fragments thereof containing one or more N-glycosylation sites) that are conjugated or fused to one or more heterologous moieties and that have different levels of sialylated glycans relative to a corresponding reference polypeptide.

Heterologous moieties include, but are not limited to, peptides, polypeptides, proteins, fusion proteins, nucleic acid molecules, small molecules, mimetic agents, synthetic drugs, inorganic molecules, and organic molecules. In some instances, a reference polypeptide is a fusion protein that comprises a peptide, polypeptide, protein scaffold, scFv, dsFv, diabody, Tandab, or an antibody mimetic fused to an Fc region, such as a glycosylated Fc region. The fusion protein can include a linker region connecting the Fc region to the heterologous moiety (see, e.g., Hallewell et al. (1989), J. Biol. Chem. 264, 5260-5268; Alfthan et al. (1995), Protein Eng. 8, 725-731; Robinson & Sauer (1996)).

In some instances, a reference fusion protein includes an Fc region (or an Fc fragment containing one or more N-glycosylation sites thereof) conjugated to a heterologous polypeptide of at least 10, at least 20, at least 30, at least 40, at least 50, at least 60, at least 70, at least 80, at least 90 or at least 100 amino acids.

In some instances, a reference fusion protein can include an Fc region (or Fc fragment containing one or more N-glycosylation sites thereof) conjugated to marker sequences, such as a peptide to facilitate purification. A particular marker amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, Cell 37:767) and the "Flag" tag.

In other instances, a reference polypeptide (or an Fc region or Fc fragment containing one or more N-glycosylation sites thereof) is conjugated to a diagnostic or detectable agent. Such fusion proteins can be useful for monitoring or prognosing the development or progression of disease or disorder as part of a clinical testing procedure, such as determining the efficacy of a particular therapy. Such diagnosis and detection can be accomplished by coupling the polypeptide to detectable substances including, but not limited to, various enzymes, such as but not limited to horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I), carbon ($^{14}$C), sulfur ($^{35}$S), tritium ($^3$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{153}$Gd, $^{159}$Gd, $^{149}$Pm, $^{140}$La, $^{169}$Yb, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{51}$Cr, $^{54}$Mn, $^{75}$Se, $^{113}$Sn, and $^{117}$Sn; positron emitting metals using various positron emission tomographies, non-radioactive paramagnetic metal ions, and molecules that are radiolabelled or conjugated to specific radioisotopes.

Techniques for conjugating therapeutic moieties to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987)).

D. Sialyltransferase Polypeptides

Methods and compositions described herein include the use of a sialyltransferase enzyme, e.g., an α 2,6 sialyltransferase (e.g., ST6 Gal-I). A number of ST6 sialyltransferases are known in the art and are commercially available (see, e.g., Takashima, Biosci. Biotechnol. Biochem. 72:1155-1167 (2008); Weinstein et al., J. Biol. Chem. 262:17735-17743 (1987)). ST6 Gal-I catalyzes the transfer of sialic acid from a sialic acid donor (e.g., cytidine 5'-monophospho-N-acetyl neuraminic acid) to a terminal galactose residue of glycans through an α 2,6 linkage. The sialic acid donor reaction product is cytidine 5'-monophosphate. FIGS. 3A-3C depict three exemplary ST6 sialyltransferase amino acid sequences (SEQ ID NOs:1-3). In some embodiments, an ST6 sialyltransferase has or includes an amino acid sequence set forth in SEQ ID NO:1, SEQ ID NO:2, or in amino acid residues 95-416 of SEQ ID NO:3, or a characteristic sequence element thereof or therein. In some embodiments, an ST6 sialyltransferase has at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:1, SEQ ID NO:2, or amino acid residues 95-416 of SEQ ID NO:3. Alternatively or additionally, in some embodiments, an ST6 sialyltransferase includes at least about 5, 10, 15, 20, 25, 30, 35, 40, 45, 50, 75, 100, or 150 or more contiguous amino acid residues found in SEQ ID NO:1, SEQ ID NO:2, or amino acid residues 95-416 of SEQ ID NO:3.

In some embodiments, an ST6 sialyltransferase differs from an amino acid sequence as set forth in SEQ ID NO:1, SEQ ID NO:2, or in amino acid residues 95-416 of SEQ ID NO:3, or characteristic sequence elements thereof or therein, by one or more amino acid residues. For example, in some embodiments, the difference is a conservative or nonconservative substitution of one or more amino acid residues. Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some embodiments, an ST6 sialyltransferase polypeptide includes a substituent group on one or more amino acid residues. Still other useful polypeptides are associated with (e.g., fused, linked, or coupled to) another moiety (e.g., a peptide or molecule). For example, an ST6 sialyltransferase polypeptides can be fused, linked, or coupled to an amino acid sequence (e.g., a leader sequence, a secretory sequence, a proprotein sequence, a second polypeptide, or a sequence that facilitates purification, enrichment, or stabilization of the polypeptide).

II. Methods for Producing Sialylated Polypeptides

The present disclosure relates to Fc region-containing polypeptide preparations (e.g., IVIG, Fc, or IgG antibodies) having higher levels of branched glycans that are sialylated on an α 1,3 or 1,6 arm of the branched glycans in the Fc region (e.g., with a NeuAc-α 2,6-Gal or NeuAc-α 2,3-Gal terminal linkage), relative to a corresponding reference polypeptide preparation. The higher levels can be measured on an individual Fc region (e.g., an increase in the number of branched glycans that are sialylated on an α 1,3 arm of the branched glycans in the Fc region), or the overall composition of a preparation of polypeptides can be different (e.g., a preparation of polypeptides can have a higher number or a higher percentage of branched glycans that are sialylated on an α 1,3 arm of the branched glycans in the Fc region) relative to a corresponding preparation of reference polypeptides).

In exemplary methods, Fc molecules were obtained or produced from various sources, glycan compositions were characterized, and activities were determined. The Fc molecules were tested for their ability to protect mice from neurodegeneration in a mouse EAE model.

ST6 Gal-I sialyltransferase catalyzes the transfer of sialic acid from a sialic acid donor (e.g., cytidine 5'-monophospho-N-acetyl neuraminic acid) to a terminal galactose residue of glycans through an α 2,6 linkage. The present disclosure exploits the discovery that ST6 sialyltransferase catalyzes the transfer of sialic acid to branched glycans (e.g., Fc branched glycans) comprising an α 1,3 arm and an α 1,6 arm in an ordered fashion. As shown in FIG. 4, ST6 sialyltransferase transfers a sialic acid to an α 1,3 arm of a branched glycan, which can be followed by transfer of a second sialic acid to an α 1,6 arm (yielding a disialylated branched glycan), and can further be followed by removal of sialic acid from an α 1,3 arm (yielding a branched glycan having a sialic acid on an α 1,6 arm). Accordingly, by controlling and/or modulating activity (e.g., kinetics) of ST6 sialyltransferase, polypeptides having particular sialylation patterns can be produced.

Any parameter generally known to affect enzyme kinetics can be controlled and/or modulated to produce a polypeptide preparation having a predetermined level of sialic acid on an α 1,3 arm of a branched glycan, on an α 1,6 arm of a branched glycan, and/or on an α 1,3 arm and an α 1,6 arm of a branched glycan. For example, reaction time, ST6 sialyltransferase concentration and/or specific activity, branched glycan concentration, sialic acid donor concentration, sialic acid donor reaction product concentration, pH, buffer composition, and/or temperature can be controlled and/or modulated to produce a polypeptide preparation having a desired level of sialylation (e.g., α 1,3 arm and/or α 1,6 arm sialylation).

In some embodiments, to preferentially sialylate an α1,3 arm of branched glycans (e.g., having an α 1,3 arm and an α 1,6 arm), branched glycans are contacted in vitro with an ST6 sialyltransferase under limited reaction conditions. Such limited reaction conditions are selected such that addition of a sialic acid to an α 1,3 arm is enhanced relative to addition of a sialic acid to an α 1,6 arm (e.g., rate of transfer of a sialic acid to an α 1,3 arm ("$R_a^{1,3}$") exceeds rate of transfer of a sialic acid to an α 1,6 arm ("$R_a^{1,6}$"). In some embodiments, limited reaction conditions are further selected such that removal of a sialic acid from an α1,6 arm is enhanced relative to addition of a sialic acid to an α 1,6 arm (e.g., rate of removal of a sialic acid from an α 1,6 arm ("$R_r^{1,6}$") exceeds rate of transfer of a sialic acid to an α 1,6 arm ("$R_a^{1,6}$") Limited reaction conditions can include, for example, reduced reaction time, reduced enzyme concentration and/or activity, reduced amount of branched glycans, reduced level of sialic acid donor, and/or reduced temperature.

In some embodiments, to preferentially sialylate an α1,6 arm of branched glycans (e.g., having an α 1,3 arm and an α 1,6 arm), branched glycans can be contacted in vitro with an ST6 sialyltransferase under extended reaction conditions. Such extended reaction conditions are selected such that addition of a sialic acid to an α 1,6 arm is enhanced relative to removal of a sialic acid from an α 1,6 arm (e.g., rate of transfer of a sialic acid to an α 1,6 arm ("$R_a^{1,6}$") exceeds rate of removal of a sialic acid from an α 1,6 arm ("$R_r^{1,6}$")). In some embodiments, extended reaction conditions are further selected such that, after initial conditions that enhance addition of sialic acid to an α 1,3 arm, conditions are extended such that removal of a sialic acid from an α 1,3 arm is eventually enhanced relative to addition of a sialic acid to an α 1,3 arm (e.g., rate of removal of a sialic acid from an α 1,3 arm ("$R_r^{1,3}$") exceeds rate of transfer of a sialic acid to an α 1,3 arm ("$R_a^{1,3}$")). Extended reaction conditions can include, for example, increased reaction time, increased enzyme concentration and/or activity, increased amount of branched glycans, increased level of sialic acid donor, and/or increased temperature.

In some embodiments, to preferentially sialylate both an α 1,3 arm and an α 1,6 arm of branched glycans (e.g., having an α 1,3 arm and an α 1,6 arm), branched glycans are contacted in vitro with an ST6 sialyltransferase under intermediate reaction conditions. Such intermediate reaction conditions are selected such that addition of a sialic acid to an α 1,3 arm is enhanced relative to removal of a sialic acid from an α 1,3 arm (e.g., rate of transfer of a sialic acid to an α 1,3 arm ("$R_a^{1,3}$") exceeds rate of removal of a sialic acid from an α 1,3 arm ("$R_r^{1,3}$"). In some embodiments, intermediate reaction conditions are further selected such that addition of a sialic acid to an α 1,6 arm is enhanced relative to removal of a sialic acid from an α 1,6 arm (e.g., rate of addition of a sialic acid to an α 1,6 arm ("$R_a^{1,6}$") exceeds rate of removal of a sialic acid from an α 1,6 arm ("$R_r^{1,6}$"). Intermediate reaction conditions can include, for example, intermediate reaction time, intermediate enzyme concentration and/or activity, intermediate amount of branched glycans, intermediate level of sialic acid donor, and/or intermediate temperature. In some embodiments, intermediate reaction conditions further include supplementing the sialic acid donor at least once during the reaction. In some embodiments, intermediate reaction conditions further include removing a sialic acid donor reaction product at least once during the reaction. In some embodiments, intermediate reaction conditions further include supplementing the sialic acid donor reaction product at least once during the reaction.

In some embodiments, a polypeptide, e.g., a glycosylated antibody, is sialylated after the polypeptide is produced. For example, a polypeptide can be recombinantly expressed in a host cell (as described herein) and purified using standard methods. The purified polypeptide is then contacted with an ST6 sialyltransferase (e.g., a recombinantly expressed and purified ST6 sialyltransferase) in the presence of reaction conditions as described herein. In certain embodiments, the conditions include contacting the purified polypeptide with an ST6 sialyltransferase in the presence of a sialic acid donor, e.g., cytidine 5'-monophospho-N-acetyl neuraminic acid, manganese, and/or other divalent metal ions. In some embodiments, IVIG is used in a sialylation method described herein.

In some embodiments, chemoenzymatic sialylation is used to sialylate polypeptides. Briefly, this method involves sialylation of a purified branched glycan, followed by incorporation of the sialylated branched glycan en bloc onto a polypeptide to produce a sialylated polypeptide.

A branched glycan can be synthesized de novo using standard techniques or can be obtained from a polypeptide preparation (e.g., a recombinant polypeptide, Fc, or IVIG) using an appropriate enzyme, such as an endoglycosidase (e.g., EndoH or EndoF). After sialylation of the branched glycan, the sialylated branched glycan can be conjugated to a polypeptide using an appropriate enzyme, such as a transglycosidase, to produce a sialylated polypeptide.

In one exemplary method, a purified branched N-glycan is obtained from a polypeptide (e.g., a polypeptide preparation, e.g., IVIG) using an endoglycosidase. The purified branched N-glycan is then chemically activated on the reducing end to form a chemically active intermediate. The branched N-glycan is then further processed, trimmed, and/or glycosylated using appropriate known glycosidases. The branched glycan is then sialylated using an ST6 sialylation as described herein. After engineering, the desired branched N-glycan is transferred onto a polypeptide using a transglycosidase (such as a transglycosidase in which glycosidic activity has been attenuated using genetically engineering).

In some embodiments, a branched glycan used in methods described herein is a galactosylated branched glycan (e.g., includes a terminal galactose residue). In some embodiments, a branched glycan is galactosylated before being sialylated using a method described herein. In some embodiments, a branched glycan is first contacted with a galactosyltransferase (e.g., a beta-1,3-galactosyltransferase) and subsequently contacted with an ST6 sialyltransferase as described herein. In some embodiments, a galactosylated glycan is purified before being contacted with an ST6 sialyltransferase. In some embodiments, a galactosylated glycan is not purified before being contacted with an ST6 sialyltransferase. In some embodiments, a branched glycan is contacted with a galactosyltransferase and an ST6 sialyltransferase in a single step.

In some embodiments, a host cell is genetically engineered to express a polypeptide described herein and one or more sialyltransferase enzymes, e.g., an ST6 sialyltransferase. In some embodiments, the host cell is genetically engineered to further express a galactosyltransferase. The genetically engineered host cell can be cultured under conditions sufficient to produce a particular sialylated polypeptide. For example, to produce polypeptides preferentially sialylated on α1,3 arms of branched glycans, a host cell can be genetically engineered to express a relatively low level of ST6 sialyltransferase, whereas to produce polypeptides preferentially sialylated on α1,6 arms of branched glycans, a host cell can be genetically engineered to express a relatively high level of ST6 sialyltransferase. In some embodiments, to produce polypeptides preferentially sialylated on α1,3 arms of branched glycans, a genetically engineered host cell can be cultured in a relatively low level of sialic acid donor, whereas to produce polypeptides preferentially sialylated on α1,6 arms of branched glycans, a genetically engineered host cell can be cultured in a relatively high level of sialic acid donor.

Recombinant expression of a gene, such as a nucleic acid encoding a reference polypeptide and/or a sialtransferase described herein, can include construction of an expression vector containing a polynucleotide that encodes a reference polypeptide and/or a sialtransferase. Once a polynucleotide has been obtained, a vector for the production of the reference polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then cultured by conventional techniques to produce reference polypeptides.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For bacterial systems, a number of expression vectors can be used, including, but not limited to, the *E. coli* expression vector pUR278 (Ruther et al., 1983, EMBO 12:1791); pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST).

For expression in mammalian host cells, viral-based expression systems can be utilized (see, e.g., Logan & Shenk, 1984, Proc. Natl. Acad. Sci. USA 8 1:355-359). The efficiency of expression can be enhanced by the inclusion of appropriate transcription enhancer elements, transcription terminators, etc. (see, e.g., Bittner et al., 1987, Methods in Enzymol. 153:516-544).

In addition, a host cell strain can be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, but are not limited to, CHO, VERY, BHK, HeLa, COS, MDCK, 293, 3T3, W138, BT483, Hs578T, HTB2, BT20 and T47D, NS0 (a murine myeloma cell line that does not endogenously produce any immunoglobulin chains), CRL7O3O and HsS78Bst cells.

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

In some embodiments, a reference Fc region-containing polypeptide is recombinantly produced in cells as described herein, purified, and contacted with a sialtransferase enzyme in vitro to produce Fc region-containing polypeptides containing higher levels of glycans having higher levels of sialic acid on the α 1,3 arms of the branched glycans with a NeuAc-α 2,6-Gal terminal linkage, relative to the reference polypeptide. In some embodiments, a purified reference polypeptide is contacted with the sialtransferase in the presence of CMP-sialic acid, manganese, and/or other divalent metal ions.

A reference Fc region-containing polypeptide can be purified by any method known in the art for purification, for example, by chromatography (e.g., ion exchange, affinity, and sizing column chromatography), centrifugation, differential solubility, or by any other standard technique for the purification of proteins. For example, a reference antibody can be isolated and purified by appropriately selecting and combining affinity columns such as Protein A column with chromatography columns, filtration, ultra filtration, salting-out and dialysis procedures (see Antibodies: A Laboratory Manual, Ed Harlow, David Lane, Cold Spring Harbor Laboratory, 1988). Further, as described herein, a reference polypeptide can be fused to heterologous polypeptide sequences to facilitate purification.

In some embodiments, a polypeptide can be purified using a lectin column by methods known in the art (see, e.g., WO 02/30954). For example, a preparation of polypeptides can be enriched for polypeptides containing glycans having sialic acids in a 2,6 linkage as described in, e.g., WO2008/057634. Following enrichment of polypeptides containing glycans having sialic acids in a 2,6 linkage, the glycan composition of such polypeptides can be further characterized to identify polypeptides having sialic acids attached to the α 1,3 arm of a branched glycan. Preparations of polypeptides containing a predetermined level of glycans having sialic acids in a 2,6 linkage on the α 1,3 arm can be selected for use, e.g., for therapeutic use. Such compositions can have increased levels of anti-inflammatory activity.

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Glycan compositions can be characterized using methods described in, e.g., Barb, Biochemistry 48:9705-9707 (2009); Anumula, J. Immunol. Methods 382:167-176 (2012); Gilar et al., Analytical Biochem. 417:80-88 (2011).

Glycan Evaluation

Glycans of polypeptides can be evaluated using any methods known in the art. For example, sialylation of glycan compositions (e.g., level of branched glycans that are sialylated on an α1,3 arm and/or an α1,6 arm) can be characterized using methods described in, e.g., Barb, Biochemistry 48:9705-9707 (2009); Anumula, J. Immunol. Methods 382: 167-176 (2012); Gilar et al., Analytical Biochem. 417:80-88 (2011); Wuhrer et al., J. Chromatogr. B. 849:115-128 (2007). In some embodiments, in addition to evaluation of sialylation of glycans, one or more parameters described in Table 2 are evaluated.

In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a polypeptide preparation with one or more enzymes under conditions and for a time sufficient to release one or more glycan(s) (e.g., one or more exposed glycan(s)). In some instances, the one or more enzymes include(s) PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1 D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, techniques described herein may be combined with one or more other technologies for the detection, analysis, and or isolation of glycans or polypeptides. For example, in certain instances, glycans are analyzed in accordance with the present disclosure using one or more available methods (to give but a few examples, see Anumula, Anal. Biochem., 350(1):1, 2006; Klein et al., Anal. Biochem., 179:162, 1989; and/or Townsend, R. R. Carbohydrate Analysis" High Performance Liquid Chromatography and Capillary Electrophoresis, Ed. Z. El Rassi, pp 181-209, 1995; WO2008/128216; WO2008/128220; WO2008/128218; WO2008/130926; WO2008/128225; WO2008/130924; WO2008/128221; WO2008/128228; WO2008/128227; WO2008/128230; WO2008/128219; WO2008/128222; WO2010/071817; WO2010/071824; WO2010/085251; WO2011/069056; and WO2011/127322, each of which is incorporated herein by reference in its entirety). For example, in some instances, glycans are characterized using one or more of chromatographic methods, electrophoretic methods, nuclear magnetic resonance methods, and combinations thereof. In some instances, methods for evaluating one or more target protein specific parameters, e.g., in a polypeptide preparation, e.g., one or more of the parameters disclosed herein, can be performed by one or more of following methods.

In some instances, methods for evaluating one or more target protein specific parameters, e.g., in a polypeptide preparation, e.g., one or more of the parameters disclosed herein, can be performed by one or more of following methods.

TABLE 2

Exemplary methods of evaluating parameters:

| Method(s) | Relevant literature | Parameter |
|---|---|---|
| C18 UPLC Mass Spec* | Chen and Flynn, Anal. Biochem., 370:147-161 (2007) Chen and Flynn, J. Am. Soc. Mass Spectrom., 20:1821-1833 (2009) | Glycan(s) (e.g., N-linked glycan, exposed N-linked glycan, glycan detection, glycan identification, and characterization; site specific glycation; glycoform detection (e.g., parameters 1-7); percent glycosylation; and/or aglycosyl) |
| Peptide LC-MS (reducing/non-reducing) | Dick et al., Biotechnol. Bioeng., 100:1132-1143 (2008) Yan et al., J. Chrom. A., 1164:153-161 (2007) Chelius et al., Anal. Chern., 78:2370-2376 (2006) Miller et al., J. Pharm. Sci., 100:2543-2550 (2011) | C-terminal lysine |
| LC-MS (reducing/non-reducing/alkylated) | Dick et al., Biotechnol. Bioeng., 100:1132-1143 (2008) Goetze et al., Glycobiol., 21:949-959 (2011) | |
| Weak cation exchange (WCX) chromatography | Dick et al., Biotechnol. Bioeng., 100:1132-1143 (2008) | |

TABLE 2-continued

Exemplary methods of evaluating parameters:

| Method(s) | Relevant literature | Parameter |
|---|---|---|
| LC-MS (reducing/non-reducing/alkylated) | Dick et al., Biotechnol. Bioeng., 100:1132-1143 (2008) Goetze et al., Glycobiol., 21:949-959 (2011) | N-terminal pyroglu |
| PeptideLC-MS (reducing/non-reducing) | Yan et al., J. Chrom. A., 1164:153-161 (2007) Chelius et al., Anal. Chem., 78:2370-2376 (2006) Miller et al., J. Pharm. Sci., 100:2543-2550 (2011) | |
| Peptide LC-MS (reducing/non-reducing) | Yan et al., J. Chrom. A., 1164:153-161 (2007); Xie et al., mAbs, 2:379-394 (2010) | Methionine oxidation |
| Peptide LC-MS (reducing/non-reducing) | Miller et al., J. Pharm. Sci., 100:2543-2550 (2011) | Site specific glycation |
| Peptide LC-MS (reducing/non-reducing) | Wang et al., Anal. Chem., 83:3133-3140 (2011); Chumsae et al., Anal. Chem., 81:6449-6457 (2009) | Free cysteine |
| Bioanalyzer (reducing/non-reducing)* | Forrer et al., Anal. Biochem., 334:81-88 (2004) | Glycan (e.g., N-linked glycan, exposed N-linked glycan) (including, for example, glycan detection, identification, and characterization; site specific glycation; glycoform detection; percent glycosylation; and/or aglycosyl) |
| LC-MS (reducing/non-reducing/alkylated)* * Methods include removal (e.g., enzymatic, chemical, and physical) of glycans | Dick et al., Biotechnol. Bioeng., 100:1132-1143 (2008) Goetze et al., Glycobiol., 21:949-959 (2011) Xie et al., mAbs, 2:379-394 (2010) | Glycan (e.g., N-linked glycan, exposed N-linked glycan) (including, for example, glycan detection, identification, and characterization; site specific glycation; glycoform detection; percent glycosylation; and/or aglycosyl) |
| Bioanalyzer (reducing/non-reducing) | Forrer et al., Anal. Biochem., 334:81-88 (2004) | Light chain: Heavy chain |
| Peptide LC-MS (reducing/non-reducing) | Yan et al., J. Chrom. A., 1164:153-161 (2007) Chelius et al., Anal. Chem., 78:2370-2376 (2006) Miller et al., J. Pharm. Sci., 100:2543-2550 (2011) | Non-glycosylation-related peptide modifications (including, for example, sequence analysis and identification of sequence variants; oxidation; succinimide; aspartic acid; and/or site-specific aspartic acid) |
| Weak cation exchange (WCX) chromatography | Dick et al., Biotechnol. Bioeng., 100:1132-1143 (2008) | Isoforms (including, for example, charge variants (acidic variants and basic variants); and/or deamidated variants) |
| Anion-exchange chromatography | Ahn et al., J. Chrom. B, 878:403-408 (2010) | Sialylated glycan |
| Anion-exchange chromatography | Ahn et al., J. Chrom. B, 878:403-408 (2010) | Sulfated glycan |
| 1,2-diamino-4,5-methyl-enedioxybenzene (DMB) labeling method | Hokke et al., FEBS Lett., 275:9-14 (1990) | Sialic acid |
| LC-MS | Johnson et al., Anal. Biochem., 360:75-83 (2007) | C-terminal amidation |
| LC-MS | Johnson et al., Anal. Biochem., 360:75-83 (2007) | N-terminal fragmentation |
| Circular dichroism spectroscopy | Harn et al., Current Trends in Monoclonal Antibody Development and Manufacturing, S. J. Shire et al., eds, 229-246 (2010) | Secondary structure (including, for example, alpha helix content and/or beta sheet content) |
| Intrinsic and/or ANS dye fluorescence | Harn et al., Current Trends in Monoclonal Antibody Development and Manufacturing, S. J. Shire et al., eds, 229-246 (2010) | Tertiary structure (including, for example, extent of protein folding) |
| Hydrogen-deuterium exchange-MS | Houde et al., Anal. Chem., 81:2644-2651 (2009) | Tertiary structure and dynamics (including, for example, accessibility of amide protons to solvent water) |
| Size-exclusion chromatography | Carpenter et al., J. Pharm. Sci., 99:2200-2208 (2010) | Extent of aggregation |
| Analytical ultra-centrifugation | Pekar and Sukumar, Anal. Biochem., 367:225-237 (2007) | |

References listed in Table 2 are hereby incorporated by reference in their entirety or, in the alternative, to the extent that they pertain to one or more of the methods disclosed in Table 2. Other methods for evaluating one or more parameters are disclosed in the examples.

III. Treatment of Neurodegeneration

The inventors have discovered that sialic acid-mediated biological activity of Fc-containing molecules is not only due to the level of sialylation, but due to particular branching arrangements. Accordingly, Fc region-containing polypeptides described herein (e.g., Fc region-containing polypeptides containing glycans containing sialic acid on α 1,3 arms of branched glycans with a NeuAc-α 2,6-Gal terminal linkage) have increased activity relative to a reference polypeptide.

In some embodiments, Fc region-containing polypeptides having sialic acids in both the α 1,3 and α 1,6 arms of branched glycans may be useful in the treatment of neurodegeneration.

IV. Pharmaceutical Compositions and Administration

A polypeptide of the present disclosure, e.g., an Fc region-containing polypeptide comprising branched glycans that are sialylated on an α 1,3 arm of the branched glycan in the Fc region, e.g., with a NeuAc-α 2,6-Gal terminal linkage, can be incorporated into a pharmaceutical composition and can be useful in the treatment of neurodegeneration.

Such a pharmaceutical composition is useful as an improved composition for the prevention and/or treatment of diseases relative to the corresponding reference polypeptide. Pharmaceutical compositions comprising a polypeptide can be formulated by methods known to those skilled in the art. The pharmaceutical composition can be administered parenterally in the form of an injectable formulation comprising a sterile solution or suspension in water or another pharmaceutically acceptable liquid. For example, the pharmaceutical composition can be formulated by suitably combining the sulfated polypeptide with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Non-limiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampoule.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the patient. A single dose of the pharmaceutical composition containing a modified polypeptide can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

EXAMPLES

Example 1—Galactosylation and Sialylation of IVIG

The sialylation of IVIG by the sialyltransferase ST6 was analyzed. IVIG was first galactosylated and then sialylated. The reactions were performed sequentially. There was no purification between galactosylation and sialylation reactions. The relative abundance of glycoforms was analyzed following the sialylation reactions.

A. Galactosylation

A reaction was set up that contained the following components at the concentrations indicated:

| Constituent | Final concentration |
| --- | --- |
| MOPS (pH 7.4) | 25 mM |
| MnCl$_2$ | 10 mM |
| IVIG | 12.5 mg/ml |
| B4GalT1 (90 u/ml) | 400 mu/ml |
| UDP-Galactose | 50 mM |

The reaction was incubated for 72 hours at 37° C.

B. Sialylation

To an aliquot of the galactosylation reaction were added CMP-NANA, MOPS buffer and ST6Gal1. The final volume was adjusted so that the final concentration of components in the reaction was as indicated.

| Constituent | Final concentration |
| --- | --- |
| MOPS (pH 7.4) | 50 mM |
| MnCl$_2$ | 8 mM |
| IVIG | 10 mg/ml |
| CMP-NANA | 20 mM |
| ST6Gal1 (SEQ ID NO: 3) | 0.6 mg ST6/mg IVIG |

The reaction was incubated at 37° C. Aliquots were extracted at the times indicated in FIG. 2 and frozen at −20° C. for later analyses.

C. Results

Figure 5:
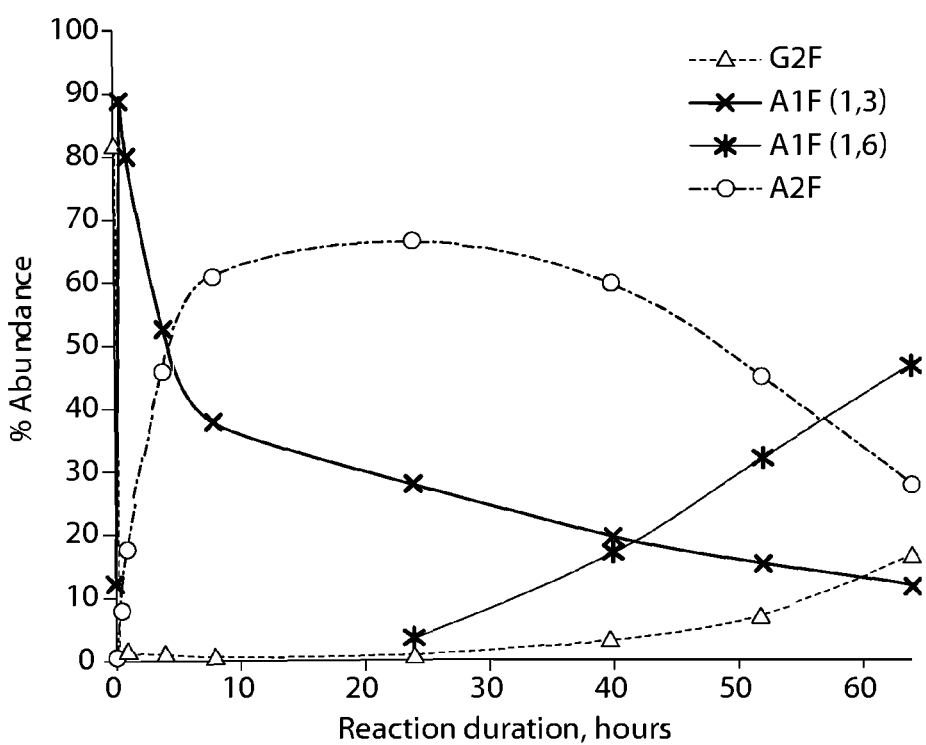
FIG. 5 is a graphic representation of relative abundance of glycans at various times during a sialylation reaction with ST6 sialyltransferase.

As shown in FIG. 5, the predominant glycoform changed over time from G2F to A1F (1,3) to A2F to A1F (1,6). The results are summarized in the reaction scheme depicted in FIG. 4. As shown in FIG. 4, the product glycoform can change between G2F, A1F (1,3), A2F, and A1F (1,6) during the course of a reaction due to competing addition (forward reaction) and removal (back reaction) steps.

The sialyltransferase ST6 can add sialic acid to either branch of a substrate's biantennary N-glycan. However, these results demonstrate that addition to each branch happens at different rates, resulting in different end products depending on the reaction conditions. Addition of sialic acid to the α 1,3 branch is much faster than addition to the α1,6 branch.

These data also demonstrate that sialyltransferase ST6 can also catalyze the removal of sialic acids from N-glycans. The removal of sialic acid from the α 1,3 branch is much faster than removal from the α 1,6 branch. This can surprisingly lead to the production of Fc glycans substantially or primarily monosialylated on the α 1,6 branch by modulating reaction conditions.

This Example demonstrates that reaction conditions can be controlled to produce a glycoprotein product having a predetermined sialylation levels. Such conditions can include time, ST6 sialyltransferase concentration, substrate concentration, donor sugar nucleotide concentration, product nucleotide concentration, pH, buffer composition, and/or temperature.

Example 2—Treatment of Neurodegeneration with Sialylated IVIG

To test the efficacy and mechanisms of action of these agents in Alzheimer's disease (AD) and other neurodegenerative diseases, IVIG a 2,6 sialylated on the N-linked biantennary glycan at ASN-297 in the Fc region was administered to mice with experimental autoimmune encephalitis.

The specific sialylated preparations of IVIG tested in these studies include:

1) Monosialylated (s1) IVIG is a preparation where 63-79 percent of the Fc glycans are sialylated exclusively on the α 1,3 arm, fucosylated, and not bisected. Less than 15% of the Fc glycans are sialylated exclusively on the α 1,6 arm, fucosylated, and not bisected. Less than 15% of the Fc glycans are sialylated on both the α 1,3 and α 1,6 arms, fucosylated, and not bisected. Bisected species and afucosylated species, all of which are minor components, were likewise sialylated predominately on the α 1,3 arm only.

2) Disialylated (s2) IVIG is a preparation where 87 percent of the Fc glycans are sialylated on both the α 1,3 and α 1,6 arms, fucosylated, and not bisected. Less than 6% of the Fc glycans are sialylated on the α 1,3 arm, fucosylated, and not bisected. Fc glycans sialylated on the α 1,6 arm, fucosylated, and not bisected were not detected. Bisected species and afucosylated species, all of which are minor components, were likewise sialylated predominately on both arms.

Experimental autoimmune encephalomyelitis (EAE) is the most commonly used model of CNS autoimmunity, demyelination, cell trafficking, and tolerance induction.

EAE is mediated by myelin-specific $CD4^+$ T cells but is also characterized by a critical involvement of the innate immune compartment, especially monocytes, macrophages, dendritic cells and microglia. EAE induces inflammatory infiltration of the CNS through the blood-brain barrier. Also, damage in the CNS in EAE is driven by adaptive immune cells (T cells) and microglia, CNS-specific innate immune cells.

EAE was induced in C57BL/6 mice by subcutaneous immunization with the myelin oligodendrocyte protein $(MOG)_{35-55}$ peptide in a complete Freund's adjuvant (CFA) emulsion, followed by administration of Pertussis Toxin (PTX). Typically, EAE developed 8-10 days after immunization and was characterized by an ascending paralysis, starting with the loss of tail tone.

Mice were injected subcutaneously at two sites in the back with the $MOG_{35-55}$/CFA Emulsion. One site of injection was in the area of upper back, approximately 1 cm caudal of the neck line. The second site was in the area of lower back, approximately 2 cm cranial of the base of the tail. The injection volume was 0.1 mL at each site.

Within 2 hours of the injection of emulsion, and then again 24 hours after immunization, 0.1 ml (143 ng) PTX was administered intraperitoneally (i.p.).

Mice were scored on a scale from 0 to 5, as follow, by a person unaware of both treatment and of previous scores for each mouse.

0 No signs of disease

1 Limp tail. When the mouse was picked up by the tail, instead of being erect, the whole tail draped over finger.

2 Limp tail and weakness of hind legs. When mouse was picked up by tail, legs are not spread apart, but held closer together. When the mouse was observed walking, it had a clearly apparent wobbly walk.

3 Limp tail and complete paralysis of hind legs (most common) OR Limp tail with paralysis of one front and one hind leg OR ALL of:
Severe head tilting,
Walking only along the edges of the cage,
Pushing against the cage wall,
Spinning when picked up by the tail.

4 Limp tail, complete hind leg and partial front leg paralysis. Mouse was minimally moving around the cage but appears alert and feeding. Usually, euthanasia was recommended after the mouse scores level 4 for 2 days. When the mouse was euthanized because of severe paralysis, score of 5 was entered for that mouse for the rest of the experiment.

5 Moribund or dead.

Figure 6:
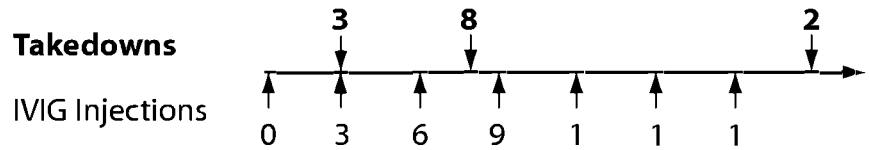
FIG. 6 is an image displaying the experimental design.

Mice were dosed i.p. Q3D, starting at the day of immunization (FIG. 6). Tissues were harvested at 3 days (one injection), 8 days (3 injections) and at the end point of the experiment (d21; 7 injections). 8 C57Bl/6 females were used per condition (per time point and per treatment).

These experiments aim to compare the efficacy of IVIG and sialylated IVIG (s1 and s2) at modulating clinical EAE scores as well as cellular and molecular readouts. Readouts include clinical scores, FACS analysis, Luminex, shotgun proteomics and quantitative RT-PCR. Tissues analyzed include Blood (FACS), serum (Luminex), Spleen (FACS/Proteomics/qRT-PCR), Lymph nodes (Proteomics), Bone marrow (FACS/qRT-PCR/Proteomics) and Spinal cord (FACS).

Methods

FACS

Tissues were processed and filtered through a 70 □m strainer. Red blood cells (spleen/blood) were lysed for 10 min. at 4° C. Samples were then resuspended in FACS buffer and plated in a V-bottom 96 well plate Fc receptors were blocked for 10 min in FBS and stained for 20 min in various antibody cocktails (Table 3) at 4° C. Samples were resuspended in 1% PFA. Data was acquired using a FACS Verse (Becton Dickinson) and analyzed using the FlowJo software (TreeStar).

TABLE 3

Antibody cocktails

| Label | T cells | Myeloid cells | CNS Infiltrating cells |
|---|---|---|---|
| FITC | FoxP3 | Ly-6C | CD4 |
| PE | CD25 | Ly-6G | GR-1 |
| PerCP-Cy5.5 | CD4 | CD11C | CD11c |
| PE-Cy7 | CD62L | CD62L | CD45 |
| APC | CD44 | CCR2 | CCR2 |
| APC-Cy7 | CD8 | CD11b | CD11b |
| V450 | CD3 | Live/Dead | Live/Dead |
| V500 | | | I-A/I-E |

Luminex

Millipore's MILLIPLEX™ Mouse Cytokine/Chemokine kit was used to quantify the following 32 mouse cytokines and chemokines from plasma: Eotaxin, G-CSF, GM-CSF, IFN□, IL-1□, IL-1□, IL-2, IL-3, IL-4, IL-5, IL-6, IL-7, IL-9, IL-10, IL-12(p40), IL-12(p70), IL-13, IL-15, IL-17, IP-10, KC, LIF, LIX, MCP-1, M-CSF, MIG, MIP-1□, MIP-1□, MIP-2, RANTES, TNF□, and VEGF.

Characterization of the Clinical Efficacy of IVIG and s1-IVIG in EAE

Figure 7:
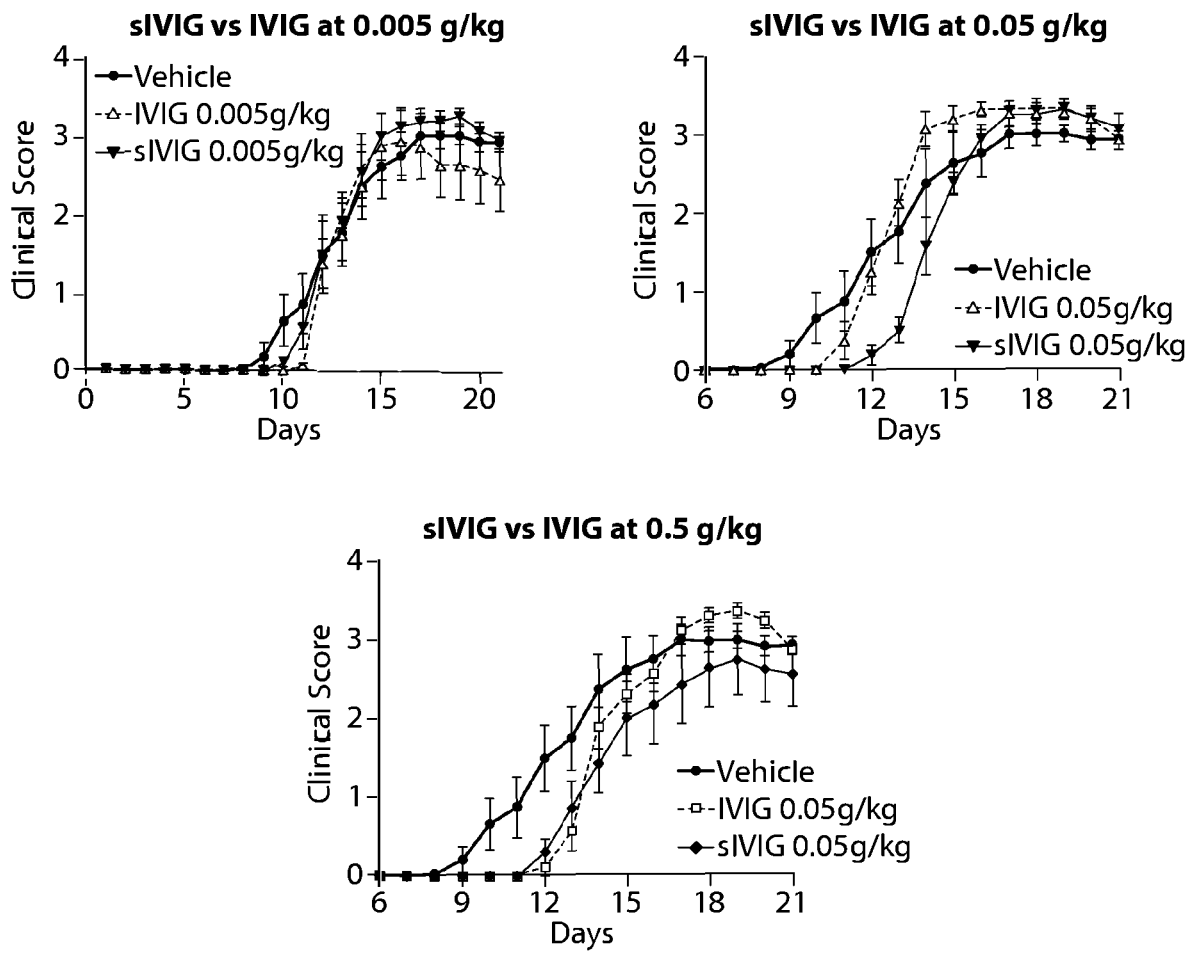
FIG. 7 is an image displaying the clinical course of EAE.

Both IVIG and sIVIG treatments appeared to have postponed EAE onset in a dose-dependent fashion (FIG. 7). Neither agent showed a statistically significant decrease in maximal EAE severity (MMS). For delay of disease onset, IVIG and s1-IVIG appeared to be equally effective at 0.5 g/kg, but s1-IVIG at 0.05 g/kg was as effective as IVIG at a dose of 0.5 g/kg. However, no statistically significant differences regarding EAE onset or EAE severity were observed between the vehicle treated group and either the IVIG or s1-IVIG treated groups at 0.005 g/kg (Table 4). These results demonstrate the increased potency of s1-IVIG which was effective in delaying disease onset at 0.05 g/kg while IVIG was not effective at this dose, but did reach this level of efficacy at the 0.5 g/kg dose.

TABLE 4

Statistical analysis of clinical EAE. Comparison of Incidence, Median Day of onset and Mean Maximal clinical score (MMS).

| Treatment | EAE incidence (%) | P value | Median day of onset | p value | MMS +/− SD | p value |
|---|---|---|---|---|---|---|
| Vehicle | 100.0 | | 11.5 | | 3.38 +/− 0.31 | |
| IVIG, 0.5 g/kg | 100.0 | 1.0000 | 13.0 | 0.1774 | 3.38 +/− 0.23 | 0.7398 |
| IVIG, 0.05 g/kg | 100.0 | 1.0000 | 12.0 | 0.9383 | 3.50 +/− 0.00 | 0.2361 |
| IVIG, 0.005 g/kg | 87.5 | 0.1667 | 12.0 | 0.5337 | 3.00 +/− 1.22 | 0.6192 |
| s1-IVIG, 0.5 g/kg | 87.5 | 0.1667 | 13.0 | 0.1274 | 2.88 +/− 1.22 | 0.2641 |
| s1-IVIG, 0.05 g/kg | 100.0 | 1.0000 | 13.0 | 0.1896 | 3.38 +/− 0.35 | 0.8522 |
| s1-IVIG, 0.005 g/kg | 100.0 | 1.000 | 11.5 | 0.93860 | 3.44 +/− 0.18 | 0.7561 |

Modulation of T Cell Differentiation by IVIG, s1-IVIG or s2-IVIG

Figure 8A:
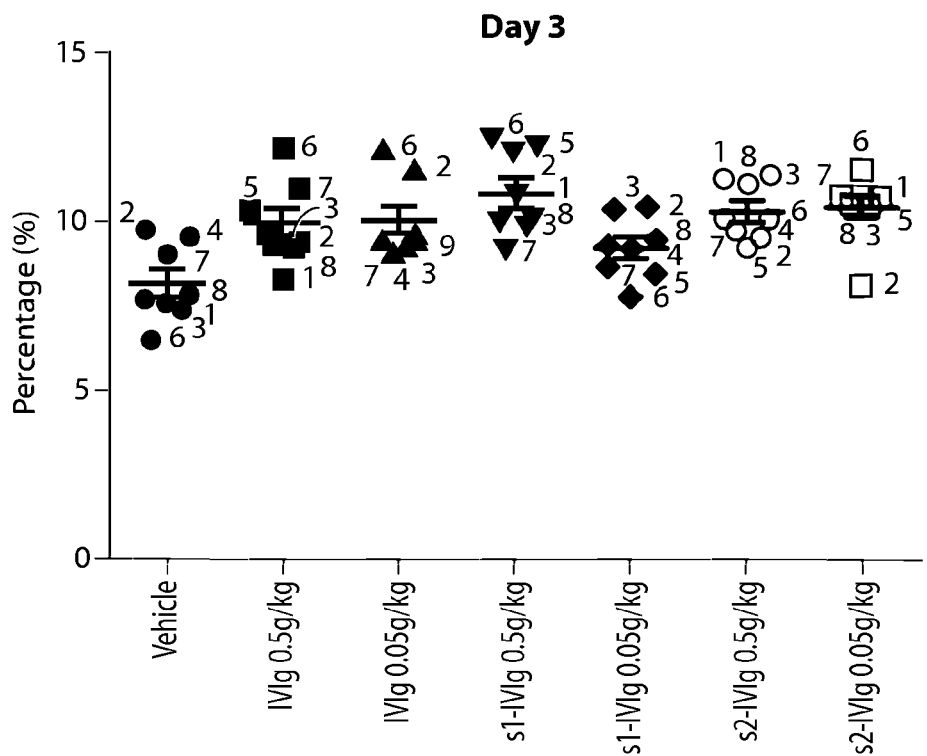
FIGS. 8A and 8B are images displaying the increased frequency of T cells in the spleen following treatment.
Figure 8B:
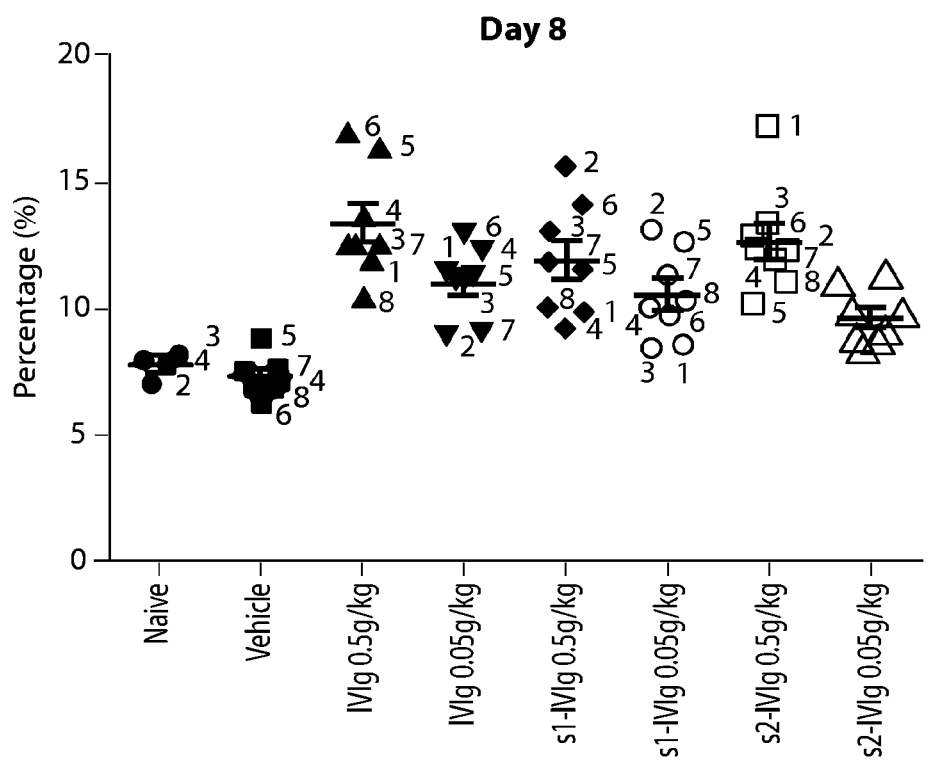
Figure 9A:
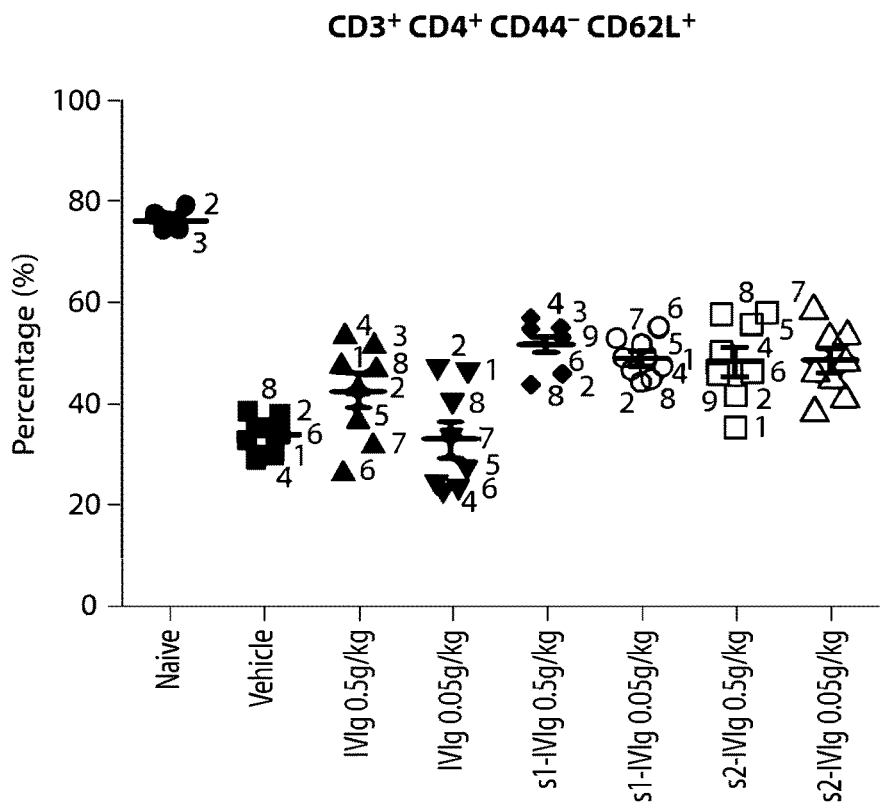
FIGS. 9A-9D are images displaying the increased frequency of naïve T cells and decreased frequency of memory T cells following treatment.
Figure 9B:
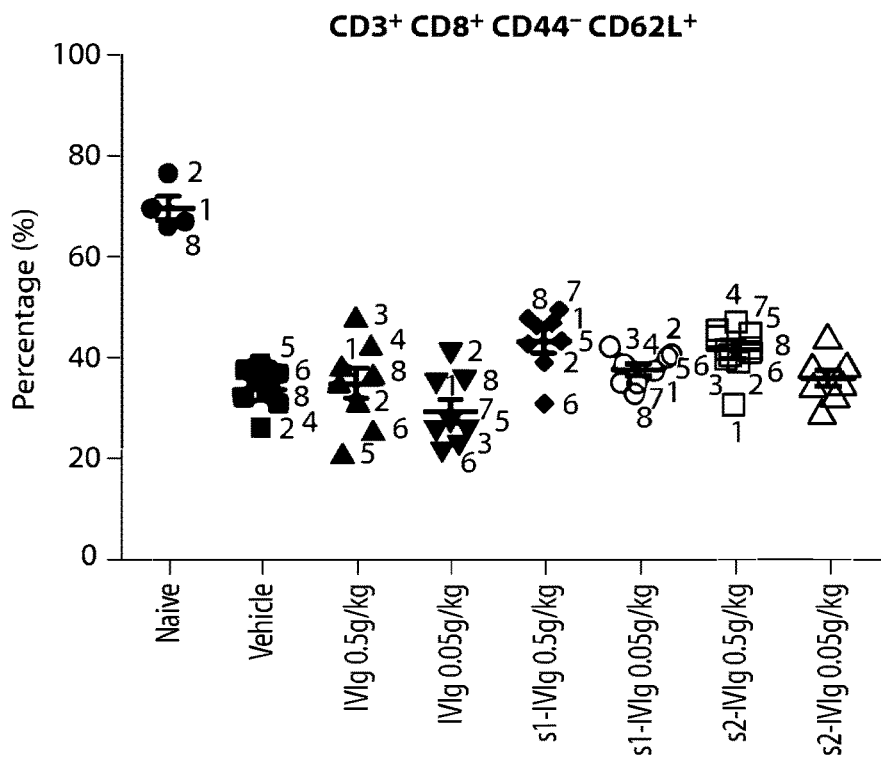
Figure 9C:
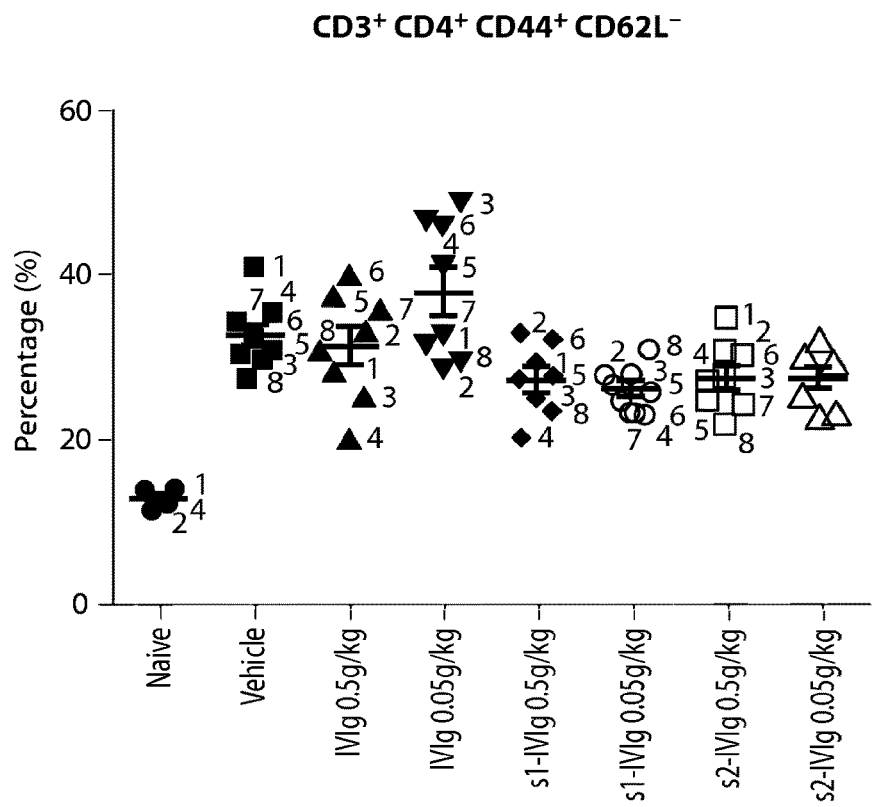
Figure 9D:
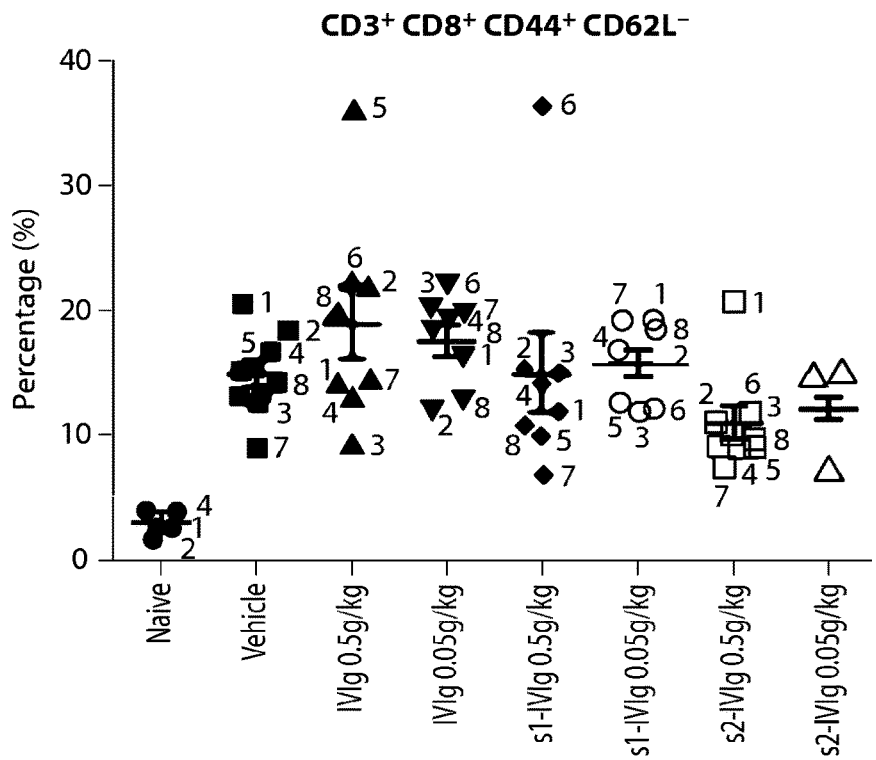

We found that $CD3^+CD4^+CD25^+FoxP3^+$ regulatory T cells were increased in the spleen following IVIG, s1- and s2-IVIG treatment after only one injection (d3). This increased frequency is maintained and potentiated at day 8 post-immunization (FIGS. 8A and 8B). No difference was observed between the IVIG, s1- and s2-IVIG groups.

EAE is dependent on T cell activation and differentiation. The frequency of $CD44^-CD62L^+$ $CD4^+$ and $CD8^+$ naïve T cells is reduced following EAE induction (FIGS. 9A-9D). However, the frequency of both $CD4^+$ and $CD8^+$ naïve T cells was significantly elevated following s1- and s2-IVIG compared to vehicle and IVIG treatment. Conversely, the frequency of both $CD4^+$ and $CD8^+CD44^+CD62L^-$ effector memory cells was significantly more reduced in s1-IVIG and s2-IVIG-treated groups.

This result suggests that s1- and s2-IVIG are significantly more potent than IVIG at preventing T cell activation. These results could be beneficial in AD considering the alteration of the memory cell compartment associated with the disease.

Figure 10A:
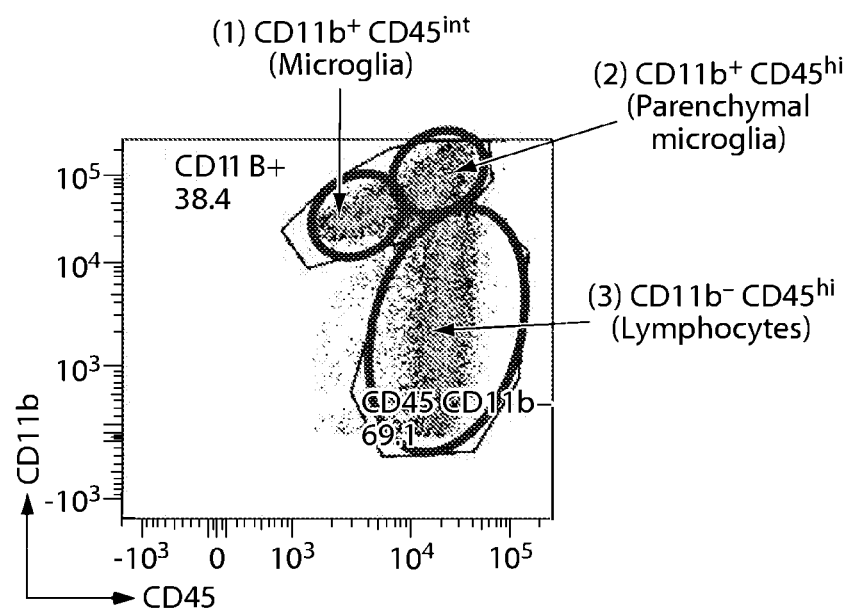
FIGS. 10A-10E are images displaying characterization of CNS populations using FACS analysis.

Modulation of Myeloid Cell Differentiation and Activation by IVIG, s1-IVIG or s2-IVIG Microglia are often found near damaged tissue in AD patients. Studies have shown that microglia play opposite roles in disease pathogenesis by eliminating beta-amyloid aggregates via phagocytosis but also by killing nearby neurons through the release of neurotoxic factors. Microglia can be subdivided in two different subsets: resident microglia and parenchymal microglia (FIG. 10A). Parenchymal microglia originate from the extravasation of peripheral monocytes through the blood brain barrier and are influenced by chemotactic gradients.

Expression of CCR2, a chemokinereceptor on monocytes and parenchymal microglia, has been demonstrated to play a positive role in the clearance of Aβ plaques in a mouse model of AD by promoting the infiltration of monocytes into the CNS.

Figure 10B:
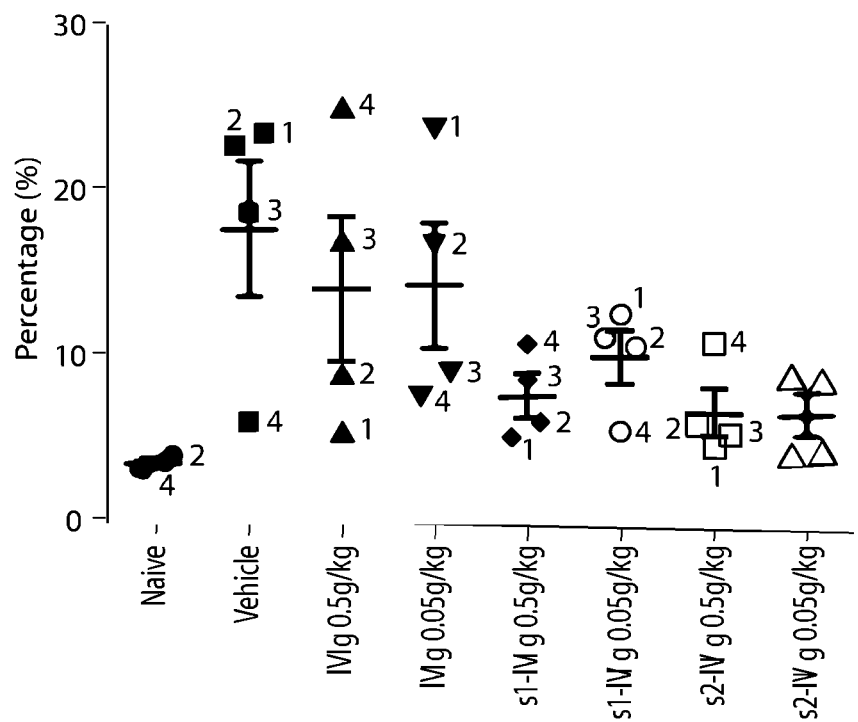
Figure 10C:
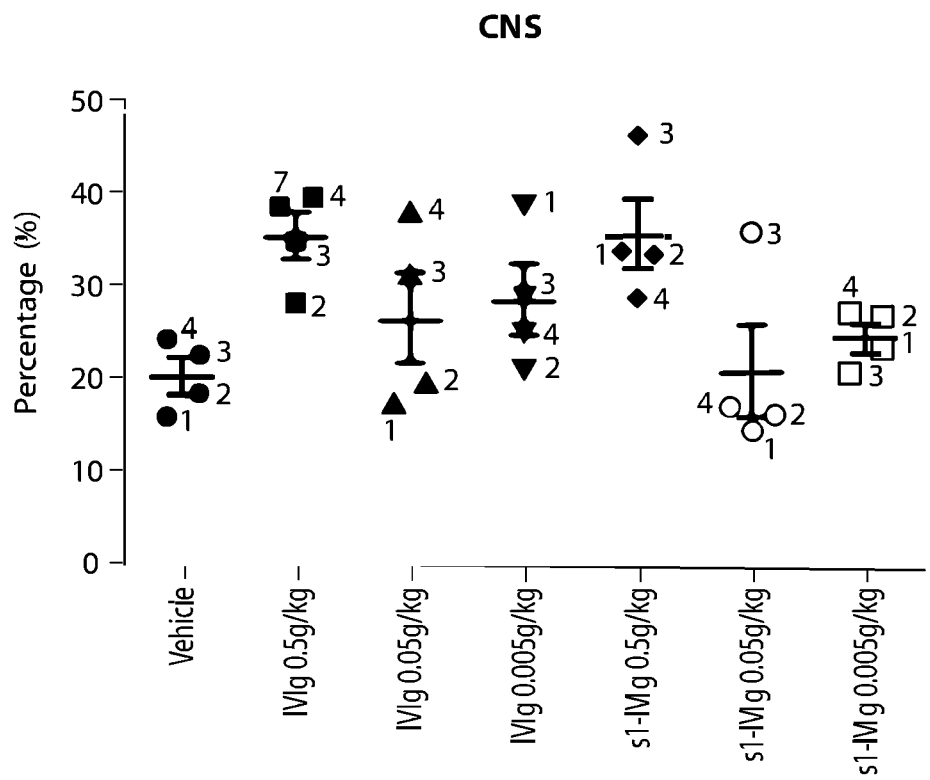
Figure 10D:
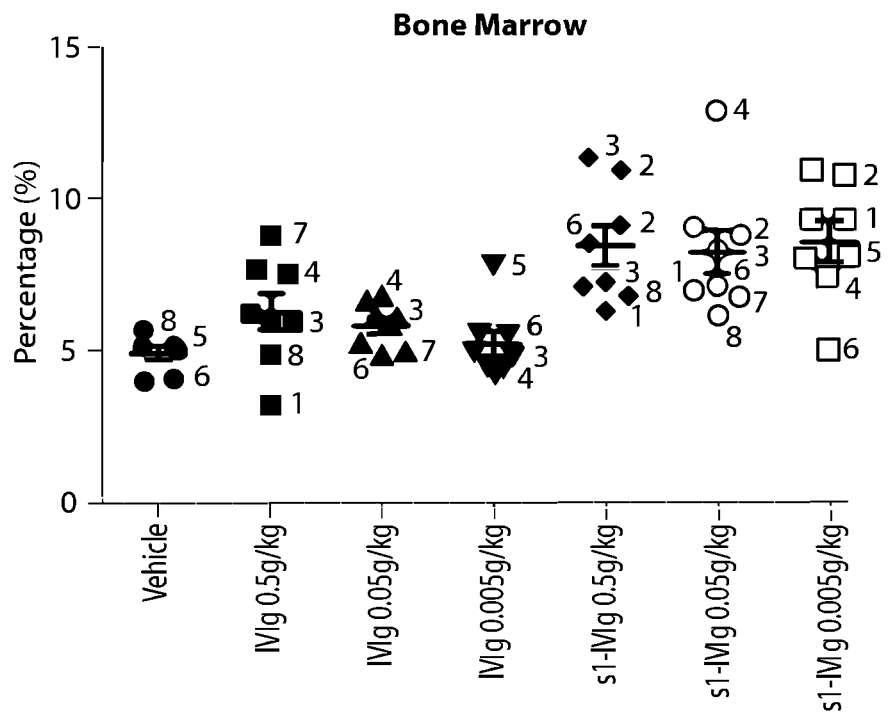
Figure 10E:
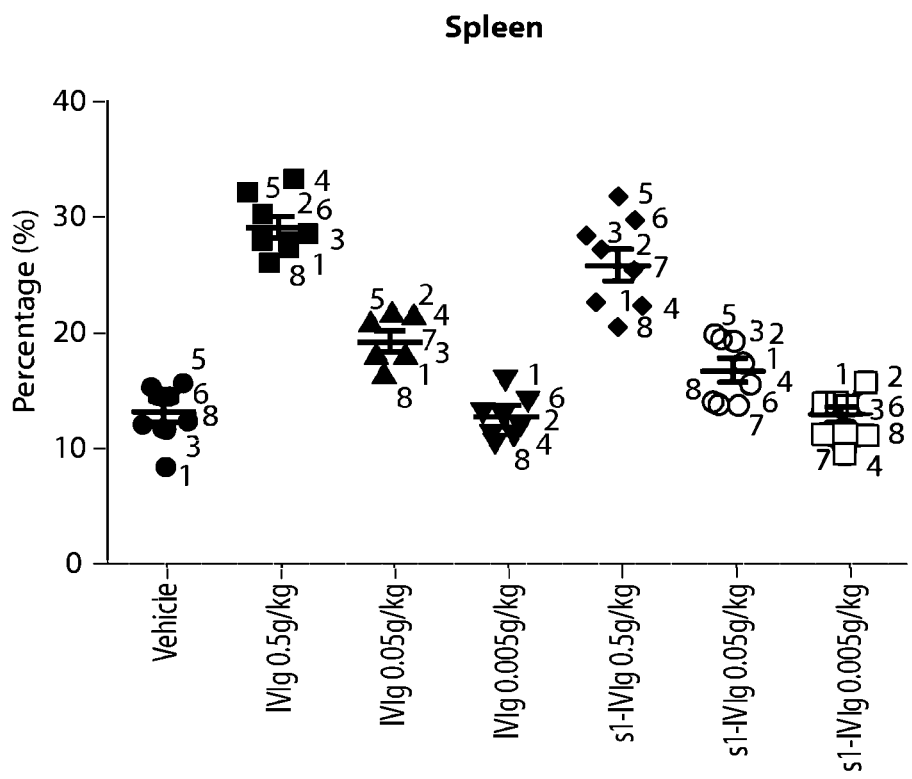

In our model, we observed a reduction of the frequency of parenchymal microglia in the CNS, following treatment with s1- and s2-IVIG (FIG. 10B). Treatment with IVIG and sialylated IVIG was associated with a higher frequency of CCR2 positive cells in the CNS (FIG. 10C), but also in periphery (bone marrow (FIG. 10D) and spleen (FIG. 10E). These results suggest an increased ability for sialylated IVIG to positively regulate microglial mechanisms beneficial for the removal of neurodegenerative plaque as well as to decrease the percentage of detrimental inflammatory microglia.

Modulation of chemokine expression by IVIG and s1-IVIG Similar to many other diseases which involve neurodegeneration, such as amyotrophic lateral sclerosis (ALS) and Huntington disease (HD), the blood brain barrier is intact in AD. Chronic inflammatory responses are believed to be caused by resident CNS cells. An impressive number of chemokines and receptors have been found in resident CNS cells, including MCP-1 and eotaxin, which both are CCR2 ligands.

MCP-1 is involved in monocyte trafficking. In AD, it has been found in mature, but not in immature, senile plaques and in reactive microglia of brain tissues from patients, suggesting that it may contribute to the maturation of senile plaques. Serum levels have been shown to be increased in patients transitioning from mild cognitive impairment (MCI) to AD Concentrations of eotaxin were previously shown to be elevated in serum from AD patients and increased levels of eotaxin may be associated with aging. Also, a role for eotaxin was recently demonstrated in neurogenesis. Therefore, inhibition of both MCP-1 and eotaxin may decrease plaques and preserve neurons in aging.

Figure 11A:
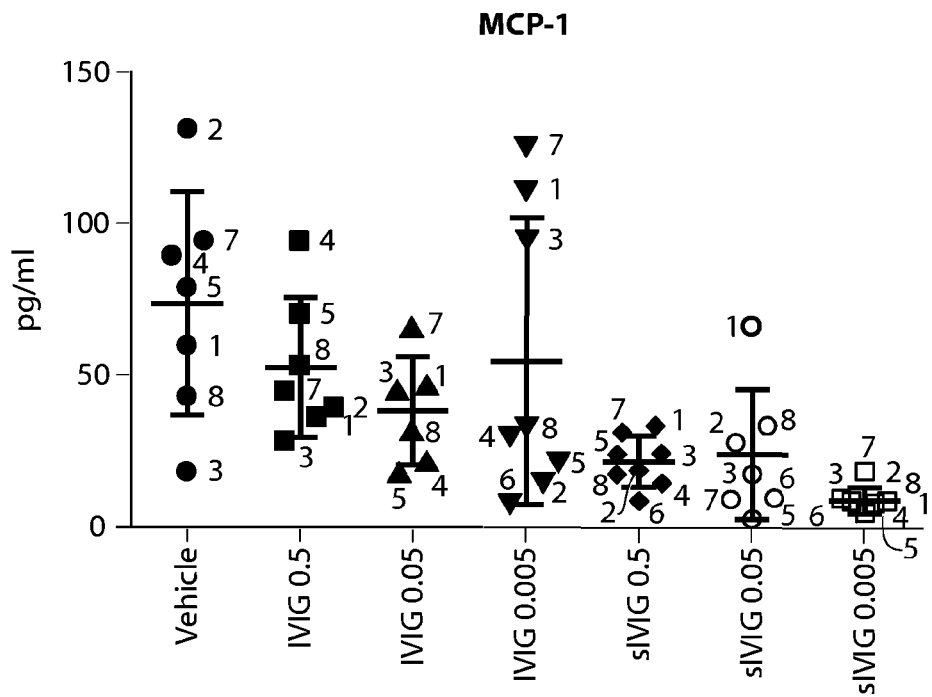
FIGS. 11A and 11B are images displaying the expression levels CCL2 (MCP-1) and Eotaxin following treatment.

Levels of MCP-1 were significantly reduced in the s1-IVIG-treated group, compared to vehicle (FIG. 11A), suggesting a role for sialylation in regulating the expression of this chemokine.

Figure 11B:
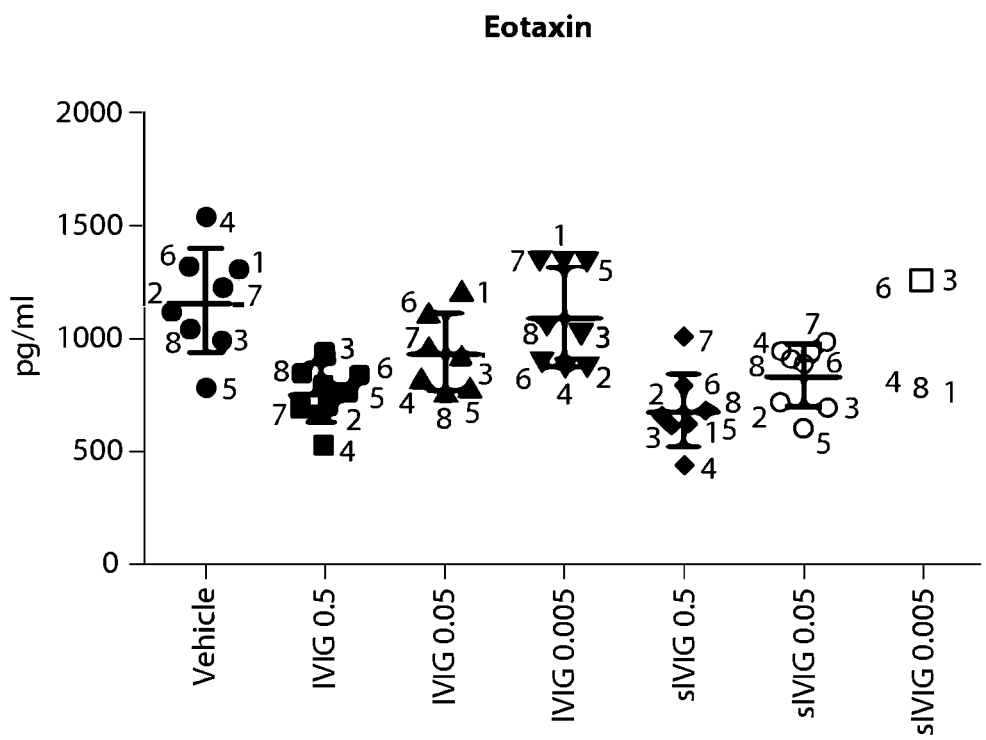

Levels of eotaxin were reduced in both IVIG and s1-IVIG 0.5 g/kg groups (FIG. 11B). This result suggests a role for IVIG in regulating the expression of the cytokine, but not necessarily for sialylation.

Relevance to Neurodegeneration for Sialylated IVIG
  Reduction of CNS infiltration: reduction of CNS/PNS inflammation.
  Increased expression of CCR2: increased ability for plaque clearance/lesion resorption.
  Increased regulatory T cell differentiation: regulation of inflammation/T cell activation.
  Decreased memory T cell differentiation (and conversely increased naïve phenotype): reduction of inflammation and migration to CNS/PNS.
  Reduction of MCP-1 expression: decreased migration of monocytes to the CNS/PNS. Decreased secretion of pro-inflammatory cytokines (IL-1).
  Reduction of Eotaxin levels: improved neurogenesis.

While the methods have been described in conjunction with various instances and examples, it is not intended that the methods be limited to such instances or examples. On the contrary, the methods encompass various alternatives, modifications, and equivalents, as will be appreciated by those of skill in the art.

What is claimed is:

1. A method for treating neurodegeneration, the method comprising administering to a subject in need thereof a preparation comprising a therapeutically effective amount of sialylated pooled polyvalent IgG, wherein at least 87% of the branched glycans on the Fc region of the pooled polyvalent IgG in the preparation are sialylated on both the α1,3 arm and the α1,6 arm of the branched glycan via a NeuAc-α2,6-Gal terminal linkage.

2. The method of claim 1, wherein said neurodegeneration is related to a disease selected from the group consisting of age-related dementia, Amyotrophic lateral sclerosis (ALS), cerebellar ataxia, Creutzfedt-Jakob disease, Down's syndrome, frontotemporal lobar degenerations/dementia, Huntington's disease, inclusion body myositis, Lewy body dementia, Guillain-Barré syndrome, Charcot-Marie-Tooth syndrome, myasthenia gravis, Lambert-Eaton myasthenic syndrome, multiple sclerosis, multiple-system atrophy, Parkinson's disease, vascular dementia, Lennox-Gastaut syndrome, ataxia telangiectasia, neurodegenerative Lyme disease, acute disseminating encephalomyelitis, acute idiopathic dysautonomia, adrenoleukodystrophy, demyelinative brain stem encephalitis, demyelinating neuropathy associated with monoclonal IgM, HTLV-1-associated myelopathy, other paraneoplastic neurodegeneration, neuropathy or encephalopathies, lumbosacral or brachial plexitis, POEMS syndrome, post-infection cerebellar ataxia, presbycusis, spinocerebellar ataxia, peripheral neuropathy and vascular dementia.

3. The method of claim 1, wherein the preparation is administered by parenteral administration, transnasal administration, transpulmonary administration, or transcutaneous administration.

4. The method of claim 3, wherein the preparation is systemically administered by intravenous injection, intramuscular injection, intraperitoneal injection, or subcutaneous injection.

5. The method of claim 3, wherein the preparation is locally administered by intravenous injection, intramuscular injection, intraperitoneal injection, or subcutaneous injection.

6. The method of claim 1, wherein the preparation is incorporated in a pharmaceutical composition further comprising a pharmaceutically acceptable vehicle or media.

7. The method of claim 1, wherein the preparation is formulated in a sterile composition for injection further comprising a pharmaceutically acceptable vehicle.

8. The method of claim 1, wherein the branched glycans are sialylated in a reaction under conditions wherein the rate of transfer of sialic acid to the α1,3 arm is greater than the rate of removal of a sialic acid from the α1,3 arm.

9. The method of claim 8, wherein the reaction comprises combining ST6Gal1 and IVIG in a ratio of 0.6 mg ST6Gal1 to 1 mg IVIG.

10. The method of claim 8, wherein the reaction proceeds for no more than 50 hours at 37° C.

11. The method of claim 1, wherein the branched glycans are sialylated in a reaction under conditions wherein the rate of transfer of sialic acid to the α1,6 arm is greater than the rate of removal of sialic acid from the α1,6 arm.

12. The method of claim 11, wherein the reaction comprises combining ST6Gal1 and IVIG in a ratio of 0.6 mg ST6Gal1 to 1 mg IVIG.

13. The method of claim 11, wherein the reaction proceeds for no more than 50 hours at 37° C.

14. The method of claim 1, wherein the branched glycans are sialylated in a reaction under conditions wherein:
the rate of transfer of sialic acid to the α1,3 arm is greater than the rate of removal of sialic acid from the α1,3 arm; and
the rate of transfer of sialic acid to the α1,6 arm is greater than the rate of removal of sialic acid from the α1,6 arm.

15. The method of claim 14, wherein ST6Gal1 is added to IVIG at a ratio of 0.6 mg ST6Gal1 to 1 mg IVIG.

16. The method of claim 14, wherein the reaction proceeds for no more than 50 hours at 37° C.

* * * * *

SEQUENCE LISTING

<160> NUMBER OF SEQ ID NOS: 3

<210> SEQ ID NO 1
<211> LENGTH: 375
<212> TYPE: PRT
<213> ORGANISM: Homo sapiens

<400> SEQUENCE: 1

Gly Ser Tyr Tyr Asp Ser Phe Lys Leu Gln Thr Lys Glu Phe Gln Val
1               5                   10                  15

Leu Lys Ser Leu Gly Lys Leu Ala Met Gly Ser Asp Ser Gln Ser Val
            20                  25                  30

Ser Ser Ser Ser Thr Gln Asp Pro His Arg Gly Arg Gln Thr Leu Gly
        35                  40                  45

Ser Leu Arg Gly Leu Ala Lys Ala Lys Pro Glu Ala Ser Phe Gln Val
    50                  55                  60

Trp Asn Lys Asp Ser Ser Lys Asn Leu Ile Pro Arg Leu Gln Lys
65                  70                  75                  80

Ile Trp Lys Asn Tyr Leu Ser Met Asn Lys Tyr Lys Val Ser Tyr Lys
                85                  90                  95

Gly Pro Gly Pro Gly Ile Lys Phe Ser Ala Glu Ala Leu Arg Cys His
            100                 105                 110

Leu Arg Asp His Val Asn Val Ser Met Val Glu Val Thr Asp Phe Pro
        115                 120                 125

Phe Asn Thr Ser Glu Trp Glu Gly Tyr Leu Pro Lys Glu Ser Ile Arg
    130                 135                 140

Thr Lys Ala Gly Pro Trp Gly Arg Cys Ala Val Val Ser Ser Ala Gly
145                 150                 155                 160

Ser Leu Lys Ser Ser Gln Leu Gly Arg Glu Ile Asp His Asp Ala
                165                 170                 175

Val Leu Arg Phe Asn Gly Ala Pro Thr Ala Asn Phe Gln Gln Asp Val
            180                 185                 190

Gly Thr Lys Thr Thr Ile Arg Leu Met Asn Ser Gln Leu Val Thr Thr
        195                 200                 205

Glu Lys Arg Phe Leu Lys Asp Ser Leu Tyr Asn Glu Gly Ile Leu Ile
    210                 215                 220

Val Trp Asp Pro Ser Val Tyr His Ser Asp Ile Pro Lys Trp Tyr Gln
225                 230                 235                 240

Asn Pro Asp Tyr Asn Phe Phe Asn Asn Tyr Lys Thr Tyr Arg Lys Leu
                245                 250                 255

His Pro Asn Gln Pro Phe Tyr Ile Leu Lys Pro Gln Met Pro Trp Glu
            260                 265                 270

Leu Trp Asp Ile Leu Gln Glu Ile Ser Pro Glu Glu Ile Gln Pro Asn
        275                 280                 285

Pro Pro Ser Ser Gly Met Leu Gly Ile Ile Ile Met Met Thr Leu Cys
    290                 295                 300

Asp Gln Val Asp Ile Tyr Glu Phe Leu Pro Ser Lys Arg Lys Thr Asp
305                 310                 315                 320

Val Cys Tyr Tyr Gln Lys Phe Phe Asp Ser Ala Cys Thr Met Gly
                325                 330                 335

Ala Tyr His Pro Leu Leu Tyr Glu Lys Asn Leu Val Lys His Leu Asn
            340                 345                 350

Gln Gly Thr Asp Glu Asp Ile Tyr Leu Leu Gly Lys Ala Thr Leu Pro
        355                 360                 365

Gly Phe Arg Thr Ile His Cys
    370                 375

<210> SEQ ID NO 2
<211> LENGTH: 402
<212> TYPE: PRT
<213> ORGANISM: Homo sapiens

<400> SEQUENCE: 2

Met Ile His Thr Asn Leu Lys Lys Phe Ser Tyr Phe Ile Leu Ala
1               5                   10                  15

Phe Leu Leu Phe Ala Leu Ile Cys Val Trp Lys Lys Gly Ser Tyr Glu
                20                  25                  30

Ala Leu Lys Leu Gln Ala Lys Glu Phe Gln Val Thr Lys Ser Leu Glu
                35                  40                  45

Lys Leu Ala Ile Gly Ser Gly Ser Gln Ser Thr Ser Ala Ser Ile Lys
50                  55                  60

Gln Asp Ser Lys Pro Gly Ser Gln Val Leu Ser His Leu Arg Val Thr
65                  70                  75                  80

Ala Lys Val Lys Pro Gln Ser Pro Tyr Gln Val Trp Asp Lys Asn Ser
                85                  90                  95

Ser Ser Lys Asn Leu Asn Pro Arg Leu Gln Lys Ile Leu Lys Asn Tyr
                100                 105                 110

Leu Ser Met Asn Lys Tyr Lys Val Ser Tyr Lys Gly Pro Gly Pro Gly
                115                 120                 125

Val Lys Phe Ser Val Glu Ala Leu Arg Cys His Leu Arg Asp Arg Val
                130                 135                 140

Asn Val Ser Met Ile Glu Ala Thr Asp Phe Pro Phe Asn Thr Thr Glu
145                 150                 155                 160

Trp Glu Gly Tyr Leu Pro Lys Glu Asn Phe Arg Thr Lys Ala Gly Pro
                165                 170                 175

Trp His Arg Cys Ala Val Val Ser Ser Ala Gly Ser Leu Lys Ser Ser
                180                 185                 190

His Leu Gly Lys Glu Ile Asp Ser His Asp Ala Val Leu Arg Phe Asn
                195                 200                 205

Gly Ala Pro Val Ala Asp Phe Gln Gln Asp Val Gly Met Lys Thr Thr
                210                 215                 220

Ile Arg Leu Met Asn Ser Gln Leu Ile Thr Thr Glu Lys Gln Phe Leu
225                 230                 235                 240

Lys Asp Ser Leu Tyr Asn Glu Gly Ile Leu Ile Val Trp Asp Pro Ser
                245                 250                 255

Leu Tyr His Ala Asp Ile Pro Asn Trp Tyr Lys Lys Pro Asp Tyr Asn
                260                 265                 270

Phe Phe Glu Thr Tyr Lys Ser Tyr Arg Lys Leu Tyr Pro Ser Gln Pro
                275                 280                 285

Phe Tyr Ile Leu Arg Pro Gln Met Pro Trp Glu Leu Trp Asp Ile Ile
                290                 295                 300

Gln Glu Ile Ala Pro Asp Arg Ile Gln Pro Asn Pro Pro Ser Ser Gly
305                 310                 315                 320

Met Leu Gly Ile Ile Ile Met Met Thr Leu Cys Asp Gln Val Asp Val
                325                 330                 335

Tyr Glu Phe Leu Pro Ser Lys Arg Lys Thr Asp Val Cys Tyr Tyr His
                340                 345                 350

Gln Lys Phe Phe Asp Ser Ala Cys Thr Met Gly Ala Tyr His Pro Leu
                355                 360                 365

```
Leu Phe Glu Lys Asn Met Val Lys Gln Leu Asn Glu Gly Thr Asp Glu
            370                 375                 380

Asp Ile Tyr Ile Phe Gly Lys Ala Thr Leu Ser Gly Phe Arg Thr Ile
385                 390                 395                 400

His Cys

<210> SEQ ID NO 3
<211> LENGTH: 418
<212> TYPE: PRT
<213> ORGANISM: Homo sapiens

<400> SEQUENCE: 3

Met Thr Arg Leu Thr Val Leu Ala Leu Leu Ala Gly Leu Leu Ala Ser
1               5                   10                  15

Ser Arg Ala Gly Ser Ser Pro Leu Leu Ala Met Glu Trp Ser His Pro
            20                  25                  30

Gln Phe Glu Lys Leu Glu Gly Gly Ser Gly Gly Ser Gly Gly
        35                  40                  45

Ser Trp Ser His Pro Gln Phe Glu Lys His Ala His Ala His Ser Arg
    50                  55                  60

Lys Asp His Leu Ile His Asn Val His Lys Glu Glu His Ala His Ala
65                  70                  75                  80

His Asn Lys Glu Leu Gly Thr Ala Val Phe Gln Gly Pro Met Arg Arg
                85                  90                  95

Ala Ile Arg Gly Arg Ser Phe Gln Val Trp Asn Lys Asp Ser Ser Ser
            100                 105                 110

Lys Asn Leu Ile Pro Arg Leu Gln Lys Ile Trp Lys Asn Tyr Leu Ser
        115                 120                 125

Met Asn Lys Tyr Lys Val Ser Tyr Lys Gly Pro Gly Pro Gly Ile Lys
    130                 135                 140

Phe Ser Ala Glu Ala Leu Arg Cys His Leu Arg Asp His Val Asn Val
145                 150                 155                 160

Ser Met Val Glu Val Thr Asp Phe Pro Phe Asn Thr Ser Glu Trp Glu
                165                 170                 175

Gly Tyr Leu Pro Lys Glu Ser Ile Arg Thr Lys Ala Gly Pro Trp Gly
            180                 185                 190

Arg Cys Ala Val Val Ser Ser Ala Gly Ser Leu Lys Ser Ser Gln Leu
        195                 200                 205

Gly Arg Glu Ile Asp Asp His Asp Ala Val Leu Arg Phe Asn Gly Ala
    210                 215                 220

Pro Thr Ala Asn Phe Gln Gln Asp Val Gly Thr Lys Thr Thr Ile Arg
225                 230                 235                 240

Leu Met Asn Ser Gln Leu Val Thr Thr Glu Lys Arg Phe Leu Lys Asp
                245                 250                 255

Ser Leu Tyr Asn Glu Gly Ile Leu Ile Val Trp Asp Pro Ser Val Tyr
            260                 265                 270

His Ser Asp Ile Pro Lys Trp Tyr Gln Asn Pro Asp Tyr Asn Phe Phe
        275                 280                 285

Asn Asn Tyr Lys Thr Tyr Arg Lys Leu His Pro Asn Gln Pro Phe Tyr
    290                 295                 300

Ile Leu Lys Pro Gln Met Pro Trp Glu Leu Trp Asp Ile Leu Gln Glu
305                 310                 315                 320

Ile Ser Pro Glu Glu Ile Gln Pro Asn Pro Pro Ser Ser Gly Met Leu
                325                 330                 335
```

```
Gly Ile Ile Ile Met Met Thr Leu Cys Asp Gln Val Asp Ile Tyr Glu
            340             345             350

Phe Leu Pro Ser Lys Arg Lys Thr Asp Val Cys Tyr Tyr Tyr Gln Lys
        355             360             365

Phe Phe Asp Ser Ala Cys Thr Met Gly Ala Tyr His Pro Leu Leu Tyr
    370             375             380

Glu Lys Asn Leu Val Lys His Leu Asn Gln Gly Thr Asp Glu Asp Ile
385             390             395             400

Tyr Leu Leu Gly Lys Ala Thr Leu Pro Gly Phe Arg Thr Ile His Cys
                405             410             415

Pro Gly
```